United States Patent

Brown et al.

Patent Number: 6,057,352
Date of Patent: May 2, 2000

[54] FUNGICIDAL CYCLIC AMIDES

[75] Inventors: Richard James Brown, Newark, Del.; Deborah Ann Frasier, Martinez, Calif.; Michael Henry Howard, Jr., Rockland; Gerard Michael Koether, Bear, both of Del.

[73] Assignee: E. I. du Pont de Nemours and Company, Wilmington, Del.

[21] Appl. No.: 08/952,380

[22] PCT Filed: May 8, 1996

[86] PCT No.: PCT/US96/06534

§ 371 Date: Nov. 13, 1997

§ 102(e) Date: Nov. 13, 1997

[87] PCT Pub. No.: WO96/36616

PCT Pub. Date: Nov. 21, 1996

Related U.S. Application Data

[63] Continuation-in-part of application No. 08/442,433, May 17, 1995, abandoned.
[60] Provisional application No. 60/004,183, Sep. 22, 1995.

[51] Int. Cl.$^7$ ............... C07D 249/12; C07D 233/30; A01N 43/74; A01N 43/56
[52] U.S. Cl. ............... 514/384; 514/386; 548/263.4; 548/264.6; 548/316.7; 548/325.1; 548/325.5; 548/263.8
[58] Field of Search ............... 514/384, 359, 514/386, 360; 548/263.4, 263.8, 264.6, 316.7, 325.1, 325.5

[56] References Cited

U.S. PATENT DOCUMENTS

| | | | |
|---|---|---|---|
| 4,098,896 | 7/1978 | Edwards | 424/269 |
| 5,108,486 | 4/1992 | Kondo et al. | 71/92 |
| 5,416,110 | 5/1995 | Wingert et al. | 514/488 |
| 5,474,974 | 12/1995 | Kruger et al. | 504/236 |
| 5,747,516 | 5/1998 | Brown et al. | 514/359 |

FOREIGN PATENT DOCUMENTS

| | | | |
|---|---|---|---|
| 0 508 126 | 10/1992 | European Pat. Off. | C07D 231/32 |
| 0 617 014 | 9/1994 | European Pat. Off. | C07C 327/58 |
| 44 13 669 | 1/1995 | Germany | C07D 307/94 |
| WO 94/11334 | 5/1994 | WIPO | C07C 70/734 |
| WO 95/14009 | 5/1995 | WIPO | C07D 249/12 |
| WO 95/18789 | 7/1995 | WIPO | C07C 251/60 |
| WO 96/17851 | 6/1996 | WIPO | C07F 7/08 |
| WO 96/26191 | 8/1996 | WIPO | C07D 249/12 |
| WO 96/36633 | 11/1996 | WIPO | C07D 405/04 |
| WO96/36229 | 11/1996 | WIPO | A01N 43/653 |
| WO 97/02255 | 1/1997 | WIPO | C07D 261/12 |

OTHER PUBLICATIONS

Zvilichovsky, G., *J. Heterocyclic Chem.*, 24, 465–470, 1987.
Zvilichovsky, G. et al., *J. Heterocyclic Chem.*, 25, 1307–1310, 1988.
Davis, M. et al., *Australian J. Chem.*, 30(8), 1815–1818, 1977.

*Primary Examiner*—Mukund J. Shah
*Assistant Examiner*—Deepak R. Rao

[57] ABSTRACT

Compounds of Formula (I),

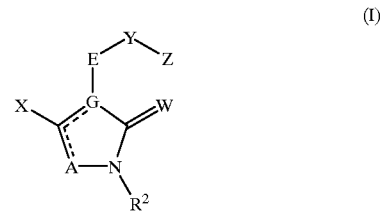

and their N-oxides and agriculturally suitable salts are disclosed which are useful as fungicides, wherein E is 1,2-phenylene optionally substituted with one of $R^3$, $R^4$, or both $R^3$ and $R^4$; A is O; S; N; $NR^5$; or $CR^{14}$; G is C or N; provided that when G is C, then A is O, S or $NR^5$ and the floating double bond is attached to G; and when G is N, then A is N or $CR^{14}$ and the floating double bond is attached to A; W is O; S; NH; $N(C_1-C_6$ alkyl); or $NO(C_1-C_6$ alkyl); X is $OR^1$; $S(O)_m R^1$; or halogen; $R^1$ is $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; or $C_2-C_4$ alkoxycarbonyl; $R^2$ is H; $C_1-C_6$ alkyl; $C_1-C_6$ haloalkyl; $C_2-C_6$ alkenyl: $C_2-C_6$ haloalkenyl; $C_2-C_6$ alkynyl; $C_2-C_6$ haloalkenyl; $C_3-C_6$ cycloalkyl; $C_2-C_4$ alkylcarbonyl: $C_2$-alkoxycarbonyl; hydroxy; $C_1-C_2$ alkoxy; or acetyloxy; and Y, Z, $R^3$, $R^4$, $R^5$, $R^{14}$ and m are as defined in the disclosure. Also disclosed are compositions containing the compounds of Formula (I) and a method for controlling plant diseases caused by fungal plant pathogens which involves applying an effective amount of a compound of Formula (I).

10 Claims, No Drawings

FUNGICIDAL CYCLIC AMIDES

This application is a national filing under 35 USC 371 of International Application Number PCT/US96/06534 filed May 8, 1996 and claiming priority of U.S. Provisional Application No. 60/004,183 filed Sep. 22, 1995 which is continuation-in-part of U.S. patent application Ser. No. 08/442,433 filed May 17, 1995, now abandoned.

BACKGROUND OF THE INVENTION

This invention relates to certain cyclic amides, their N-oxides, agriculturally suitable salts and compositions, and methods of their use as fungicides.

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different modes of action.

WO 94/11334 discloses certain amides and esters of Formula i as fungicides

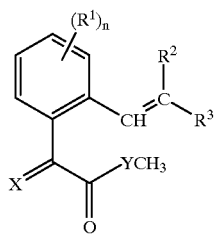

wherein n is 0–4;

X is CHOCH$_3$, CHCH$_3$, or NOCH$_3$;

Y is O or NH;

R$^1$ is, among others, nitro; cyano; halogen; C$_1$–C$_4$ alkyl; C$_1$–C$_4$ haloalkyl; C$_1$–C$_4$ alkoxy; C$_1$–C$_4$ haloalkoxy; or C$_1$–C$_4$ alkylthio;

R$^2$ is, among others, nitro, cyano, halogen, C$_1$–C$_4$ alkoxy, C$_1$–C$_4$ alkylcarbonylanrino, or C$_1$–C$_4$ alkoxycarbonylamino;

R$^3$ is, among others, R$^4$—T—C(=Z$^1$)— or R$^5$—C(=Z$^2$)—;

Z$^1$ is, among others, O or S;

Z$^2$ is, among others, O or S; and

T is, among others, O, S, or NR$^7$; and

EP-A-617,014 discloses certain amides and esters of Formula ii as fungicides

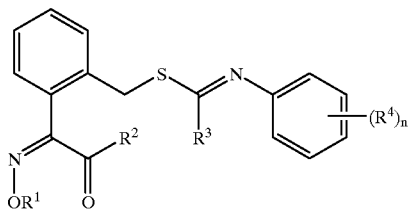

wherein

R$^1$ is C$_1$–C$_6$ alkyl;

R$^2$ is OR$^5$ or NHR$^6$;

R$^3$ is C$_3$–C$_8$ cycloalkyl;

R$^4$ is, among others, C$_1$–C$_{10}$ alkoxy, C$_2$–C$_7$ alkoxycarbonyl, halogen, cyano, C$_1$–C$_6$ alkylthio, C$_1$–C$_6$ alkyl, or C$_1$–C$_6$ haloalkyl;

R$^5$ and R$^6$ are C$_1$–C$_6$ alkyl; and n is 0–5.

EP-A-656,351, WO 95/18789 and WO 95/21153 also disclose amides and esters similar to those in the above two publications as fungicides.

The cyclic amides of the present invention are not disclosed in any of the above publications.

*J. Heterocyclic Chem.*, (1987), 24, 465, *J. Heterocyclic Chem.*, (1988), 25, 1307, and *Australian J. Chem.*, (1977), 30 (8), 1815 disclose 4-nitrophenyl isoxazoles (iii), phenyl pyrazolones (iv), and aryl isothiazolinones (v) respectively.

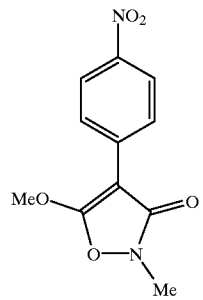

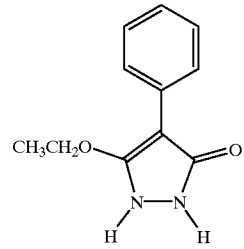

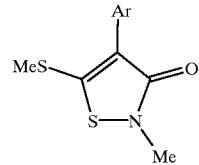

However, no utility as fungicides is alleged and the cyclic amides of the present invention are not disclosed therein.

SUMMARY OF THE INVENTION

This invention is directed to compounds of Formula I including all geometric and stereoisomers, N-oxides, and agriculturally suitable salts thereof, agricultural compositions containing them and their use as fungicides:

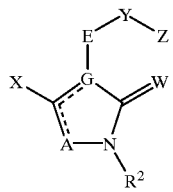

wherein
E is 1,2-phenylene optionally substituted with one of $R^3$, $R^4$, or both $R^3$ and $R^4$;
A is O; S; N; $NR^5$; or $CR^{14}$;
G is C or N; provided that when G is C, then A is O, S or $NR^5$ and the floating double bond is attached to G; and when G is N, then A is N or $CR^{14}$ and the floating double bond is attached to A;
W is O; S; NH; $N(C_1-C_6$ alkyl); or $NO(C_1-C_6$ alkyl);
X is $OR^1$; $S(O)_m R^1$; or halogen;
$R^1$ is $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; or $C_2-C_4$ alkoxycarbonyl;
$R^2$ is H; $C_1-C_6$ alkyl; $C_1-C_6$ haloalkyl; $C_2-C_6$ alkenyl; $C_2-C_6$ haloalkenyl; $C_2-C_4$ alkynyl; $C_2-C_6$ haloalkynyl; $C_3-C_6$ cycloalkyl; $C_2-C_4$ alkylcarbonyl; $C_2-C_4$ alkoxycarbonyl; hydroxy; $C_1-C_2$ alkoxy; or acetyloxy;
$R^3$ and $R^4$ are each independently halogen; cyano; nitro; hydroxy; $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_1-C_6$ alkoxy; $C_1-C_6$ haloalkoxy; $C_2-C_6$ alkenyloxy; $C_2-C_6$ alkynyloxy; $C_1-C_6$ alkylthio; $C_1-C_6$ alkylsulfinyl; $C_1-C_6$ alkylsulfonyl; formyl; $C_2-C_6$ alkylcarbonyl; $C_2-C_6$ alkoxycarbonyl; $NH_2C(O)$; $(C_1-C_4$ alkyl)NHC(O); $(C_1-C_4$ alkyl$)_2$NC(O); $Si(R^{25})_3$; $Ge(R^{25})_3$; $(R^{25})_3Si-C\equiv C-$; or phenyl, phenylethynyl, benzoyl, or phenylsulfonyl each substituted with $R^8$ and optionally substituted with one or more $R^{10}$; or
when $R^3$ and $R^4$ are attached to adjacent atoms, $R^3$ and $R^4$ can be taken together as $C_3-C_5$ alkylene, $C_3-C_5$ haloalkylene, $C_3-C_5$ alkenylene or $C_3-C_5$ haloalkenylene each optionally substituted with 1–2 $C_1-C_3$ alkyl;
$R^5$ is H; $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; or $C_2-C_4$ alkoxycarbonyl;
Y is $-NR^{15}-$; $-C(=O)-$; $-CHR^{15}OC(=S)N(R^{15})-$; $-CHR^{15}OC(=O)O-$; $-CHR^{15}OC(=S)O-$; $-CHR^{15}OC(=O)S-$; $-CHR^{15}OC(=S)S-$; $-CHR^{15}SC(=O)N(R^{15})-$; $-CHR^{15}SC(=S)N(R^{15})-$; $-CHR^{15}SC(=O)O-$; $-CHR^{15}SC(=S)O-$; $-CHR^{15}SC(=O)S-$; $-CHR^{15}SC(=S)S-$; $-CHR^{15}SC(=NR^{15})S-$; $-CHR^{15}N(R^{15})C(=O)N(R^{15})-$; $-CHR^{15}O-N(R^{15})C(=O)N(R^{15})-$; $-CHR^{15}O-N(R^{15})C(=S)N(R^{15})-$; $-CHR^{15}O-N=C(R^7)NR^{15}-$; $-CHR^{15}O-N=C(R^7)OCH_2-$; $-CHR^{15}O-N=C(R^7)-N=N-$; $-CHR^{15}O-N=C(R^7)-C(=O)-$; $-CHR^{15}O-N=C(R^7)-C(=N-A^2-Z^1)-A^1-$; $-CHR^{15}O-N=C(R^7)-C(R^7)=N-A^2-A^3-$; $-CHR^{15}O-N=C(-C(R^7)=N-A^2-Z^1)-$; $-CHR^{15}O-N=C(R^7)-CH_2O-$; $-CHR^{15}O-N=C(R^7)-CH_2S-$; $-O-CH_2CH_2O-N=C(R^7)-$; $-CHR^{15}O-C(R^7)=N-$; $-CHR^{15}S-C(R^7)=N-$; $-C(R^7)=N-NR^{15}-$; $-CH=N-N=C(R^7)-$; $-CHR^{15}N(R^{15})-N=C(R^7)-$; $-CHR^{15}N(COCH_3)-N=C(R^7)-$; $-OC(=S)NR^{15}C(=O)-$; $-CHR^6-C(=W^1)-A^1-$; $-CHR^6CHR^6-C(=W^1)-A^1-$; $-CR^6=CR^6-C(=W^1)-A^1-$; $-C\equiv C-C(=W^1)-A^1-$; $-N=CR^6-C(=W^1)-A^1-$; $-CH(OR^{26})-$; $-CHR^{27}-$; $-CHR^6CHR^{28}-$; $-CHR^{28}CHR^6-$; $-CR^6=CR^{29}-$; $-CR^{29}=CR^6-$; $-CHR^{30}O-$; $-OCHR^{30}-$; $-CHR^{30}S(O)_n-$; $-S(O)_n CHR^{30}-$; $-CHR^{30}O-N=C(R^7)-$; $-CHR^{15}O-N=C(R^{31})-$; $-(R^7)C=N-OCH(R^{30})-$; $-(R^{31})C=N-OCH(R^{15})-$; $-C(R^{31})=N-O-$; $-O-N=C(R^{31})-$; $-CHR^{30}OC(=O)N(R^{15})-$; or $-CHR^{15}OC(=O)N(R^{32})-$; and the directionality of the Y linkage is defined such that the moiety depicted on the left side of the linkage is bonded to E and the moiety on the right side of the linkage is bonded to Z;
$Z^1$ is H or $-A^3-Z$;
$W^1$ is O or S;
$A^1$ is O; S; $NR^{15}$; or a direct bond;
$A^2$ is O; $NR^{15}$; or a direct bond;
$A^3$ is $-C(=O)-$; $-S(O)_2-$; or a direct bond;
each $R^6$ is independently H; 1–2 $CH_3$; $C_2-C_3$ alkyl; $C_1-C_3$ alkoxy; $C_3-C_6$ cycloalkyl; formylamino; $C_2-C_4$ alkylcarbonylamino; $C_2-C_4$ alkoxycarbonylamino; $NH_2C(O)NH$; $(C_1-C_3$ alkyl)NHC(O)NH; $(C_1-C_3$ alkyl$)_2$NC(O)NH; $N(C_1-C_3$ alkyl$)_2$; piperidinyl; morpholinyl; 1–2 halogen; cyano; or nitro;
each $R^7$ is independently H; $C_1-C_6$ alkyl; $C_1-C_6$ haloalkyl; $C_1-C_6$ alkoxy; $C_1-C_6$ haloalkoxy; $C_1-C_6$ alkylthio; $C_1-C_6$ alkylsulfinyl; $C_1-C_6$ alkylsulfonyl; $C_1-C_6$ haloalkylthio; $C_1-C_6$ haloalkylsulfinyl; $C_1-C_6$ haloalkylsulfonyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; $C_2-C_4$ alkoxycarbonyl; halogen; cyano; nitro; hydroxy; amino; $NH(C_1-C_6$ alkyl); $N(C_1-C_6$ alkyl)2; or morpholinyl;
each Z is independently selected from:
  i) $C_1-C_{10}$ alkyl, $C_2-C_{10}$ alkenyl, and $C_2-C_{10}$ alkynyl each substituted with $R^9$ and optionally substituted with one or more $R^{10}$;
  ii) $C_3-C_8$ cycloalkyl, $C_3-C_8$ cycloalkenyl and phenyl each substituted with $R^9$ and optionally substituted with one or more $R^{10}$;
  iii) a ring system selected from 3 to 14-membered monocyclic, fused bicyclic and fused tricyclic nonaromatic heterocyclic ring systems and 5 to 14-membered monocyclic, fused bicyclic and fused tricyclic aromatic heterocyclic ring systems, each heterocyclic ring system containing 1 to 6 heteroatoms independently selected from the group nitrogen, oxygen, and sulfur, provided that each heterocyclic ring system contains no more than 4 nitrogens, no more than 2 oxygens, and no more than 2 sulfurs, each nonaromatic or aromatic heterocyclic ring system substituted with $R^9$ and optionally substituted with one or more $R^{10}$;
  iv) a multicyclic ring system selected from 8 to 14-membered fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$, and any remaining rings as aromatic carbocyclic rings, each multicyclic ring system substituted with R$^9$ and optionally substituted with one or more R$^{10}$; and v) adamantyl substituted with R$^9$ and optionally substituted with one or more R$^{10}$;

each Q is independently selected from the group —CHR$^{13}$—, —NR13—, —O—, and —S(O)$_p$—;

R$^8$ is H; 1–2 halogen; C$_1$–C$_6$ alkyl; C$_1$–C$_6$ haloalkyl; C$_1$–C$_6$ alkoxy; C$_1$–C$_6$ haloalkoxy; C$_2$–C$_6$ alkenyl; C$_2$–C$_6$ haloalkenyl; C$_2$–C$_6$ alkynyl; C$_1$–C$_6$ alkylthio; C$_1$–C$_6$ haloalkylthio; C$_1$–C$_6$ alkylsulfinyl; C$_1$–C$_6$ alkylsulfonyl; C$_3$–C$_6$ cycloalkyl; C$_3$–C$_6$ alkenyloxy; CO$_2$ (C$_1$–C$_6$ alkyl); NH(C$_1$–C$_6$ alkyl); N(C$_1$–C$_6$ alkyl)$_2$; cyano; nitro; SiR$^{19}$R$^{20}$R$^{21}$; or GeR$^{19}$R$^{20}$R$^{21}$;

R$^9$ is H; 1–2 halogen; C$_1$–C$_6$ alkyl; C$_1$–C$_6$ haloalkyl; C$_1$–C$_6$ alkoxy; C$_1$–C$_6$ haloalkoxy; C$_2$–C$_6$ alkenyl; C$_2$–C$_6$ haloalkenyl; C$_2$–C$_6$ alkynyl; C$_1$–C$_6$ alkylthio; C$_1$–C$_6$ haloalkylthio; C$_1$–C$_6$ alkylsulfinyl; C$_1$–C$_6$ alkylsulfonyl; C$_3$–C$_6$ cycloalkyl; C$_3$–C$_6$ alkenyloxy; CO$_2$ (C$_1$–C$_6$ alkyl); NH(C$_1$–C$_6$ alkyl); N(C$_1$–C$_6$ alkyl)$_2$; —C(R$^{18}$)=NOR$^{17}$; cyano; nitro; SF$_5$; SiR$^{22}$R$^{23}$R$^{24}$; or GeR$^{22}$R$^{23}$R$^{24}$; or R$^9$ is phenyl, benzyl, benzoyl, phenoxy, pyridinyl, pyridinyloxy, thienyl, thienyloxy, furanyl, pyrimidinyl, or pyrimidinyloxy each optionally substituted with one of R$^{11}$, R$^{12}$, or both R$^{11}$ and R$^{12}$;

each R$^{10}$ is independently halogen; C$_1$–C$_4$ alkyl; C$_1$–C$_4$ haloalkyl; C$_1$–C$_4$ alkoxy; nitro; or cyano; or when R$^9$ and an R$^{10}$ are attached to adjacent atoms on Z, R$^9$ and said adjacently attached R$^{10}$ can be taken together as —OCH$_2$O— or —OCH$_2$CH$_2$O—; each CH$_2$ group of said taken together R$^9$ and R$^{10}$ optionally substituted with 1–2 halogen; or when Y and an R$^{10}$ are attached to adjacent atoms on Z and Y is
—O—CH$_2$CH$_2$O—N=C(R$^7$)—, —CHR$^{15}$O—C(R$^{15}$)=C(R$^7$)—, —CH=N—N=C(R$^7$)—,
—CHR$^{15}$N(R$^{15}$)—N=C(R$^7$)—, —CHR$^{15}$N(COCH$_3$)—N=C(R$^7$)— or
—CHR$^{30}$O—N=C(R$^7$)—, R$^7$ and said adjacently attached R$^{10}$ can be taken together as —(CH$_2$)$_r$—J— such that J is attached to Z;

J is —CH$_2$—; —CH$_2$CH$_2$—; —OCH$_2$—; —CH$_2$O—; —SCH$_2$—; —CH$_2$S—; —N(R$^{16}$)CH$_2$—; or —CH$_2$N(R$^{16}$)—; each CH$_2$ group of said J optionally substituted with 1 to 2 CH$_3$;

R$^{11}$ and R$^{12}$ are each independently halogen; C$_1$–C$_4$ alkyl; C$_1$–C$_4$ haloalkyl; C$_1$–C$_4$ alkoxy; C$_1$–C$_4$ haloalkoxy; nitro; cyano; Si(R$^{25}$)$_3$; or Ge(R$^{25}$)$_3$;

each R$^{13}$ is independently H; C$_1$–C$_6$ alkyl; C$_1$–C$_6$ haloalkyl; or phenyl optionally substituted with halogen, C$_1$–C$_4$ alkyl, C$_1$–C$_4$ haloalkyl, C$_1$–C$_4$ alkoxy, C$_1$–C$_4$ haloalkoxy, nitro or cyano;

R$^{14}$ is H; halogen; C$_1$–C$_6$ alkyl; C$_1$–C$_6$ haloalkyl; C$_2$–C$_6$ alkenyl; C$_2$–C$_6$ haloalkenyl; C$_2$–C$_6$ alkynyl; C$_2$–C$_6$ haloalkynyl; or C$_3$–C$_6$ cycloalkyl;

each R$^{15}$ is independently H; C$_1$–C$_3$ alkyl; C$_3$–C$_6$ cycloalkyl; or phenyl or benzyl, each optionally substituted on the phenyl ring with halogen, C$_1$–C$_4$ alkyl, C$_1$–C$_4$ haloalkyl, C$_1$–C$_4$ alkoxy, C$_1$–C$_4$ haloalkoxy, nitro or cyano; or when Y is —CHR$^{15}$N(R$^{15}$)C(=O)N(R$^{15}$)—, the two R$^{15}$ attached to nitrogen atoms on said group can be taken together as —(CH$_2$)$_s$—; or when Y is —CHR$^{15}$O—N=C(R$^7$)NR$^{15}$—, R$^7$ and the adjacently attached R$^{15}$ can be taken together as —CH$_2$—(CH$_2$)$_s$—; —O—(CH$_2$)$_s$—; —S—(CH$_2$)$_s$—; or
—N(C$_1$–C$_3$ alkyl)—(CH$_2$)$_s$—; with the directionality of said linkage defined such that the moiety depicted on the left side of the linkage is bonded to the carbon and the moiety on the right side of the linkage is bonded to the nitrogen;

R$^{16}$, R$^{17}$, and R$^{18}$ are each independently H; C$_1$–C$_3$ alkyl; C$_3$–C$_6$ cycloalkyl; or phenyl optionally substituted with halogen, C$_1$–C$_4$ alkyl, C$_1$–C$_4$ haloalkyl, C$_1$–C$_4$ alkoxy, C$_1$–C$_4$ haloalkoxy, nitro or cyano;

R$^{19}$, R$^{20}$, R$^{21}$, R$^{22}$, R$^{23}$, and R$^{24}$ are each independently C$_1$–C$_6$ alkyl; C$_2$–C$_6$ alkenyl; C$_1$–C$_4$ alkoxy; or phenyl;

each R$^{25}$ is independently C$_1$–C$_4$ alkyl; C$_1$–C$_4$ haloalkyl; C$_2$–C$_4$ alkenyl; C$_{1-C4}$ alkoxy; or phenyl;

R$^{26}$ is H; C$_1$–C$_3$ alkyl; C$_3$–C$_6$ cycloalkyl; or phenyl optionally substituted with halogen, C$_1$–C$_4$ alkyl, C$_1$–C$_4$ haloalkyl, C$_1$–C$_4$ alkoxy, C$_1$–C$_4$ haloalkoxy, nitro or cyano;

R$^{27}$ and R$^{28}$ are each independently C$_1$–C$_3$ alkoxy; C$_3$–C$_6$ cycloalkyl; formylamino; C$_2$–C$_4$ alkylcarbonylamino; C$_2$–C$_4$ alkoxycarbonylarnino; NH$_2$C(O)NH; (C$_1$–C$_3$ alkyl)NHC(O)NH; (C$_1$–C$_3$ alkyl)$_2$NC(O)NH; N(C$_1$–C$_3$ alkyl)$_2$; piperidinyl; morpholinyl; cyano; or nitro;

R$^{29}$ is C$_1$–C$_3$ alkoxy; C$_3$–C$_6$ cycloalkyl; formylamino; C$_2$–C$_4$ alkylcarbonylamino; C$_2$–C$_4$ alkoxycarbonylamino; NH$_2$C(O)NH; (C$_1$–C$_3$ alkyl)NHC(O)NH; (C$_1$–C$_3$ alkyl)$_2$NC(O)NH; N(C$_1$–C$_3$ alkyl)2; piperidinyl; morpholinyl; halogen; cyano; or nitro;

R$^{30}$ is C$_3$–C$_6$ cycloalkyl; or phenyl optionally substituted with halogen, C$_1$–C$_4$ alkyl, C$_1$–C$_4$ haloalkyl, C$_1$–C$_4$ alkoxy, C$_1$–C$_4$ haloalkoxy, nitro or cyano; R$^{31}$ is C$_1$–C$_6$ alkylthio; C$_1$–C$_6$ alkylsulfinyl; C$_1$–C$_6$ alkylsulfonyl; C$_1$–C$_6$ haloalkylthio; C$_1$–C$_6$ haloalkylsulfinyl; C$_1$–C$_6$ haloalkylsulfonyl; nitro; hydroxy; amino; NH(C$_1$–C$_6$ alkyl); N(C$_1$–C$_6$ alkyl)$_2$; or halogen;

R$^{32}$ is C$_3$–C$_6$ cycloalkyl;

m, n and p are each independently 0, 1 or 2;

r is 0 or 1; and s is 2 or 3;

provided that
i) when Y is —CH(OR$^{26}$)—, —CHR$^{27}$—, —CHR$^6$CHR$^{28}$—, —CHR$^{28}$CHR$^6$—, —OCHR$^{30}$—, —S(O)$_n$CHR$^{30}$— or —(R$^7$)C=N—OCH(R$^{30}$)— and Z is C$_1$–C$_{10}$ alkyl, C$_2$–C$_{10}$ alkenyl, or C$_2$–C$_{10}$ alkynyl each substituted with R$^9$ and optionally substituted with one or more R$^{10}$, then R$^9$ is other than H, C$_1$–C$_6$ alkyl, C$_2$–C$_6$ alkenyl, or C$_2$–C$_6$ alkynyl;

ii) when Y is —CR$^6$=CR$^{29}$— or —CR$^{29}$=CR$^6$— and Z is C$_1$–C$_{10}$ alkyl or C$_2$–C$_{10}$ alkenyl each substituted with R$^9$ and optionally substituted with one or more R$^{10}$, then R$^9$ is other than H, 1–2 halogen, C$_1$–C$_6$ alkyl, C$_1$–C$_6$ haloalkyl, C$_2$–C$_6$ alkenyl, or C$_2$–C$_6$ haloalkenyl;

iii) when Y is —NR$^{15}$—, R$^{15}$ is H or C$_1$–C$_3$ alkyl, and R$^9$ is SiR$^{22}$R$^{23}$R$^{24}$ or GeR$^{22}$R$^{23}$R$^{24}$, then Z is other than phenyl or a 5 to 14-membered aromatic heterocyclic ring system each substituted with R$^9$ and optionally substituted with one or more R$^{10}$;

iv) when Y is —C(=O)— and R$^9$ is SiR$^{22}$R$^{23}$R$^{24}$ or GeR$^{22}$R$^{23}$R$^{24}$, then Z is other than phenyl or a 5 to 14-membered aromatic heterocyclic ring system each substituted with $R^9$ and optionally substituted with one or more $R^{10}$;

v) when Y is —CH(OR$^{26}$)—, $R^{26}$ is H or $C_1$–$C_3$ alkyl, and $R^9$ is SiR$^{22}$R$^{23}$R$^{24}$ or GeR$^{22}$R$^{23}$R$^{24}$, then Z is other than phenyl or a 5 to 14-membered aromatic heterocyclic ring system each substituted with $R^9$ and optionally substituted with one or more $R^{10}$;

vi) when Y is —NR$^{15}$— and $R^{15}$ is H or $C_1$–$C_3$ alkyl, then Z is other than
  i) an N-oxide of a 5 to 14-membered aromatic heterocyclic ring system substituted with $R^9$ and optionally substituted with one or more $R^{10}$;
  ii) a 8 to 14-membered multicyclic ring system selected from fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$ substituted with $R^9$ and optionally substituted with one or more $R^{10}$; or
  iii) adamantyl substituted with $R^9$ and optionally substituted with one or more $R^{10}$;

vii) when Y is —CHR$^{15}$O—N=C(R$^{31}$)— or —(R$^{31}$)C=N—OCH(R$^{15}$)—, $R^{15}$ is H or $C_1$–$C_3$ alkyl and $R^{31}$ is $C_1$–$C_6$ alkylthio, $C_1$–$C_6$ alkylsulfinyl, $C_1$–$C_6$ alkylsulfonyl, $C_1$–$C_6$ haloalkylthio, $C_1$–$C_6$ haloalkylsulfinyl, $C_1$–$C_6$ haloalkylsulfonyl or halogen, then Z is other than
  i) an N-oxide of a 5 to 14-membered aromatic heterocyclic ring system substituted with $R^9$ and optionally substituted with one or more $R^{10}$;
  ii) a 8 to 14-membered multicyclic ring system selected from fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$ substituted with $R^9$ and optionally substituted with one or more $R^{10}$; or
  iii) adamantyl substituted with $R^9$ and optionally substituted with one or more $R^{10}$;

viii) when Y is —C(=O)—, then Z is other than
  i) an N-oxide of a 5 to 14-membered aromatic heterocyclic ring system substituted with $R^9$ and optionally substituted with one or more $R^{10}$;
  ii) a 8 to 14-membered multicyclic ring system selected from fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$ substituted with $R^9$ and optionally substituted with one or more $R^{10}$; or
  iii) adamantyl substituted with $R^9$ and optionally substituted with one or more $R^{10}$;

ix) when Y is —C(R$^{31}$)=N—O— or —O—N=C(R$^{31}$)— and $R^{31}$ is $C_1$–$C_6$ alkylthio, $C_1$–$C_6$ alkylsulfinyl, $C_1$–$C_6$ alkylsulfonyl, $C_1$–$C_6$ haloalkylthio, $C_1$–$C_6$ haloalkylsulfinyl, $C_1$–$C_6$ haloalkylsulfonyl or halogen, then Z is other than
  i) an N-oxide of a 5 to 14-membered aromatic heterocyclic ring system substituted with $R^9$ and optionally substituted with one or more $R^{10}$;
  ii) a 8 to 14-membered multicyclic ring system selected from fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$ substituted with $R^9$ and optionally substituted with one or more $R^{10}$; or
  iii) adamantyl substituted with $R^9$ and optionally substituted with one or more $R^{10}$; and x) when Y is —CH(OR$^{26}$)— and $R^{26}$ is H or $C_1$–$C_3$ alkyl, then Z is other than
  i) an N-oxide of a 5 to 14-membered aromatic heterocyclic ring system substituted with $R^9$ and optionally substituted with one or more $R^{10}$;
  ii) a 8 to 14-membered multicyclic ring system selected from fused-bicyclic and fused-tricyclic ring systems which are an aromatic carbocyclic ring system, a nonaromatic carbocyclic ring system, or a ring system containing a one or two nonaromatic rings that each include one or two Q as ring members and one or two ring members independently selected from C(=O) and S(O)$_2$ substituted with $R^9$ and optionally substituted with one or more $R^{10}$; or
  iii) adamantyl substituted with $R^9$ and optionally substituted with one or more $R^{10}$.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–2 CH$_3$" indicates that the substituent can be methyl or, when there is a hydrogen attached to the same atom, the substituent and said hydrogen can both be methyl. The term "1–2 alkyl" indicates that one or two of the available positions for that substituent may be alkyl which are independently selected. "Alkenyl" includes straight-chain or branched alkenes such as vinyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain alkanediyl. Examples of "alkylene" include CH$_2$CH$_2$CH$_2$, CH$_2$CH$_2$CH$_2$CH$_2$, CH$_2$CH$_2$CH$_2$CH$_2$CH$_2$. "Alkenyle" denotes a straight-chain alkenediyl containing one olefinic bond. Examples of "alkenylene" include CH$_2$CH=CH, CH$_2$CH$_2$CH=CH, CH$_2$CH=CHCH$_2$ and CH$_2$CH=CHCH$_2$CH$_2$. "Alkoxy" includes, for example, methoxy, ethoxy, n-propyloxy, isopropyloxy and the different butoxy, pentoxy and hexyloxy isomers. "Alkenyloxy" includes straight-chain or branched alkenyloxy moieties. Examples of "alkenyloxy" include H$_2$C=CHCH$_2$O, (CH$_3$)$_2$C=CHCH$_2$O, (CH$_3$)CH=CHCH$_2$O, (CH$_3$)CH=C(CH$_3$)CH$_2$O and CH$_2$=CHCH$_2$CH$_2$O. "Alkynyloxy" includes straight-chain or branched alkynyloxy moieties. Examples of "alkynyloxy" include HC≡CCH$_2$O, CH$_3$C≡CCH$_2$O and CH$_3$C≡CCH$_2$CH$_2$O. "Alkylthio" includes branched or straight-chain aLkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Cycloalkyl" includes, for example, cyclopropyl, cyclobutyl, cyclopentyl, and cyclohexyl. "Cycloalkenyl" includes groups such as cyclopentenyl and cyclohexenyl as well as groups with more than one double bond such as 1,3- and 1,4-cyclohexadienyl. The term "aromatic carbocyclic ring system" includes fully aromatic carbocycles and carbocycles in which at least one ring of a polycyclic ring system is aromatic (where aromatic indicates that the Hückel rule is satisfied). The term "nonaromatic carbocyclic ring system" denotes fully saturated carbocycles as well as partially or fully unsaturated carbocycles where the Hückel rule is not satisfied by any of the rings in the ring system. The term "aromatic heterocyclic ring system" includes fully aromatic heterocycles and heterocycles in which at least one ring of a polycyclic ring system is aromatic (where aromatic indicates that the Hückel rule is satisfied). The term "nonaromatic heterocyclic ring system" denotes fully saturated heterocycles as well as partially or fully unsaturated heterocycles where the Hückel rule is not satisfied by any of the rings in the ring system. The heterocyclic ring systems can be attached through any available carbon or nitrogen by replacement of a hydrogen on said carbon or nitrogen. One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides.

The term "halogen", either alone or in compound words such as "haloalkyl", includes fluorine, chlorine, bromine or iodine. The term "1–2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

The total number of carbon atoms in a substituent group is indicated by the "$C_i$–$C_j$" prefix where i and j are numbers from 1 to 10. For example, $C_1$–$C_3$ alkylsulfonyl designates methylsulfonyl through propylsulfonyl. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. In the above recitations, when a compound of Formula I is comprised of one or more heterocyclic rings, all substituents are attached to these rings through any available carbon or nitrogen by replacement of a hydrogen on said carbon or nitrogen.

When a group contains a substituent which can be hydrogen, for example $R^9$ or $R^{13}$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a phenol.

Preferred compounds for reasons of better activity and/or ease of synthesis are:

Preferred 1. Compounds of Formula I above, and N-oxides and agriculturally suitable salts thereof, wherein:

W is O;

$R^1$ is $C_1$–$C_3$ alkyl or $C_1$–$C_3$ haloalkyl;

$R^2$ is H; $C_1$–$C_6$ alkyl; $C_1$–$C_6$ haloalkyl; or $C_3$–$C_6$ cycloalkyl;

$R^3$ and $R^4$ are each independently halogen; cyano; nitro; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_1$–$C_6$ alkylsulfonyl; $C_2$–$C_6$ alkylcarbonyl; $C_2$–$C_6$ alkoxycarbonyl; $(C_1$–$C_4$ alkyl)NHC(O); $(C_1$–$C_4$ alkyl)$_2$NC(O); benzoyl; or phenylsulfonyl;

Y is —$CH_2O$—N═C($R^7$)—C(═O)—; —$CH_2S$—C($R^7$)═N—; —CH═C$R^6$—C(═$W^1$)—$A^1$—; —$CH_2O$—N═C($R^{31}$)—; —($R^7$)C═N—OCH($R^{30}$)—; or —C($R^{31}$)═N—O—;

$R^7$ is H; $C_1$–$C_6$ alkyl; $C_1$–$C_6$ haloalkyl; $C_1$–$C_6$ alkoxy; $C_1$14 $C_6$ alkylthio; $C_2$–$C_6$ alkenyl; $C_2$–$C_6$ alkynyl; $C_3$–$C_6$ cycloalkyl; halogen; or cyano;

Z is selected from the group $C_1$–$C_{10}$ alkyl; $C_3$–$C_8$ cycloalkyl; phenyl; naphthalenyl; anthracenyl; phenanthrenyl; 1H-pyrrolyl; furanyl; thienyl; 1H-pyrazolyl; 1H-imidazolyl; isoxazolyl; oxazolyl; isothiazolyl; thiazolyl; 1H-1,2,3-triazolyl; 2H-1,2,3-triazolyl; 1H-1,2,4-triazolyl; 4H-1,2,4-triazolyl; 1,2,3-oxadiazolyl; 1,2,4-oxadiazolyl; 1,2,5-oxadiazolyl; 1,3,4-oxadiazolyl; 1,2,3-thiadiazolyl; 1,2,4-thiadiazolyl; 1,2,5-thiadiazolyl; 1,3,4-thiadiazolyl; 1H-tetrazolyl; 2H-tetrazolyl; pyridinyl; pyridazinyl; pyrimidinyl; pyrazinyl; 1,3,5-triazinyl; 1,2,4-triazinyl; 1,2,4,5-tetrazinyl; 1H-indolyl; benzofuranyl; benzo[b]thiophenyl; 1H-indazolyl; 1H-benzimidazolyl; benzoxazolyl; benzothiazolyl; quinolinyl; isoquinolinyl; cinnolinyl; phthalazinyl; quinazolinyl; quinoxalinyl; 1,8-naphthyridinyl; pteridinyl; 2,3-dihydro-1H-indenyl; 1,2,3,4- tetrahydronaphthalenyl; 6,7,8,9-tetrahydro-5H-benzocycloheptenyl; 5,6,7,8,9,10-hexahydrobenzocyclooctenyl; 2,3-dihydro-3-oxobenzofuranyl; 1,3-dihydro-1-oxoisobenzofuranyl; 2,3-dihydro-2-oxobenzofuranyl; 3,4-dihydro-4-oxo-2H-1-benzopyranyl; 3,4-dihydro-1-oxo-1H-2-benzopyranyl; 3,4-dihydro-3-oxo-1H-2-benzopyranyl; 3,4-dihydro-2-oxo-2H-1-benzopyranyl; 4-oxo-4H-1-benzopyranyl; 2-oxo-2H-1-benzopyranyl; 2,3,4,5-tetrahydro-5-oxo-1-benzoxepinyl; 2,3,4,5-tetrahydro-2-oxo-1-benzoxepinyl; 2,3-dihydro-1,3-dioxo-1H-isoindolyl; 1,2,3,4-tetrahydro-1,3-dioxoisoquinolinyl; 3,4-dihydro-2,4-dioxo-2H-1,3-benzoxazinyl; 2-oxo-1,3-benzodioxyl; 2,3-dihydro-1,1,3-trioxo-1,2-benzisothiazolyl; 9H-fluorenyl; azulenyl; and thiazolo[2,3-c]-1,2,4-triazolyl; each group substituted with $R^9$ and optionally substituted with one or more $R^{10}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; cyano; $CO_2(C_1$–$C_6$ alkyl); $NH(C_1$–$C_6$ alkyl); $N(C_1$–$C_6$ alkyl)$_2$; $SiR^{22}R^{23}R^{24}$; or $GeR^{22}R^{23}R^{24}$; or $R^9$ is $C_3$–$C_6$ cycloalkyl, phenyl, phenoxy, pyridinyl, pyridinyloxy, pyrimidinyl, or pyrimidinyloxy, each optionally substituted with one of $R^{11}$, $R^{12}$, or both $R^{11}$ and $R^{12}$; and $R^{30}$ is $C_3$–$C_6$ cycloalkyl.

Preferred 2. Compounds of Preferred I wherein:

Z is selected from the group phenyl; pyridinyl; pyrimidinyl; and naphthalenyl; each group substituted with $R^9$ and optionally substituted with one or more $R^{10}$; and $R^7$ is H; $C_1$–$C_6$ alkyl; $C_1$–$C_6$ haloalkyl; $C_1$–$C_6$ alkoxy; $C_1$–$C_6$ alkylthio; $C_2$–$C_6$ alkenyl; $C_2$–$C_6$ alkynyl; cyclopropyl; halogen; or cyano.

Preferred 3. Compounds of Preferred 2 wherein:

A is O; N; NR5; or $CR^{14}$;

X is $OR^1$;

$R^1$ is $C_1$–$C_3$ alkyl;

$R^2$ is H or $C_1$–$C_2$ alkyl;

Y is —$CH_2S$—$C(R^7)$=N—; —CH=$CR^6$—$C(=W^1)$—$A^1$—; —$CH_2O$—N=$C(R^{31})$—; or —$(R^7)C$=N—$OCH(R^{30})$—;

$R^7$ is H; $C_1$–$C_3$ alkyl; $C_1$–$C_3$ haloalkyl; $C_1$–$C_3$ alkoxy; $C_1$–$C_3$ alkylthio; or cyclopropyl; and $R^{30}$ is cyclopropyl.

Preferred 4. Compounds of Preferred 3 wherein:

A is O or $NR^5$;

G is C; and

Y is —CH=$CR^6$—$C(=W^1)$—$A^1$—; or —$CH_2O$—N=$C(R^{31})$—.

Preferred 5. Compounds of Preferred 4 wherein:

$R^1$ is methyl; and $R^2$ is methyl.

Preferred 6. Compounds of Preferred 3 wherein:

A is N or $CR^{14}$;

G is N; and

Y is —CH=$CR^6$-$C(=W^1)$—$A^1$—; or —$CH_2O$—N=C($R^{31}$)—.

Preferred 7. Compounds of Preferred 6 wherein:

$R^1$ is methyl; and $R^2$ is methyl.

Most preferred are compounds of Preferred 3 selected from the group:

[[2-(1,5—dihydro-3-methoxy-1-methyl-5-oxo-4H-1,2,4-triazol-4-yl)phenyl]methyl] N-(4-chlorophenyl)propanimidothioate;

1,1-dimethylethyl 2-chloro-3-[2-(1,5-dihydro-3-methoxy-1-methyl-5-oxo-4H-1,2,4-triazol4-yl)phenyl]-2-propenoate;

S-methyl 3,4-dichloro-N-[[2-(1,5-dihydro-3-methoxy-1-methyl-5-oxo-4H-1,2,4-triazol-4-yl)phenyl]methoxy]benzenecarboximidothioate; and S-methyl N-[[2-(1,5-dihydro-3-methoxy-1-methyl-5-oxo-4H-1,2,4-triazol-4-yl)phenyl]methoxy]-3,5-bis(trifluoromethyl)benzenecarboximidothioate.

This invention also relates to fungicidal compositions comprising fungicidally effective amounts of the compounds of the invention and at least one of a surfactant, a solid diluent or a liquid diluent. The preferred compositions of the present invention are those which comprise the above preferred compounds.

This invention also relates to a method for controlling plant diseases caused by fungal plant pathogens comprising applying to the plant or portion thereof, or to the plant seed or seedling, a fungicidally effective amount of the compounds of the invention (e.g., as a composition described herein). The preferred methods of use are those involving the above preferred compounds.

Of note are embodiments where $R^2$ is H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_3$–$C_6$ cycloalkyl, $C_2$–$C_4$ alkylcarbonyl or $C_2$–$C_4$ alkoxycarbonyl; embodiments where Y is —$NR^{15}$—, —$C(=O)$—, —$CHR^{15}OC(=S)N(R^{15})$—, —$CHR^{15}O$—$N(R^{15})C(=O)N(R^{15})$—, —$CHR^{15}O$—N($R^{15}$)C(=S)N($R^{15}$)—, —$CHR^{15}O$—N=C($R^7$)$NR^{15}$—, —$CHR^{15}O$—N=C($R^7$)$OCH_2$—, —$CHR^5O$—N=C($R^7$)—N=N—, —$CHR^{15}O$—N=C($R^7$)—C(=O)—, —$CHR^{15}O$—N=C($R^7$)—C(=N—$A^2$—$Z^1$)—$A^1$—, —$CHR^{15}O$—N=C($R^7$)—C($R^7$)—50 N—$A^2$—$A^3$—, —$CHR^{15}O$—N=C(—C($R^7$)=N—$A^2$—$Z^1$)—, —$CHR^{15}S$—C($R^7$)=N—, —C($R^7$)=N—$NR^{15}$—, —CH=N—N=C($R^7$)—, —$CHR^{15}N(COCH_3)$—N=C($R^7$)—, —OC(=S)$NR^{15}$C(=O)—, —$CHR^6$—C(=$W^1$)—$A^1$—, —$CHR^6CHR^6$—C(=$W^1$)—$A^1$—, —$CR^6$=$CR^6$—C(=$W^1$)—$A^1$—, —C≡C—C(=$W^1$)—A —, —N=$CR^6$—C(=$W^1$)—$A^1$—, —CH(O$R^{26}$)—, —$CHR^{27}$—, —$CHR^6CHR^{28}$—, —$CHR^{28}CHR^6$—, —$CR^6$=$CR^{29}$—, —$CR^{29}$=$CR^6$—, —$CHR^{30}O$—, —$OCHR^{30}$—, —$CHR^{30}S(O)_n$—, —$S(O)_nCHR^{30}$—, —$CHR^{30}O$—N=C($R^7$)—, —$CHR^{15}O$—N=C($R^{31}$)—, —($R^7$)C=N—$OCH(R^{30})$—, —($R^{31}$)C=N—$OCH(R^{15})$—, —C($R^{31}$)=N—O—, —O—N=C($R^{31}$)—, —$CHR^{30}OC(=O)N(R^{15})$— or —$CHR^{15}OC(=O)N(R^{32})$—; embodiments where Y is —$NR^{15}$—, —C(=O)—, —$CHR^{15}OC(=S)N(R^{15})$—, —$CHR^{15}O$—$N(R^{15})C(=O)N(R^{15})$—, —$CHR^{15}O$—N($R^{15}$)C(=S)N($R^{15}$)—, —$CHR^{15}O$—N=C($R^7$)$NR^{15}$—, —$CHR^{15}O$—N=C($R^7$)$OCH_2$—, —$CHR^{15}O$—N=C($R^7$)—N=N—, —$CHR^{15}O$—N=C($R^7$)—C(=O)—, —$CHR^{15}S$—C($R^7$)=N—, —C($R^7$)=N—$NR^{15}$—, —CH=N—N=C($R^7$)—, —$CHR^{15}N(COCH_3)$—N=C($R^7$)—, —OC(=S)$NR^{15}$C(=O)—, —$CHR^6$—C(=$W^1$)—$A^1$—, —$CHR^6CHR^6$—C(=$W^1$)—$A^1$—, —$CR^6$=$CR^6$—C(=$W^1$)—$A^1$—, —C≡C—C(=$W^1$)—$A^1$—, —N=$CR^6$—C(=$W^1$)—$A^1$—, —CH(O$R^{26}$)—, —$CHR^{27}$—, —$CHR^6CHR^{28}$—, —$CHR^{28}CHR^6$—, —$CR^6$=$CR^{29}$—, —$CR^{29}$=$CR^6$—, —$CHR^{30}O$—, —$OCHR^{30}$—, —$CHR^{30}S(O)_n$—, —$S(O)_nCHR^{30}$—, —$CHR^{30}O$—N=C($R^7$)—, —$CHR^{15}O$—N=C($R^{31}$)—, —($R^7$)C=N—$OCH(R^{30})$—, —($R^{31}$)C=N—$OCH(R^{15})$—, —C($R^{31}$)=N—O—, —O—N=C($R^{31}$)—, —$CHR^{30}OC(=O)N(R^{15})$— or —CHR$^{15}$OC(=O)N(R$^{32}$)—; embodiments where R$^7$ is H, C$_1$–C$_6$ alkyl, C$_1$–C$_6$ haloalkyl, C$_1$–C$_6$ alkoxy, C$_1$–C$_6$ haloalkoxy, C$_1$–C$_6$ alkylthio, C$_1$–C$_6$ alkylsulfinyl, C$_1$–C$_6$ alkylsulfonyl, C$_1$–C$_6$ haloalkylthio, C$_1$–C$_6$ haloalkylsulfinyl, C$_1$–C$_6$ haloalkylsulfonyl, C$_2$–C$_6$ alkenyl, C$_2$–C$_6$ haloalkenyl, C$_2$–C$_6$ alkynyl, C$_2$–C$_6$ haloalkynyl, C$_3$–C$_6$ C$_2$–C$_4$ alkylcarbonyl, C$_2$–C$_4$ alkoxycarbonyl, halogen, cyano or morpholinyl; embodiments where Z is other than adamantyl substituted with R$^9$ and optionally substituted with one or more R$^{10}$; embodiments where Z is other than C$_3$–C$_8$ cycloalkenyl and adamantyl each substituted with R$^9$ and optionally substituted with one or more R$^{10}$; embodiments where, when Y and an R$^{10}$ are attached to adjacent atoms on Z and Y is —CH=N—N=C(R$^7$)—, —CHR$^{15}$N(COCH$_3$)—N=C(R$^7$)— or —CHR$^{30}$O—N=C(R$^7$)—, R$^7$ and said adjacently attached R$^{10}$ are taken together as —(CH$_2$)$_r$—J— such that J is attached to Z; embodiments where R$^{19}$, R$^{20}$, R$^{21}$, R$^{22}$, R$^{23}$, and R$^{24}$ are each independently C$_1$–C$_6$ alkyl, C$_1$–C$_4$ alkoxy or phenyl; embodiments where each R$^{25}$ is independently C$_1$–C$_4$ alkyl or phenyl; and embodiments where R$^3$ and R$^4$ are each independently halogen, cyano, nitro, C$_1$–C$_6$ alkyl, C$_1$–C$_6$ haloalkyl, C$_1$–C$_6$ alkoxy, C$_1$–C$_6$ haloalkoxy, C$_1$–C$_6$ alkylsulfonyl, C$_2$–C$_6$ alkylcarbonyl, C$_2$–C$_6$ alkoxycarbonyl, (C$_1$–C$_4$ alkyl)NHC(O), (C$_1$–C$_4$ alkyl)$_2$NC(O), benzoyl or phenylsulfonyl.

The compounds of Formula I can be prepared by one or more of the following methods and variations as described in Schemes 1–33. The definitions of E, A, G, W, X, R$^1$–R$^{32}$, Y, Z$^1$, W$^1$, A$^1$–A$^3$, Z, Q, J, m, n, p, r and s in the compounds of Formulae 1–58 below are as defined above in the Summary of the Invention. Compounds of Formulae Ia–Io are various subsets of the compounds of Formula I, and all substituents for Formulae Ia–Io are as defined above for Formula I.

One skilled in the art will recognize that some compounds of Formula I can exist in one or more tautomeric forms. For example, a compound of Formula I wherein R$^2$ is H may exist as tautomer Ia or Ib, or both Ia and Ib. The present invention comprises all tautomeric forms of compounds of Formula I.

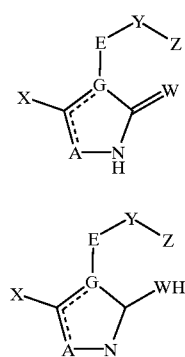

The compounds of Formula I can be prepared as described below in Procedures 1) to 5). Procedures 1) to 4) describe syntheses involving construction of the amide ring after the formation of the aryl moiety (E-Y-Z). Procedure 5) describes syntheses of the aryl moiety (E-Y-Z) with the amide ring already in place.

1) Alkylation Procedures

The compounds of Formula I are prepared by treating compounds of Formula I with an appropriate alkyl transfer reagent in an inert solvent with or without additional acidic or basic reagents or other reagents (Scheme 1). Suitable solvents are selected from the group consisting of polar aprotic solvents such as acetonitrile, dimethylformamide or dimethyl sulfoxide; ethers such as tetrahydrofuran, dimethoxyethane, or diethyl ether, ketones such as acetone or 2-butanone; hydrocarbons such as toluene or benzene; and halocarbons such as dichloromethane or chloroform.

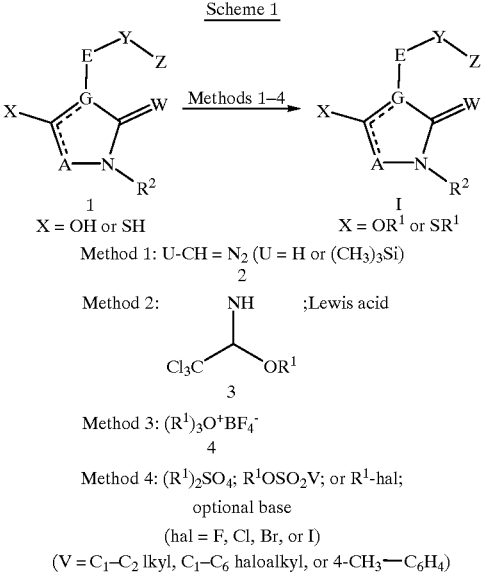

Scheme 1

For example, compounds of Formula I can be prepared by the action of diazoalkane reagents of Formula 2 such as diazomethane (U=H) or trimethylsilyldiazomethane (U=(CH$_3$)$_3$Si) on dicarbonyl compounds of Formula I (Method 1). Use of trimethylsilyldiazomethane requires a protic cosolvent such as methanol. For examples of these procedures, see *Chem. Pharm. Bull.*, (1984), 32, 3759.

As indicated in Method 2, compounds of Formula I can also be prepared by contacting carbonyl compounds of Formula I with alkyl trichloroacetimidates of Formula 3 and a Lewis acid catalyst. Suitable Lewis acids include trimethylsilyl triflate and tetrafluoroboric acid. The alkyl trichloroacetimidates can be prepared from the appropriate alcohol and trichloroacetonitrile as described in the literature (J. Dankimaier and H. Hönig, *Synth. Commun.*, (1990), 20, 203).

Compounds of Formula I can also be prepared from compounds of Formula I by treatment with a trialkyloxonium tetrafluoroborate (i.e., Meerwein's salt) of Formula 4 (Method 3). The use of trialkyloxonium salts as powerful alkylating agents is well known in the art (see U. Schöllkopf, U. Groth, C. Deng, *Angew. Chem., Int. Ed. Engl.*, (1981), 20, 798).

Other alkylating agents which can convert carbonyl compounds of Formula I to compounds of Formula I are dialkyl sulfates such as dimethyl sulfate, haloalkyl sulfonates such as methyl trifluoromethanesulfonate, and alkyl halides such as iodomethane and propargyl bromide (Method 4). These alkylations can be conducted with or without additional base. Appropriate bases include alkali metal alkoxides such as potassium tert-butoxide, inorganic bases such as sodium hydride and potassium carbonate, or tertiary amines such as triethylamine, pyridine, 1,8-diazabicyclo[5.4.0]undec-7-ene (DBU), and triethylenediamine. See R. E. Benson, T. L. Cairns, *J. Am. Chem. Soc.*, (1948), 70, 2115 for alkylation examples using agents of this type.

Compounds of Formula 1a (compounds of Formula 1 wherein G=C, W=O and X=OH) can be prepared by condensation of malonates or malonate derivatives of Formula 5 with an ambident nucleophile of Formula 6 (Scheme 2). The nucleophiles of Formula 6 are N-substituted hydroxylamines (HO—NHR$^2$) and substituted hydrazines (HN(R$^5$)—NHR$^2$). Examples of such nucleophiles are N-methylhydroxylamine and methylhydrazine. The malonate esters of Formula 5 can be prepared by methods described hereinafter. The esters of Formula 5 can also be activated by first hydrolyzing the ester to form the corresponding carboxylic acid, and then converting the acid into the acid chloride (T=Cl) using thionyl chloride or oxalyl chloride, or into the acyl imidazole (T=1-imidazolyl) by treating with 1,1'-carbonyldiirnidazole. Compounds of Formula 1 aa can be prepared by reaction of nitrile esters of Formula 5b with ambident nucleophiles of Formula 6. See M. Scobie and G. Tennant, *J. Chem. Soc., Chem. Comm.*, (1994), 2451. Alkylation of 1aa with alkyl halides in the presence of base provides compounds of Formula 1ab. Alternatively, treatment of 1aa with alkylarnines or alkoxyamines provides compounds of Formula 1ab.

Esters of Formula 5a can be prepared from copper (I)-catalyzed reaction of malonate esters of Formula 7 with substituted aryl halides of Formula 8 according to methods adapted from A. Osuka, T. Kobayashi and H. Suzuki, *Synthesis*, (1983), 67 and M. S. Malamas, T. C. Hohman, and J. Millen, *J. Med. Chem.*, 1994, 37, 2043–2058, and illustrated in Scheme 3. Procedures to prepare compounds of Formula 8 are described below (see Scheme 32).

Malonate esters of Formula 5a can also be prepared from diester carboxylic acids of Formula 5c after modification of the carboxylic acid functional group to the appropriate Y and Z group. A copper (I)-catalyzed coupling of malonates of Formula 7 with orthobromocarboxylic acids of Formula 8a (see A. Bruggink, A. McKillop, Tetrahedron, (1975), 31, 2607) can be used to prepare compounds of Formula 5c as shown in Scheme 3. Methods to prepare compounds of Formula 8a are common in the art (see P. Beak, V. Snieckus, *Acc. Chem. Res.*, (1982), 15, 306 and *Org. React.*, (1979), 26, 1 and references therein).

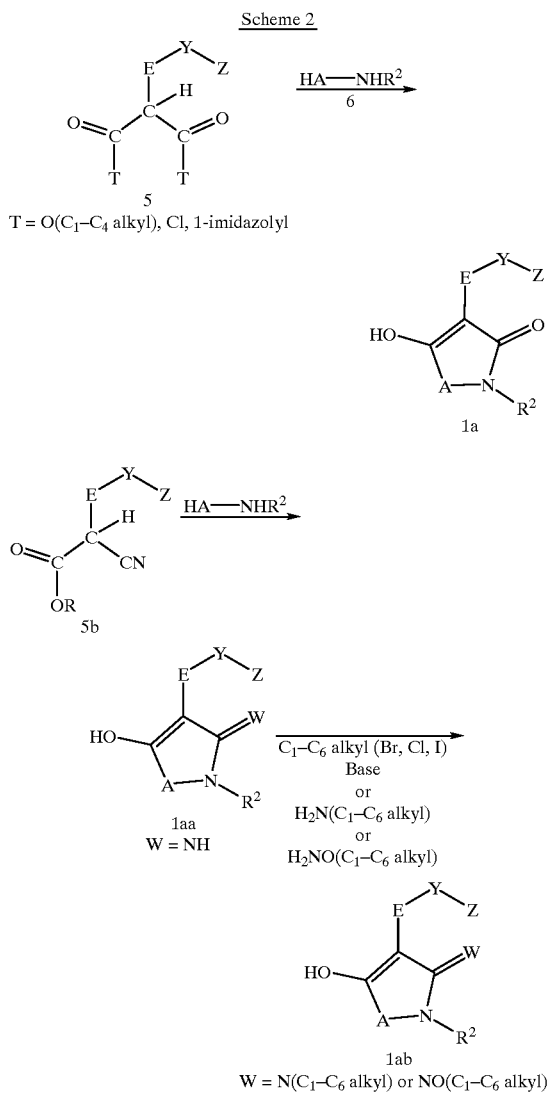

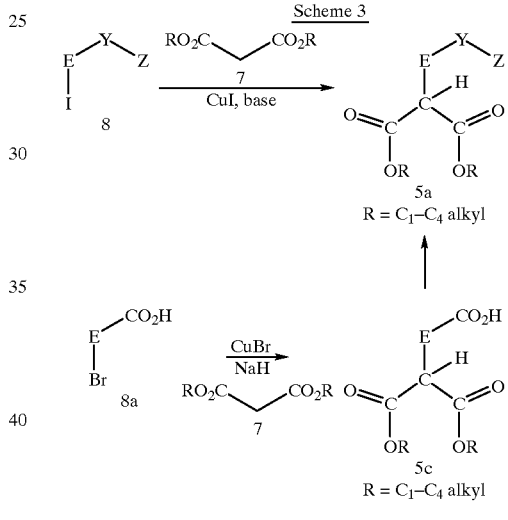

Additionally, the malonate esters of Formula 5a can be prepared by treating aryl acetic acid esters of Formula 9 with a dialkyl carbonate or alkyl chloroformate in the presence of a suitable base such as, but not limited to, sodium metal or sodium hydride (Scheme 4). For example, see *J. Am. Chem. Soc.*, (1928), 50, 2758. Nitrile esters of Formula 5b can be prepared similarly from compounds of Formula 10.

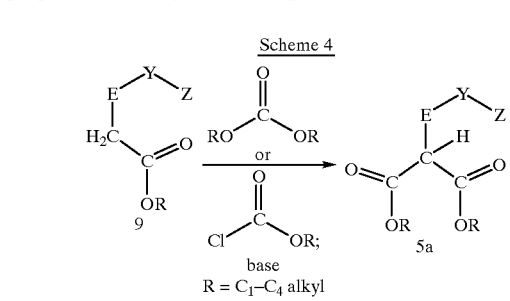

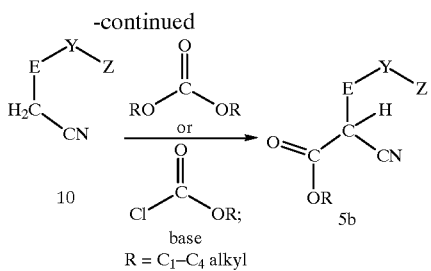

Esters of Formula 9 can be prepared from acid-catalyzed alcoholysis of aryl acetonitriles of Formula 10 or esterification of aryl acetic acids of Formula 11 as illustrated in Scheme 5 (see *Org. Synth.*, Coll. Vol. I, (1941), 270).

Additionally, esters of formula 9 can be prepared by palladium (0)-catalyzed cross coupling reaction of aryl iodides of Formula 8 with a Reformatsky reagent or an alkoxy(trialkylstannyl)acetylene followed by hydration (Scheme 5). For example, see T. Sakamoto, A. Yasuhara, Y. Kondo, H. Yamanaka, Synlett., (1992), 502, and J. F. Fauvarque, A. Jutard, *J. Organometal. Chem.*, (1977), 132, C17.

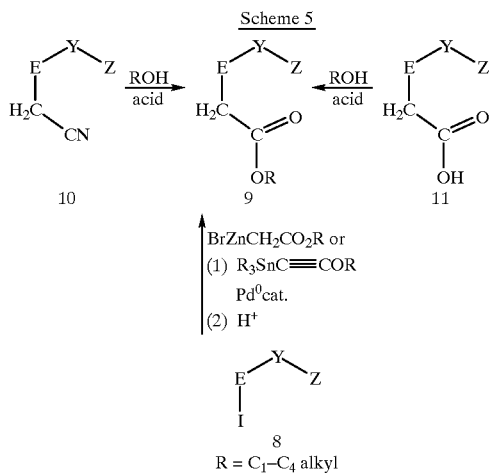

Aryl acetic acid esters of Formula 9a can also be prepared by copper (I)-catalyzed condensation of aryl halides of Formula 12 with compounds of Formula 13 as described in EP-A-307,103 and illustrated below in Scheme 6.

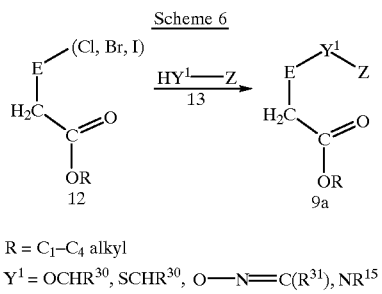

R = $C_1$–$C_4$ alkyl
$Y^1$ = $OCHR^{30}$, $SCHR^{30}$, O—N=$C(R^{31})$, $NR^{15}$ Some esters of Formula 9 (Formula 9b) can also be prepared by forming the $Y^2$ bridge using conventional nucleophilic substitution chemistry (Scheme 7). Displacement of an appropriate leaving group (Lg) in electrophiles of Formula 15 or 16 with a nucleophilic ester of Formula 14 affords compounds of Formula 9b. A base, for example sodium hydride, is used to generate the corresponding alkoxide or thioalkoxide of the compound of Formula 14.

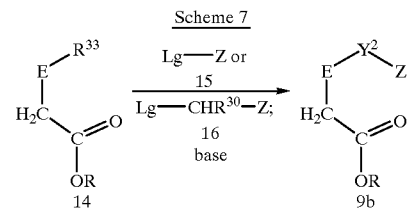

R = $C_1$–$C_4$ alkyl
$R^{33}$ = OH, SH, $CHR^{30}OH$, $CHR^{30}SH$, $NHR^{15}$
$Y^2$ = $OCHR^{30}$, $SCHR^{30}$, $CHR^{30}O$, $CHR^{30}S$, $NR^{15}$
Lg = Br, Cl, I, $OSO_2CH_3$, $OSO_2$(4-Me-Ph)

Some esters of Formula 9 (Formula 9e) can also be prepared by forming the $Y^3$ bridge from substituted hydroxylamine 9d and carbonyl compounds 14a. The hydroxylamine 9d is in turn prepared from esters 9c. This method has been described in EP-A-600,835 and illustrated in Scheme 8.

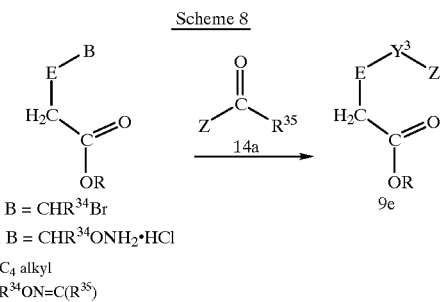

9c B = $CHR^{34}Br$
9d B = $CHR^{34}ONH_2$·HCl

R = $C_1$–$C_4$ alkyl
$Y^3$ = $CHR^{34}ON=C(R^{35})$
$R^{34}$ and $R^{35}$ are $R^{15}$ and $R^{31}$, respectively, or
$R^{34}$ and $R^{35}$ are $R^{30}$ and $R^7$, respectively 2) Displacement and Conjugate Addition/Elimination Procedures Compounds of Formula I can also be prepared by reaction of Formula 17 compounds with alkali metal alkoxides ($R^1O^-M^+$) or alkali metal thioalkoxides ($R^1S^-M^+$) in a suitable solvent (Scheme 9). The leaving group $Lg^1$ in the amides of Formula 17 are any group known in the art to undergo a displacement reaction of this type. Examples of suitable leaving groups include chlorine, bromine, and sulfonyl and sulfonate groups. Examples of suitable inert solvents are dimethylformamide or dimethyl sulfoxide.

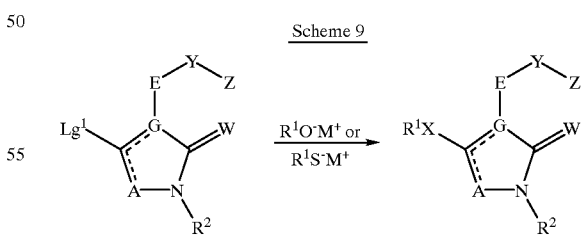

$Lg^1$ = Cl, Br, —$SO_2V$, or —$OSO_2V$
V = $C_1$-$C_6$ alkyl, $C_1$-$C_6$ haloalkyl, or 4-$CH_3$—$C_6H_4$
M = K or Na Compounds of Formula 17a can be prepared from compounds of Formula 1b (compounds of Formula 1 wherein X is OH) by reaction with halogenating agents such as thionyl chloride or phosphorus oxybromide to form the corresponding β-halo-substituted derivatives (Scheme 10). Alternatively, compounds of Formula 1b can be treated with an alkylsulfonyl halide or haloalkylsulfonyl anhydride, such as methanesulfonyl chloride, p-toluenesulfonyl chloride, and trifluoromethanesulfonyl anhydride, to form the corresponding β-alkylsulfonate of Formula 17a. The reaction with the sulfonyl halides may be performed in the presence of a suitable base (e.g., triethylamine).

Scheme 10

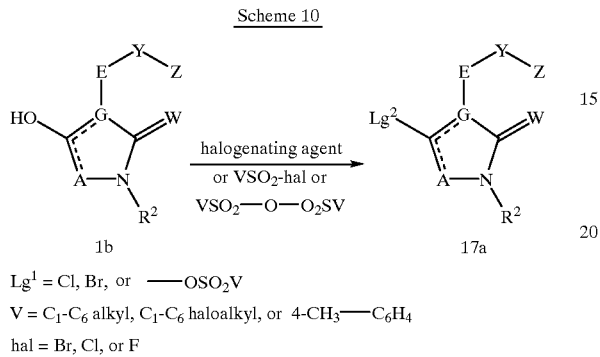

$Lg^1$ = Cl, Br, or ——$OSO_2V$
V = $C_1$-$C_6$ alkyl, $C_1$-$C_6$ haloalkyl, or 4-$CH_3$——$C_6H_4$
hal = Br, Cl, or F As illustrated in Scheme 11, sulfonyl compounds of Formula 17b can be prepared by oxidation of the corresponding thio compound of Formula 18 using well-known methods for the oxidation of sulfur (see Schrenk, K. In *The Chemistry of Sulphones and Sulphoxides*; Patai, S. et al., Eds.; Wiley: New York, 1988). Suitable oxidizing reagents include meta-chloro-peroxybenzoic acid, hydrogen peroxide and Oxone® ($KHSO_5$).

Scheme 11

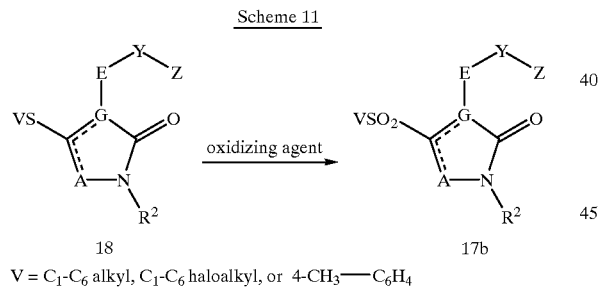

V = $C_1$-$C_6$ alkyl, $C_1$-$C_6$ haloalkyl, or 4-$CH_3$——$C_6H_4$

Alternatively, halo-compounds of Formula 17c (compounds of Formula 17a wherein A=N, G=N, and W=O) can be prepared from hydrazides of Formula 19 as illustrated in Scheme 12. When $R^{36}$=C(=S)S($C_1$-$C_4$ alkyl), the diacyl compound of Formula 19 is treated with excess thionyl halide, for example excess thionyl chloride. The product formed first is the ring-closed compound of Formula 20 which can be isolated or converted in situ to the compound of Formula 17c; see P. Molina, A. Tárraga, A. Espinosa, *Synthesis*, (1989), 923 for a description of this process.

Alternatively, when $R^{36}$=$R^2$ as defined above, the hydrazide of Formula 19 is cyclized with phosgene to form the cyclic urea of Formula 17c wherein hal=Cl. This procedure is described in detail in *J. Org. Chem.*, (1989), 54, 1048.

Scheme 12

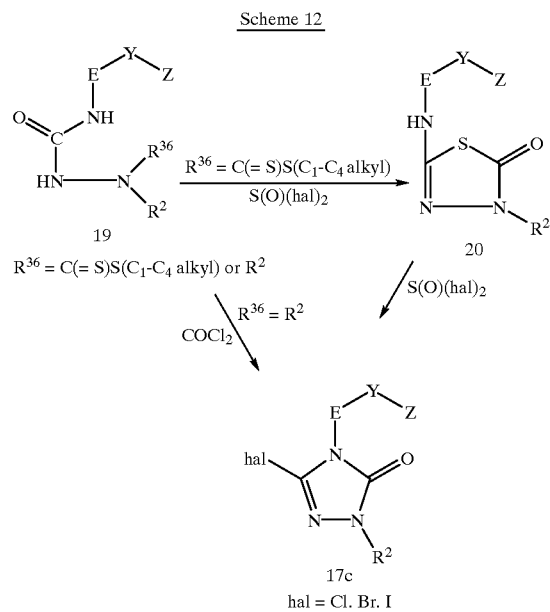

hal = Cl. Br. I

The hydrazides of Formula 19 can be prepared as illustrated in Scheme 13. Condensation of the isocyanate of Formula 21 with the hydrazine of Formula $H_2NNR^2R^{36}$ in an inert solvent such as tetrahydrofuran affords the hydrazide.

Scheme 13

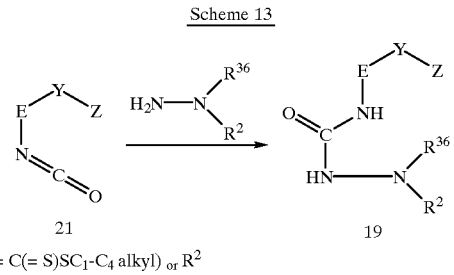

$R^{36}$ = C(=S)S$C_1$-$C_4$ alkyl) or $R^2$

3) Conjugate Addition/Cyclization Procedures

In addition to the methods disclosed above, compounds of Formula I wherein X=$SR^1$ and G=C (Formula Ic) can be prepared by treating a ketenedithioacetal of Formula 22 with an ambident nucleophile of Formula 6 (Scheme 14). The nucleophiles of Formula 6 are described above.

Scheme 14

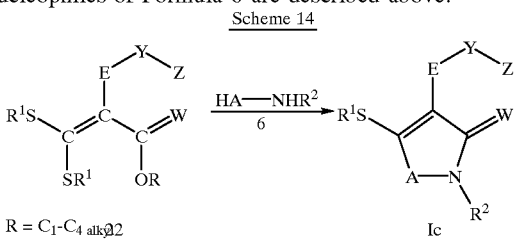

R = $C_1$-$C_4$ alkyl 22

Ketene dithioacetals of Formula 22a or 22b can be prepared by condensing arylacetic acid esters of Formula 9 or amides of Formula 9a, respectively, with carbon disulfide in the presence of a suitable base, followed by reaction with two equivalents of an $R^1$-halide, such as iodomethane or propargyl bromide (Scheme 15). Conversion of 22b to 22c can be accomplished by reaction with trialkyl tetrafluoroborates.

Scheme 15

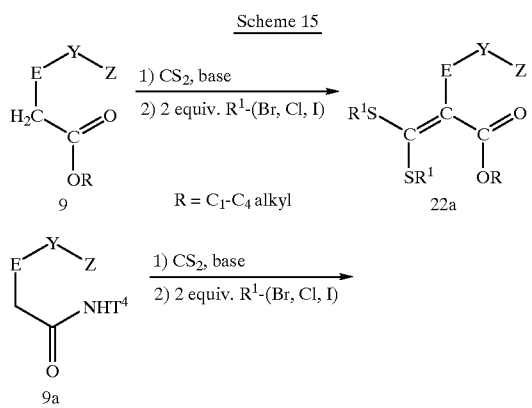

$T^4$ = H, $C_1$-$C_6$ alkyl, $C_1$-$C_6$ alkoxy

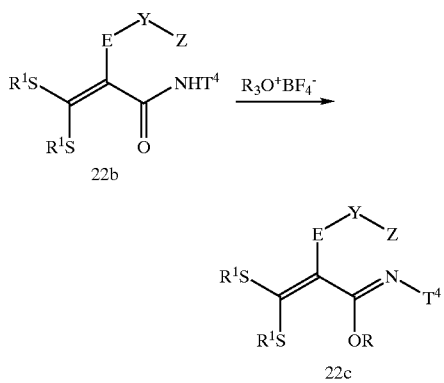

Compounds of Formula 1d (compounds of Formula 1 wherein A=N, G=N) can be prepared by condensation of N-amino-ureas of Formula 23 with a carbonylating agent of Formula 24 (Scheme 16). The carbonylating agents of Formula 24 are carbonyl or thiocarbonyl transfer reagents such as phosgene, thiophosgene, diphosgene (ClC(=O)OCCl$_3$), triphosgene (Cl$_3$COC(=O)OCCl$_3$), N,N'-carbonyldiimidazole, N,N'-thiocarbonyldiimidazole, and 1,1'-carbonyldi(1,2,4-triazole). Alternatively, the compounds of Formula 24 can be alkyl chloroformates or dialkyl carbonates. Some of these carbonylating reactions may require the addition of a base to effect reaction. Appropriate bases include alkali metal alkoxides such as potassium tert-butoxide, inorganic bases such as sodium hydride and potassium carbonate, tertiary amines such as triethylamine and triethylenediaamine, pyridine, or 1,8-diazabicyclo[5.4.0]undec-7-ene (DBU). Suitable solvents include polar aprotic solvents such as acetonitrile, dimethylformamide, or dimethyl sulfoxide; ethers such as tetrahydrofuran, dimethoxyethane, or diethyl ether; ketones such as acetone or 2-butanone; hydrocarbons such as toluene or benzene; or halocarbons such as dichloromethane or chloroform. The reaction temperature can vary between 0° C. and 150° C. and the reaction time can be from 1 to 72 hours depending on the choice of base, solvent, temperature, and substrates.

Scheme 16

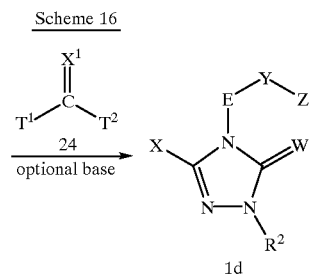

$T^1$ and $T^2$ are independently Cl, OCCl$_3$, O($C_1$-$C_4$ alkyl), 1-imidazolyl, 1,2,4-triazolyl X = OH or SH $X^1$ = O or S N-Amino-ureas of Formula 23 can be prepared as illustrated in Scheme 17. Treatment of an arylamine of Formula 25 with phosgene, thiophosgene, N,N'-carbonyldiimnidazole, or N,N'-thiocarbonyldiimidazole produces the isocyanate or isothiocyanate of Formula 26. A base can be added for reactions with phosgene or thiophosgene. Isocyanates of Formula 26 can also be prepared by heating acylazides of Formula 25a in a solvent such as toluene or benzene (Curtius rearrangement). The corresponding acylazides can be prepared using well known methods in the art (see March, J., *Advanced Organic Chemistry*; 3rd Edition, John Wiley: New York, (1985), pp 428, 637 and also *Chem. Pharm. Bull* (1977), 25 (7) 1651, and references therein. Subsequent treatment of the iso(thio)cyanate with an $R^2$-substituted hydrazine produces the N-amino-urea of Formula 23.

Scheme 17

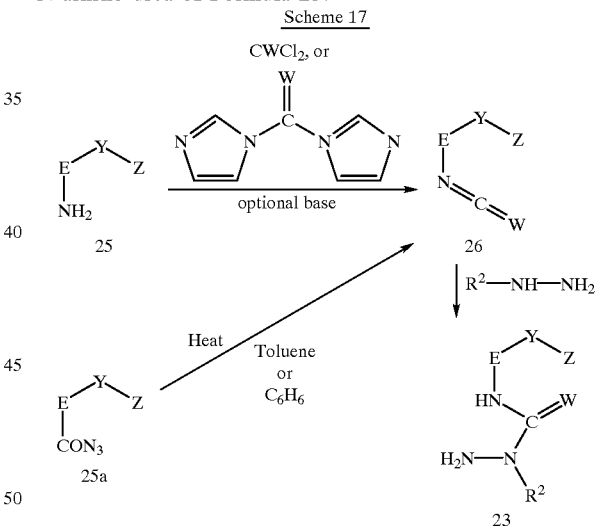

Compounds of Formula 1e (compounds of Formula 1 wherein A=CR$^5$, G=N, and X=O) can be prepared by either method illustrated in Scheme 18. Ureas of Formula 27 are reacted with activated 2-halocarboxylic acid derivatives such as 2-halocarboxylic acid chlorides, 2-halocarboxylic acid esters or 2-haloacyl imidazoles. The initial acylation on the arylamino nitrogen is followed by an intramolecular displacement of the 2-halo group to effect cyclization. Base may be added to accelerate the acylation and/or the subsequent cyclization. Suitable bases include triethylamine and sodium hydride. Alternatively, Formula 1e compounds can be prepared by reaction of Formula 26 iso(thio)cyanates or Formula 26a carbodiimides with Formula 28a esters. As described above, base may be added to accelerate the reaction and subsequent cyclization to Formula 1e compounds. Carbodiimides 26a can be prepared as shown in Scheme 18, starting with compounds of Formula 26.

Scheme 18

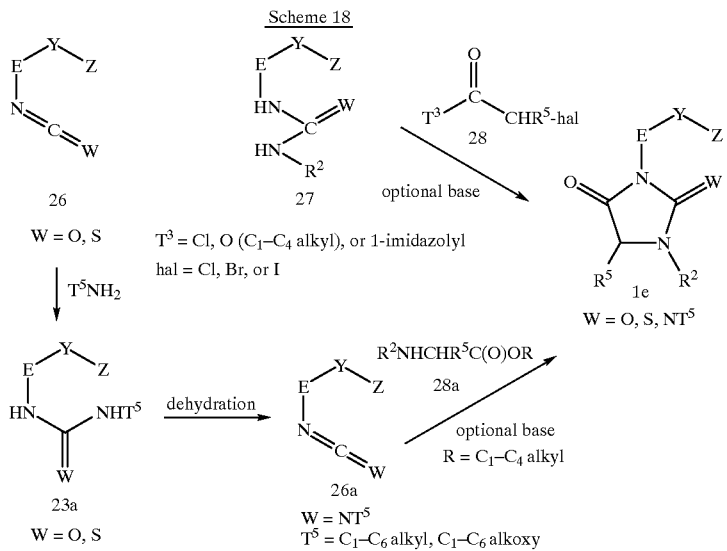

The thioureas or amidines of Formula 27 can be prepared by either of the methods illustrated in Scheme 19. The arylamine of Formula 25 can be contacted with an isocyanate or isothiocyanate of Formula $R^2N=C=W$ as described above. Alternatively, an iso(thio)cyanate of Formula 26 or carbodiimide of Formula 26a can be condensed with an amine of Formula $R^2$—$NH_2$ to form the urea or amidine. The arylamine and iso(thio)cyanates of Formulae 25 and 26, respectively, are commercially available or prepared by well-known methods. For example, isothiocyanates can be prepared by methods described in *J. Heterocycl. Chem.*, (1990), 27, 407. Isocyanates can be prepared as described in March, *J. Advanced Organic Chemistry*; 3rd ed., John Wiley: New York, (1985), pp 944, 1166 and also in *Synthetic Communications*, (1993), 23(3), 335 and references therein. For methods describing the preparation of arylamines of Formula 25 that are not commercially available, see M. S. Gibson In *The Chemistry of the Amino Group*; Patai, S., Ed.; Interscience Publishers, 1968; p 37 and *Tetrahedron Lett.* (1982), 23(7), 699 and references therein.

Scheme 19

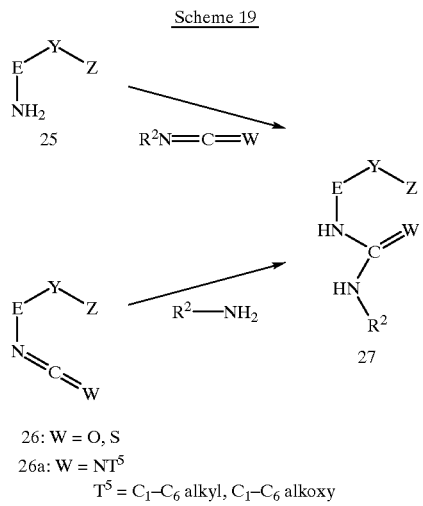

4) Thionation Procedures

Compounds of Formula Ie, compounds of Formula I wherein W=S, can be prepared by treating compounds of Formula Id (I wherein W=O) with thionating reagents such as $P_2S_5$ or Lawesson's reagent (2,4-bis(4-methoxyphenyl)-1,3-dithia-2,4-diphosphetane-2,4-disulfide) as illustrated in Scheme 20 (see *Bull. Soc. Chim. Beig.*, (1978), 87, 229; and *Tetrahedron Lett.*, (1983), 24, 3815).

Scheme 20

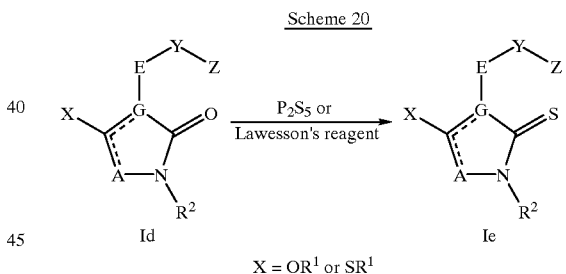

Reaction of compounds of Formula Iea with an alkyl halide in the presence of base provides compounds of Formula Ieb, which can be reacted with compounds of Formula $T^5NH_2$ and then alkylated with $R^2$-(Br, Cl, or I) to provide compounds of Formula Iec.

Scheme 20a

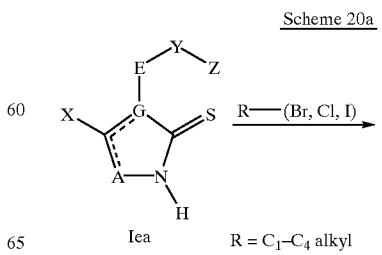

-continued

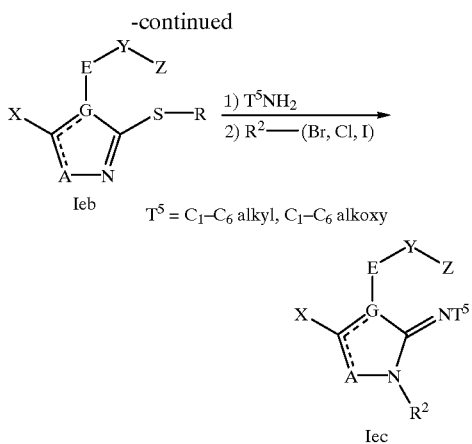

5) Aryl Moiety (E-Y-Z) Synthesis Procedures

Compounds of Formula If (compounds of Formula I wherein Y is $CHR^{30}O$, $CHR^{30}S$, $CHR^{15}O—N=C(R^{31})$ or $CHR^{30}O—N=C(R^7)$) can be prepared by contacting halides of Formula 29 with various nucleophiles (Scheme 21). The appropriate alcohol or thiol is treated with a base, for example sodium hydride, to form the corresponding alkoxide or thioalkoxide which acts as the nucleophile.

Some aryl halides of Formula 29 can be prepared by radical halogenation of the corresponding alkyl compound (i.e., H instead of halogen in Formula 29), or by acidic cleavage of the corresponding methylether (i.e., OMe instead of halogen in Formula 29). Other aryl halides of Formula 29 can be prepared from the appropriate alcohols of Formula 30 by well known halogenation methods in the art (see Carey, F. A.; Sundberg, R. J. *Advanced Organic Chemistry*; 3rd ed., Part B, Plenum: New York, (1990), p 122).

Compounds of Formula I wherein Y is $CR^6=CR^{29}$, $CR^{29}=CR^6$, $CHR^6CHR^{28}$ or $CHR^{28}CHR^6$ (Formula Ig and Ih, respectively) can be prepared as illustrated in Scheme 22. Treatment of the halides of Formula 29 with triphenylphosphine or a trialkylphosphite produces the corresponding phosphonium salt (Formula 31) or phosphonate (Formula 32), respectively. Condensation of the phosphorus compound with a base and a carbonyl compound of Formula $Z(R^{40})C=O$ affords the olefin of Formula Ig.

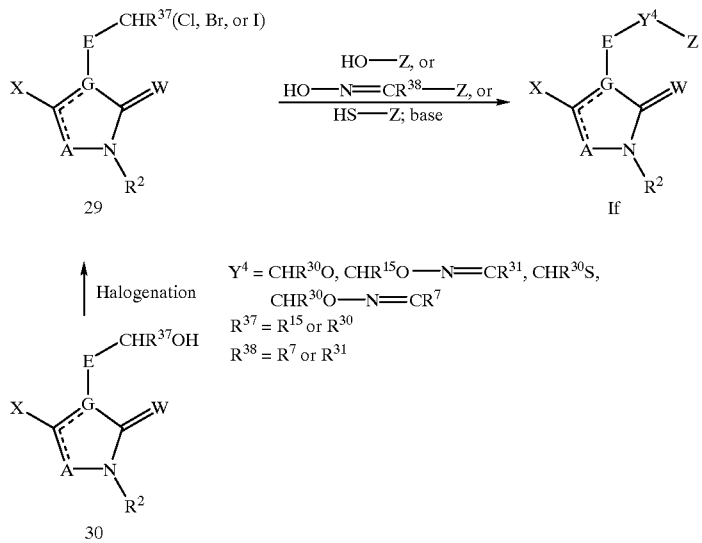

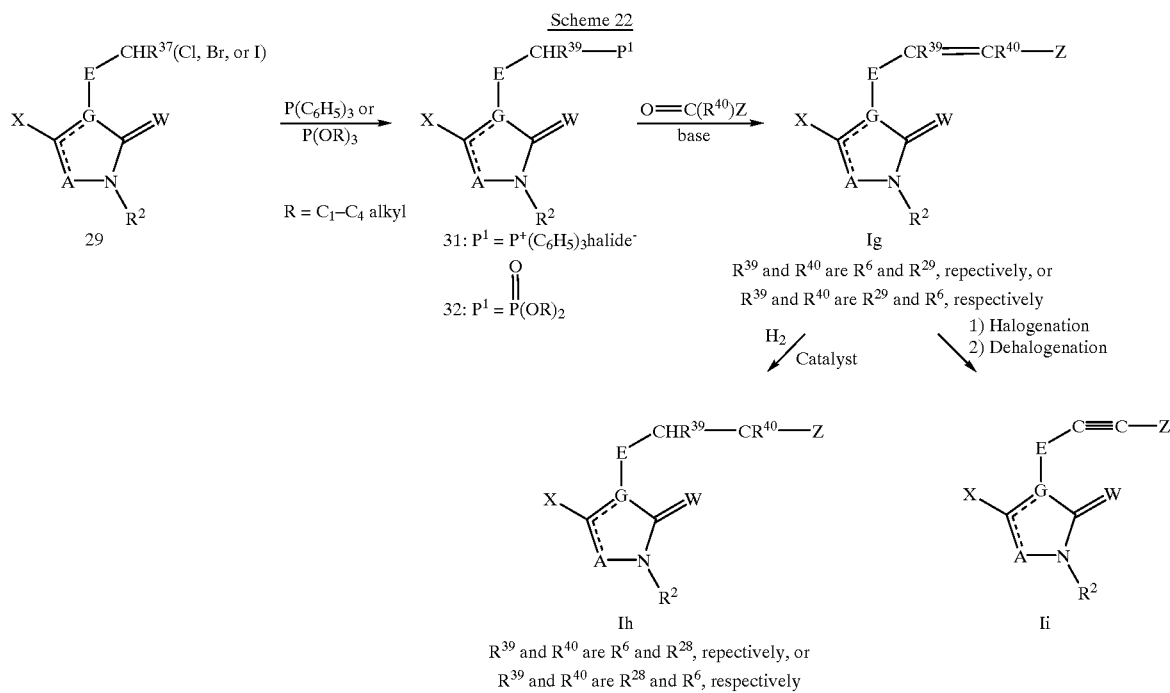

The olefins of Formula Ig can be converted to the saturated compounds of Formula Ih by hydrogenation over a metal catalyst such as palladium on carbon as is well-known in the art (Rylander, *Catalytic Hydrogenation in Organic Synthesis*; Academic: New York, 1979).

Formula Ii alkynes can be prepared by halogenation/dehalogenation of Formula Ig olefins using procedures well-known in the art (March, *J. Advanced Organic Chemistry*; 3rd ed., John Wiley: New York, (1985), p 924). Additionally, Formula Ii alkynes can be prepared by well-known reaction of aryl halides with alkyne derivatives in the presence of catalysts such as nickel or palladium (see *J. Organomet. Chem.*, (1975), 93, 253–257).

The olefin of Formula Ig can also be prepared by reversing the reactivity of the reactants in the Wittig or Horner-Emmons condensation. For example, 2-alkylaryl derivatives of Formula 33 can be converted into the corresponding dibromo-compound of Formula 34 as illustrated in Scheme 23 (see Synthesis, (1988), 330). The dibromo-compound can be hydrolyzed to the carbonyl compound of Formula 35, which in turn can be condensed with a phosphorus-containing nucleophile of Formula 36 or 37 to afford the olefin of Formula Ig. Carbonyl compounds of Formula 35 can also be prepared by oxidation of halides of Formula 29 in Scheme 22 (see *Tetrahedron Lett.* (1990), 31, 4825 and *Bull. Chem. Soc. Jpn*, (1981), 54, 2221 and references therein). Additionally, compounds of Formula 35 can be prepared by oxidation of the corresponding alcohols of Formula 30.

Vinylhalides of Formula Ij can be prepared by reacting phosphorus reagents of Formulae 37a or 37b with carbonyl compounds of Formula 35 (Scheme 23). The preparations of halides of Formula 37a from the appropriate diethylphosphonoacetate are described by McKenna and Khawli in *J. Org. Chem.*, (1986), 51, 5467. The thiono esters of Formula 37b can be prepared from esters of Formula 37a by converting the carbonyl oxygen of the ester to a thiocarbonyl (see *Chem. Rev.*, (1984), 84, 17 and *Tetrahedron Lett.*, (1984), 25, 2639).

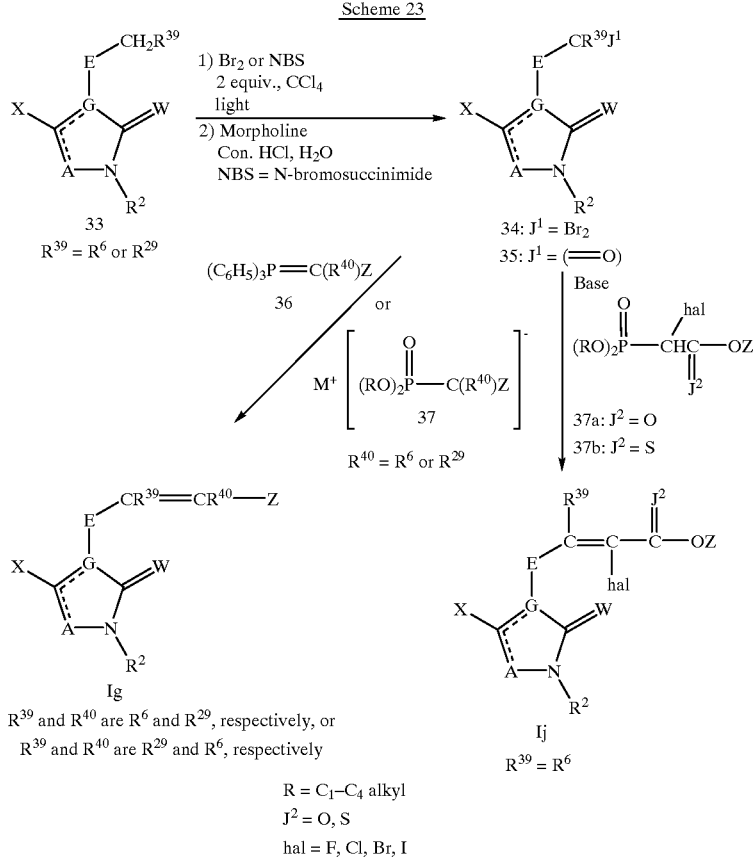

Oximes of Formula Ik (Formula I wherein Y is C($R^{31}$)=N—O) can be prepared from carbonyl compounds of Formula 38 by condensation with hydroxylamine, followed by O-alkylation with electrophiles of Formula Z—(Cl, Br, or I) (Scheme 24). Alternatively, the O-substituted hydroxylamine can be condensed with the carbonyl compound of Formula 38 to yield oximes of Formula Ik directly.

Carbamates of Formula Il can be prepared by reacting aryl alcohols of Formula 30 with isothiocyanates of Formula 39 (Scheme 25). A base such as triethylamine can be added to catalyze the reaction. As shown, carbamates of Formula Il can be further alkylated to provide the carbamates of Formula Im.

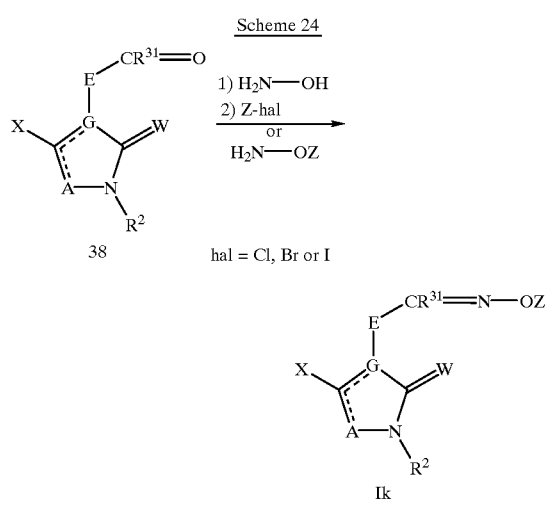

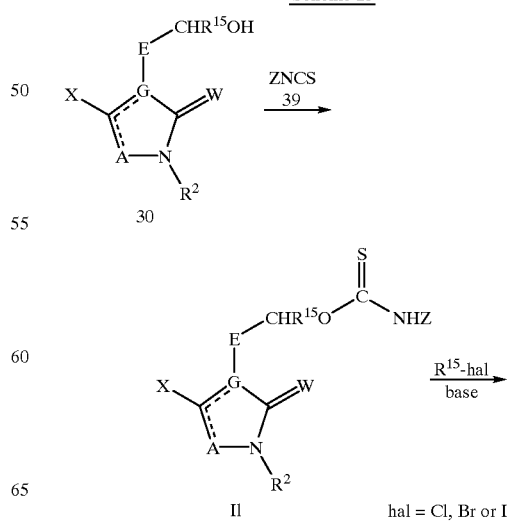

31
-continued

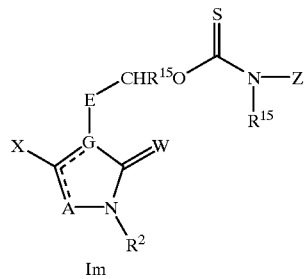

Im

Compounds of Formula I wherein Y is —CHR¹⁵O— N═C(R⁷)—C(═N—A²—Z¹)—A¹—, —CHR¹⁵O—N═C (R⁷)—C(R⁷)═N—A²—A³— or —CHR¹⁵O—N═C(—C (R⁷)═N—A²—Z¹)— can be prepared by methods known in the art or obvious modifications (see, for example, WO 95/18789, WO 95/21153, and references therein) together with the methods disclosed herein.

Compounds of Formula I wherein Y is —CHR¹⁵OC(═O) O—, —CHR¹⁵OC(═S)O—, —CHR¹⁵OC(═O)S—, —CHR¹⁵OC(═S)S—, —CHR¹⁵SC(═O)N(R¹⁵)—, —CHR¹⁵SC(═S)N(R¹⁵)—, —CHR¹⁵SC(═O)O—, —CHR¹⁵SC(═S)O—, —CHR¹⁵SC(═O)S—, —CHR¹⁵SC(═S)S—, —CHR¹⁵SC(═NR¹⁵)S— or —CHR¹⁵N(R¹⁵)C(═O)N(R¹⁵)— can be prepared by methods known in the art or obvious modifications (see, for example, U.S. Pat. No. 5,416,110, EP 656,351-A1 and references therein) together with the methods disclosed herein.

The compounds of the present invention are prepared by combinations of reactions as illustrated in the Schemes 1–25 in which Z is a moiety as described in the summary. Preparation of the compounds containing the radical Z as described in the summary, substituted with L (defined as any group attached to Z as depicted in each of the individual schemes) can be accomplished by one skilled in the art by the appropriate combination of reagents and reaction sequences for a particular Z-L. Such reaction sequences can be developed based on known reactions available in the chemical art. For a general reference, see March, *J. Advanced Organic Chemistry*; 3rd ed., John Wiley: New York, (1985) and references therein. See the following paragraphs for some examples of how,L is defined in individual schemes, and the preparation of representative Z-L examples.

Compounds of Formula 41 in Scheme 26 can be prepared from compounds of Formula 40 by reaction with hydroxylarnine or hydroxylarnine salts. See Sandler and Karo, "Organic Functional Group Preparations," Vol. 3 Academic Press, New York, (1972) 372–381 for a review of methods. Compounds of Formula 41 correspond to compounds of Formula 13 in Scheme 6 when Y¹=O—N═C(R³¹) and in Scheme 21, reagent HO—N═CR³¹.

Scheme 26

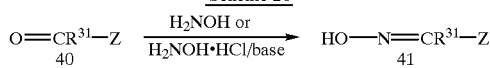

Compounds of Formula 40 can be prepared from compounds of Formula 39a (Scheme 27) by Friedel-Crafts acylation with compounds of Formula 42. (See Olah, G. "Friedel-Crafts and Related Reactions," Interscience, New York (1963–1964) for a general review). Compounds of Formula 40 may also be prepared by reaction of acyl halides, anhydrides, esters, or amides of Formula 45 with organometallic reagents of Formula 44. (See March, *J. Advanced Organic Chemistry*; 3rd ed., John Wiley: New York, (1985),

32 pp 433–435 and references therein.) The organometallic compounds of Formula 44 may be prepared by reductive metallation or halogen-metal exchange of a halogen-containing compound of Formula 43 using, for example, magnesium or an organolithium reagent, or by deprotonation of compounds of Formula 39a using a strong base such as a lithioarnide or an organolithium reagent, followed by transmetallation. Compound 40 corresponds to Compound 14a in Scheme 8, while compound 40a corresponds to O═C(R⁴⁰)Z in Scheme 22.

Scheme 27

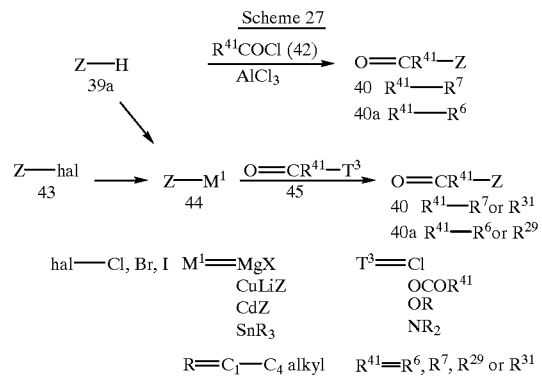

Compounds of Formula 43 may be prepared by reaction of compounds of Formula 39a (Scheme 28) with, for example, bromine or chlorine, with or without additional catalysts, under free-radical or aromatic electrophilic halogenation conditions, depending on the nature of Z. Alternative sources of halogen, such as N-halosuccinimides, tert-butyl hypohalites or SO₂Cl₂, may also be used. (See March, *J. Advanced Organic Chemistry*; 3rd ed., John Wiley: New York, (1985), pp 476–479, 620–626; and references therein.) For a review of free-radical halogenation, see Huyser, in Patai, "The Chemistry of the Carbon-Halogen Bond," Part 1, Wiley, New York (1973) pp 549–607. For electrophilic substitutions, see de la Mare, "Electrophilic Halogenation," Cambridge University Press, London (1976). Compounds of Formula 43 correspond to compounds of Formula 15 in Scheme 7 where Lg=Br, Cl, or I and reagent Z-hal in Scheme 24. Compounds of Formula 47 can be prepared from compounds of Formula 46 by similar procedures. Compounds of Formula 36 or 37 in Scheme 23 can be prepared by reaction of compounds of Formula 47 with triphenylphosphine or trialkyl phosphites, respectively, followed by deprotonation with base. See Cadogen, "Organophosphorus Reagents in Organic Synthesis," Academic Press, New York (1979) for a general treatise on these reagents.

Scheme 28

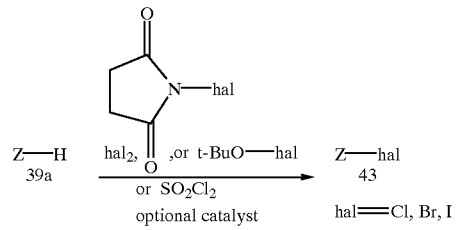

-continued

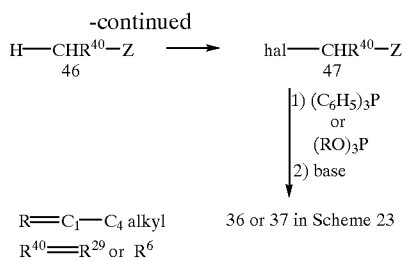

R=C$_1$—C$_4$ alkyl
R$^{40}$=R$^{29}$ or R$^6$ 36 or 37 in Scheme 23

Compounds of Formula 48 can be prepared from compounds of Formula 40b by treatment with peracids such as perbenzoic or peracetic acid, or with other peroxy compounds in the presence of an acid catalysts, followed by hydrolysis of the resultant ester. For a review, see Plesnicar, in Trahanovsky, "Oxidation in Organic Chemistry, pt. C, Academic Press, New York (1978) pp 254–267. Formula 48 corresponds to reagent HO—Z in Scheme 21. Compounds of Formula 52 can be prepared from compounds of Formula 48 by conversion to the dialkylthiocarbamates of Formula 50 followed by rearrangement to Formula 51 and subsequent hydrolysis. See M. S. Newman and H. A. Karnes, *J. Org. Chem.* (1966), 31, 3980–4. Formula 52 corresponds to reagent HS—Z in Scheme 21.

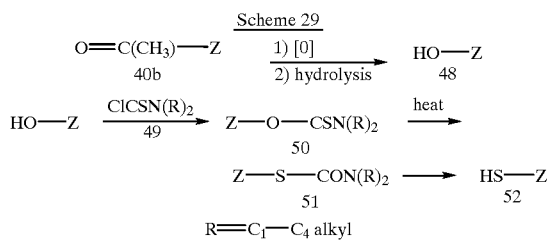

R=C$_1$—C$_4$ alkyl

Compounds of Formula 53 can be converted to compounds of Formulae 43, 48 or 52 via the diazonium compounds 54, by treatment with nitrous acid followed by subsequent reaction (Scheme 30). See reviews by Hegarty, pt. 2, pp 511–91 and Schank, pt. 2, pp 645–657, in Patai, "The Chemistry of Diazonium and Diazo Groups," Wiley, New York (1978). Treatment of Formula 54 compounds with cuprous halides or iodide ions yield compounds of Formula 43. Treatment of Formula 54 compounds with cuprous oxide in the presence of excess cupric nitrate provides compounds of Formula 48. (Cohen, Dietz, and Miser, *J. Org. Chem*, (1977), 42, 2053). Treatment of Formula 54 compounds with $(S_2)^{-2}$ yields compounds of Formula 52.

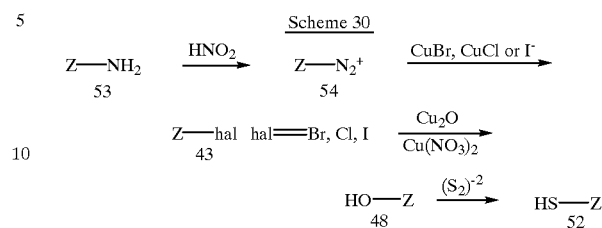

Compounds of Formula 53 can be prepared from compounds of Formula 39a by nitration, followed by reduction (Scheme 31). A wide variety of nitrating agents is available (see Schofield, "Aromatic Nitration," Cambridge University Press, Cambridge (1980)). Reduction of nitro compounds can be accomplished in a number of ways (see March, *J. Advanced Organic Chemistry*; 3rd ed., John Wiley: New York, (1985), pp 1103–4 and references therein). Formula 53 corresponds to Formula 13 in Scheme 6 when $Y^1=NR^{15}$ and $R^{15}=H$.

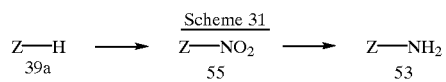

Iodides of Formula 8 can be prepared from compounds of Formula 58 by the methods described above in Schemes 21–25 for various Y-Z combinations. Compounds of Formula 58 can in turn be prepared from compounds of Formula 57 by functional group interconversions which are well known to one skilled in the art. The compounds of Formula 57 can be prepared by treating compounds of Formula 56 with an organolithium reagent such as n-BuLi or LDA followed by trapping the intermediate with iodine (Beak, P., Snieckus, V. *Acc. Chem. Res.*, (1982), 15, 306). Additionally, lithiation via halogen metal exchange of compounds of Formula 56, where H is replaced by Br, will produce an intermediate which can be trapped with iodine to prepare compounds of Formula 57 (Parham, W E., Bradsher, C. K. *Acc. Chem. Res.*, (1982), 15, 300 (Scheme 32).

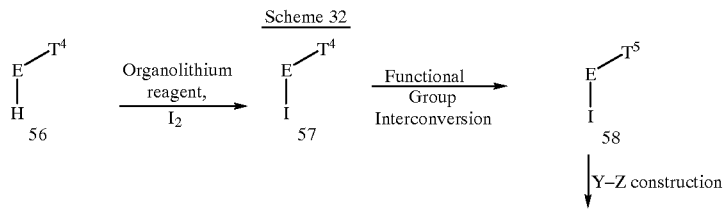

-continued

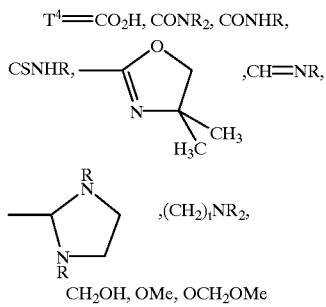

$T^4$=$CO_2H$, $CONR_2$, $CONHR$,

CSNHR, ,CH=NR,

,$(CH_2)_tNR_2$, $CH_2OH$, OMe, $OCH_2OMe$

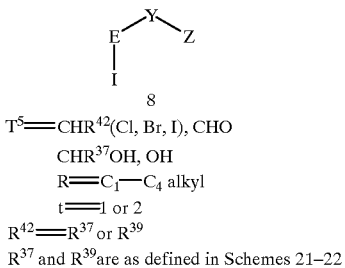

$T^5$=$CHR^{42}$(Cl, Br, I), CHO
$CHR^{37}OH$, OH
R=$C_1$—$C_4$ alkyl
t=1 or 2
$R^{42}$=$R^{37}$ or $R^{39}$
$R^{37}$ and $R^{39}$ are as defined in Schemes 21–22

Conversion of compounds of Formula In to compounds of Formula Io is summarized in Scheme 33. Reaction of the secondary amides with silylating agents, such trimethylsilyl chloride in the presence of base or hexamethyldisilazane in the presence of acid, provides the silylated intermediate which is oxidized in situ with the peroxo-molybdenum compound $MoO_5$-HMPA complexed with pyridine or dimethylformamide. Subsequent hydrolysis with aqueous EDTA (ethylenediaminetetraacetic acid) liberates the hydroxylated amides (see S. A. Martin, P. G. Sammes and R. M. Upton, *J. Chem. Soc., Perkin Trans.* 1 (1979), 2481 and J. H. Rigby and M. Qabar, *J. Org. Chem.* (1984), 54, 5852). Optional alkylation with $C_1$–$C_2$ alkyl halides in the presence of base or acylation with acetic anhydride can be performed on the hydroxyl amides Io where $R^{2'}$=OH.

Scheme 33

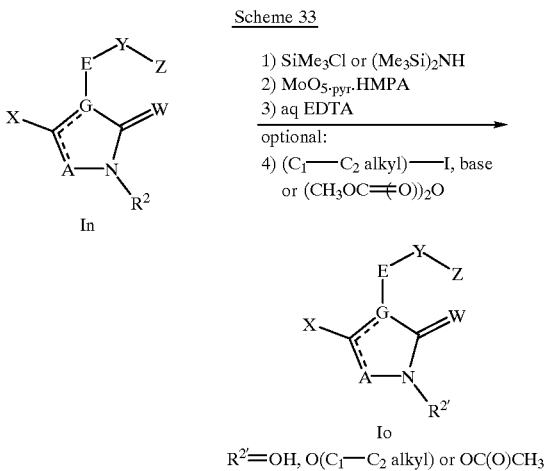

1) $SiMe_3Cl$ or $(Me_3Si)_2NH$
2) $MoO_{5\cdot pyr}$·HMPA
3) aq EDTA
optional:
4) ($C_1$—$C_2$ alkyl)—I, base
or $(CH_3OC(=O))_2O$ $R^{2'}$=OH, O($C_1$—$C_2$ alkyl) or OC(O)$CH_3$ It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, dt=doublet of triplets, td=triplet of doublets, br s=broad singlet.

EXAMPLE 1

Step A: Preparation of 2,2-dimethyl-N-(2-methylphenyl)hydrazine carboxamide o-Tolyl isocyanate (10.0 g) was dissolved in 75 mL toluene under $N_2$. The solution was cooled to 5° C. and to this was slowly added a solution in toluene of 1,1-dimethylhydrazine (5.7 mL). After addition, the ice-bath was removed and the resulting slurry allowed to stir an additional 10 minutes. The solid was collected by filtration and rinsed successively with hexane, a small amount of 20% diethyl ether/hexane, and then hexanes again. This afforded 11.1 g of the title compound of Step A. $^1$H NMR (CDCl$_3$): δ 8.1 (br s,1H), 7.94 (d,1H), 7.21–7.15 (m,3H), 6.99 (t,1H), 5.23 (br s,1H), 2.63 (s,6H), 2.27 (s,3H).

Step B: Preparation of 5-chloro-2,4-dihydro-2-methyl-4-(2-methylphenyl)-3H-1,2,4-triazol-3-one To a solution of 11.1 g of the title compound of Step A dissolved in 600 mL methylene chloride under $N_2$ was added 17.1 g of triphosgene. The solution was heated at reflux overnight, cooled, and then concentrated under reduced pressure. The resulting residue was dissolved in ethyl acetate and washed with water and then with saturated aqueous NaCl. The organic phase was dried (MgSO$_4$), filtered, and concentrated under reduced pressure. The residue was purified by flash chromatography (30–50% ethyl acetate/hexanes as eluent) to afford 8.25 g of the title compound of Step B. $^1$H NMR (CDCl$_3$): δ 7.42–7.30 (m,3H), 7.17 (d,1H), 3.54 (s,3H), 2.22(s,3H).

Step C: Preparation of 2,4-dihydro-5-methoxy-2-methyl-4-(2-methylphenyl)-3H-1,2,4-triazol-3-one 8.25 g of the title compound of Step B was dissolved in 80 mL of 1:1 dimethoxyethane/methanol under $N_2$. 14.0 mL of sodium methoxide (30% solution in methanol) was added and the solution was heated at reflux for 3 h. The mixture was allowed to cool, diluted with ethyl acetate, washed with water and then with saturated aqueous NaCl. The combined organic extracts were dried (MgSO$_4$), filtered, and concentrated under reduced pressure. The residue was purified by flash chromatography (50–70% ethyl acetate/hexanes as eluent) and triturated with 50% diethyl ether/hexanes to afford 6.7 g of the title compound of Step C (about 95% pure). $^1$H NMR (CDCl$_3$): δ 7.35–7.27 (m,3H), 7.18 (d,1H), 3.94 (s,3H), 3.46 (s,3H), 2.22 (s,3H).

Step D: Preparation of 4-[2-(bromomethyl)phenyl]-2,4-dihydro-5-methoxy-2-methyl-3H-1,2,4-triazol-3-one To a solution/suspension of 6.7 g of the title compound of Step C dissolved in 95 mL of carbon tetrachloride under N$_2$ was added N-bromosuccinimide (6.53 g) followed by a catalytic amount of benzoyl peroxide. The solution was heated at reflux for 2 h. Another 1.63 g of N-bromosuccinimide and a catalytic amount of benzoyl peroxide were added and the solution was heated at reflux for an hour. After cooling, methylene chloride was added and the organic layer was washed successively with water, then with 0.1 N sodium thiosulfate solution, and then with saturated aqueous NaCl. The combined organic extracts were dried (MgSO$_4$), filtered, and concentrated under reduced pressure. The residue was purified by flash chromatography (3–10% diethyl-ether/methylene chloride as eluent) to afford 3.12 g of the title compound of Step D. $^1$H NMR (CDCl$_3$): δ 7.5 (m,1H), 7.44 (m,2H), 7.22 (m,1H), 4.60 (d,1H), 4.36 (d,1H), 3.96 (s,3H), 3.47 (s,3H).

Step E: Preparation of [[2-(1,5-dihydro-3-methoxy-1-methyl-5-oxo4H-1,2,4-triazol-4-yl)phenyl]methyl]N-(4-chlorophenyl)propanimidothioate To a solution of 0.50 g of the title compound of Step D in 2 mL of THF was added 0.37 g of 4'-chlorothiopropionanilide and then 0.23 g of potassium tert-butoxide. (An exotherm occurred during this addition). The reaction was allowed to stir at room temperature overnight and then was heated briefly to reflux and allowed to cool. The reaction mixture was diluted with ethyl acetate and washed successively with water and then with saturated aqueous NaCl. The organic phase was dried (MgSO$_4$), filtered, and concentrated under reduced pressure. The residue was purified by flash chromatography (50–60% ethyl acetate/hexanes) to afford 0.48 g of the title compound of Step E (about 95% pure), a compound of the invention. $^1$H NMR (CDCl$_3$): δ 7.58 (m,1H), 7.37 (m,2H), 7.23 (m,3H), 6.60 (d,2H), 4.23 (s,2H), 3.86 (s,3H), 3.41 (s,3H).

EXAMPLE 2

Step A: Preparation of 2-(1,5-dihydro-3-methoxy-1-methyl-5-oxo-4H-1,2,4-triazol-4-yl)benzaldehyde A solution of the title compound of Step D in Example 1 (1.03 g, 0.0036 mol) in carbon tetrachloride (3 mL) was added to a solution of 4-methylmorpholine N-oxide (1.09 g, 0.0093 mol) in dimethyl sulfoxide (9 mL) at 7° C. The mixture was stirred at 7° C. for 30 min, at room temperature for 18 h, and then poured into cold, half-saturated aqueous sodium chloride and extracted with diethyl ether (4×). The combined organic phase was washed with saturated aqueous NaCl, dried (Na$_2$SO$_4$), filtered and concentrated to a light brown oil that was purified by flash column chromatography on silica gel to give 0.37 g of the title compound of Step A as a white solid melting at 82–84° C. $^1$H NMR (300 MHz, CDCl$_3$): δ 9.97 (s,1H), 8.00 (dd,1H, J=1.5, 8.5 Hz), 7.73 (dt,1H, J=1.6, 7.8 Hz), 7.61 (t,1H, J=7.5 Hz), 7.42 (d,1H, J=7.8 Hz), 3.95 (s,3H), 3.47 (s,3H).

Step B: Preparation of (1,1-dimethylethyl) dichloro (diethoxyphosphinyl)acetate

A solution of 5.25% sodium hypochlorite (Clorox® bleach; 421.5 g, 0.2973 mol) was adjusted to pH 7.1 with 3N HCl and then tert-butyl diethylphosphonoacetate (15.0 g, 0.0595 mol) was added dropwise at 0° C. with vigorous stirring. After the addition was complete, the ice-bath was removed and stirring was continued for 1 h. The reaction mixture was extracted with hexane (5 times) and the combined organic phase was dried (MgSO$_4$), filtered and concentrated to afford 18.4 g of the title compound of Step B as a colorless oil. $^1$H NMR (300 MHz, CDCl$_3$): δ 4.41–4.36 (m,4H), 1.57 (s,9H), 1.40 (t,6H, J=7.2 Hz).

Step C: Preparation of (1,1-dimethylethyl) chloro (diethoxyphosphinyl)acetate

The title compound of Step B (18.4 g, 0.0572 mol) was dissolved in ethanol (140 mL) and cooled to 0° C. A solution of sodium sulfite (14.4 g, 0.1144 mol) in H$_2$O (63 mL) was added with stirring such that the internal temperature remained below 14° C. The cooling bath was removed and the mixture was stirred at room temperature for 30 min. The reaction mixture was extracted with chloroform (5×), and the combined organic phase was dried (MgSO$_4$), filtered and concentrated to afford 16.4 g of the title compound of Step C as a clear oil. $^1$H NMR (300 MHz, CDCl$_3$): δ 4.43 (d,1H, J=15.9 Hz), 4.30–4.24 (m,4H), 1.52 (s,9H), 1.38 (t,6H, J=6.9 Hz).

Step D: Preparation of 1,1-dimethylethyl 2-chloro-3-[2-(1,5-dihydro-3-methoxy-1-methyl-5-oxo4H-1,2,4-triazol-4-yl)phenyl]-2-propenoate A solution of the title compound in Step C (0.43 g, 0.0015 mol) in ethyl acetate (3 mL) was added to a mixture of calcium hydroxide (0.110 g, 0.0015 mol) and the title compound of Step A (0.350 g, 0.0015 mol) in ethyl acetate (5 mL). The resulting mixture was stirred at 45° C. overnight and then poured into ice water and extracted three times with ethyl acetate. The combined organic phase was washed successively with saturated aqueous NaCl and then a 1/1 mixture of saturated aqueous NaCl and saturated aqueous sodium hydrogen carbonate, dried (Na$_2$SO$_4$), filtered and concentrated to a light yellow oil. The crude product was purified by flash column chromatography on silica gel to give 0.320 g of the title compound of Step D, a compound of the invention, as a white semisolid consisting of a 1:1 ratio of E- and Z-isomers. $^1$H NMR (300 MHz, CDCl$_3$; for the E/Z mixture): δ 7.66 and 7.21 (2s,1H total), 7.25–7.54 (m,4H total). 3.93 and 3.91 (2s,3H total), 3.44 (s,3H), 1.54 and 1.25 (2s.9H total).

EXAMPLE 3

Step A: Preparation of β-oxo-3-(trifluoromethyl) benzenepropanenitrile

To a suspension of 7.6 g of sodium hydride (60% dispersion in oil) in 200 mL of tetrahydrofuran under a nitrogen atmosphere was added dropwise at room temperature a solution consisting of 7.8 g of acetonitrile and 38.8 g of methyl 3-(trifluoromethyl)benzoate in 50 mL of tetrahydrofuran. Following addition, the suspension was stirred 1 h at ambient temperature, refluxed about 5 h, and then cooled to room temperature. Isopropyl alcohol (20 mL) was added dropwise at room temperature. After stirring about 15 min, the solvent was removed in vacuo, and about 200 mL of water was added to the residue. The aqueous suspension was washed with 3×50 mL diethyl ether and then acidified with concentrated hydrochloric acid to form a solid. The solid was isolated by filtration, washed 2×100 mL with water and then dissolved in methylene chloride. The organic solution was dried (MgSO$_4$), filtered and concentrated to give 30.0 g of the title compound of Step A as a white solid melting at 51–55° C. $^1$H NMR (CDCl$_3$): δ 8.1–8.2 (m,2H), 7.95 (d,1H), 7.7 (m,1H), 4.15 (s,2H); IR (mineral oil) 1704.1 cm$^{-1}$.

Step B: Preparation of α-(hydroxyimino)-β-oxo-3-(trifluoromethyl)benzenepropanenitrile To a solution of 30.0 g of the title compound of Step A in 200 mL of glacial acetic acid was added dropwise a solution of 11.7 g of sodium nitrite in 35 mL of water while maintaining the reaction temperature at about 15° C. with external cooling. Following addition, the external cooling was removed and the suspension was stirred at room temperature overnight and then poured into excess water (about 400 mL). The aqueous suspension was acidified by dropwise addition of concentrated hydrochloric acid (until red to litmus paper) and then extracted with methylene chloride. The organic solution was dried (MgSO$_4$), filtered and concentrated to give 32.5 g of the title compound of Step B as an oil. $^1$H NMR (CDCl$_3$): δ 8.3 (s,1H), 8.2 (m,1H), 7.9 (m,1H), 7.65 (m,1H); IR (neat) 1670.2 cm$^{-1}$.

Step C: Preparation of α-[[[2-(1,5-dihydro-3-methoxy-1-methyl-5-oxo-4H-1,2,4-triazol-4-yl)phenyl]methoxy]imino]-β-oxo-3-(trifluoromethyl)benzenepropanenitrile The title compound of Step B was dissolved in 5 mL of DMF and 0.07 g (1.74 mmol) of sodium hydride as a 60% dispersion in oil was added to the solution. Then 0.400 g (1.34 mmol) of the title compound of Step D in Example 1 was added and the reaction mixture was stirred at room temperature for 5 h. The reaction mixture was diluted with ethyl acetate, then washed successively with water and saturated aqueous NaCl. The combined organic extracts were dried over magnesium sulfate, filtered, and concentrated. The crude product was purified by flash chromatography using ethyl acetate:hexane 1:1 to give 0.48 g of the title compound of Step C, a compound of invention. $^1$H NMR (CDCl$_3$): δ 8.18 (s,1H), 7.98 (m,1H), 7.82 (m,1H), 7.50 (m,4H), 7.30 (d,1H), 5.59 (d,1H), 5.46 (d,1H), 3.93 (s,3H), 3.41 (s,3H).

EXAMPLE 4

Step A: Preparation of 3,4-dichlorobenzaldehyde oxime 3,4-Dichlorobenzaldehyde (5.25 g) and 2.1 g of hydroxylamine hydrochloride were dissolved in 75 mL of pyridine. The mixture was stirred at room temperature for 18 h. The solvent was removed in vacuo and the residue was taken up in 100 mL of 1N HCl and extracted 3× with 75 mL portions of ethyl acetate. The combined organic extracts were dried (MgSO$_4$), filtered, and concentrated to give a solid. The crude material was triturated in hexane and collected by filtration to yield 5.8 g of the title compound of Step A as a white solid melting at 118–119° C.

Step B: Preparation of 3,4-dichloro-N-hydroxybenzenecarboximidoyl chloride

The title compound of Step A (3.7 g) was dissolved in 100 mL of dimethylformamide and 2.6 g of N-chlorosuccinimide was added. The reaction mixture was stirred at about 30° C. for 2 h and then at room temperature overnight. The mixture was diluted with 200 mL of water and extracted with three 100 mL portions of diethyl ether. The combined organic extracts were dried (MgSO$_4$), filtered, and concentrated to give 5.8 g of the title compound of Step B as an oil. $^1$H NMR (CDCl$_3$): δ 10.41 (s,1H), 7.95 (d,1H,J=2 Hz), 7.69 (dd,1H, J=2, 8 Hz), 7.46 (d,1H,J=8 Hz). The crude oil also contained DMF. The crude material was triturated in hexane and collected by filtration to yield 5.2 g of white solid, still containing DMF, which was used in the next step without additional purification or characterization.

Step C: Preparation of S-methyl 3,4-dichloro-N-hydroxybenzenecarboximidothioate

The product from Step B (5.2 g) was dissolved in 70 mL of tetrahydrofuran and 2.9 g of sodium thiomethoxide and 7 mL of methanol were added. The reaction mixture was stirred at room temperature for 2 h. Water (20 mL) was added and the mixture clarified to a yellow solution. The solution was diluted with 100 mL of methylene chloride and the aqueous phase was made acidic with 1N HCl. The phases were separated and the aqueous phase extracted with three 50 mL portions of methylene chloride. The combined organic layers were dried (MgSO$_4$), filtered, and concentrated to give 5.1 g of the title compound of Step C as an oil. $^1$H NMR (CDCl$_3$): δ 9.09 (br s,1H), 7.59 (d,1H,J=2Hz), 7.51 (d,1H,J=8 Hz), 7.33 (dd,1H,J=2, 8 Hz), 2.16 (s,3H). The crude material was not further purified before Step F.

Step D: Preparation of N-[2-(bromomethyl)phenyl]-2,2-dimethylhydrazinecarboxamide o-Tolyl isocyanate (50.4 g) and 75.2 g of N-bromosuccinimide dissolved in 800 mL of carbon tetrachloride were heated to reflux. Benzoyl peroxide (1.1 g) was added and the mixture was heated to reflux for 1.5 h. The solution was cooled to room temperature and the precipitate was removed by filtration. The filtrate was concentrated in vacuo and redissolved in 500 mL of toluene and cooled to 5° C. 1,1-Dimethylhydrazine, (30 mL in 20 mL of toluene) was added dropwise. The reaction mixture was stirred at room temperature overnight. The precipitated solid was collected by filtration and redissolved in 1 L of dichloromethane. The organic solution was washed with 500 mL of water and then 500 mL of saturated aqueous sodium chloride. The organic layer was dried (MgSO$_4$), filtered and concentrated to give 58 g of the title compound of Step D as a beige solid. $^1$H NMR (CDCl$_3$): δ 8.6 (br s,1H), 8.00 (d,1H), 7.30 (m,2H), 7.04 (t,1H), 5.70 (br s,1H), 4.52 (s,2H), 2.67 (s,6H). The material was used in Step E without further characterization.

Step E: Preparation of 5-chloro-4-[2-(chloromethyl)phenyl]-2,4-dihydro-2-methyl-3H-1,2,4-triazol-3-one The product from Step D (58 g) was dissolved in 800 mL of dichloromethane and 86 g of triphosgene was added in one portion. A slight exotherm was observed and then the mixture was heated to reflux overnight. The reaction mixture was cooled and the solvent removed in vacuo. The resulting solid was dissolved in 1 L of ethyl acetate and washed with 500 mL of water, 500 mL of saturated aqueous sodium bicarbonate and then 500 mL of saturated aqueous sodium chloride. The organic layer was dried (MgSO$_4$), filtered, and concentrated to give a dark oil which solidified on standing. The solid was triturated in 2:1 hexane: n-butyl chloride to yield 32 g of a beige solid. Recrystallization of the solid from 150 mL of hot methanol yielded 21 g of the title compound of Step E as a white fluffy solid melting at 122–124° C. A second crop was obtained from recrystallization of the mother liquors. $^1$H NMR (CDCl$_3$): δ 7.45–7.6 (m,3H), 7.25 (m,1H), 4.68 (d,1H), 4.46 (d,1H), 3.56 (s,3H). Approximately 10% of 5-chloro-4-[2-(bromomethyl)phenyl]-2,4-dihydro-2-methyl-3H-1,2,4-triazol-3-one was observed in the $^1$H NMR spectrum. $^1$H NMR (CDCl$_3$): δ 7.56 (m,2H), 7.44 (m,3H), 7.25 (m,2H), 5.26 (AB quartet, 2H), 3.9 (s,3H), 3.41 (s,3H), 2.1 (s,3H)

Step F: Preparation of S-methyl 3,4-dichloro-N-[[2-(3-chloro-1,5-dihydro-1-methyl-5-oxo-4H-1,2,4-triazol-4-yl)phenyl]methoxy]benzenecarboximidothioate The product from Step C (2.07 g) was dissolved in 10 mL of tetrahydrofuran and 10 mL of 1.0 M potassium t-butoxide in THF was added dropwise. After the addition was complete, the mixture was stirred 15 min, and then the title compound of Step E (2.06 g) was added. The reaction mixture was stirred at room temperature overnight, and then diluted with 20 mL of water and extracted with three 30 mL portions of ethyl acetate. The combined organic extracts were dried (MgSO$_4$), filtered, and concentrated to give 3.53 g of the title compound of Step F as an oil. $^1$H NMR (CDCl$_3$): δ 7.5 (m,5H), 7.25 (m,2H), 5.34 (d,1H), 5.18 (d,1H), 3.49 (s,3H), 2.08 (s,3H). The crude product contained minor amounts of impurities and solvent, but the material was not further purified before Step G.

Step G: Preparation of S-methyl 3,4-dichloro-N-[[2-(1,5-dihydro-3-methoxy-1-methyl-5-oxo-4H-1,2,4-triazol-4-yl)phenyl]methoxy]benzenecarboximidothioate The crude product from Step F (3.53 g) was dissolved in 25 mL of dimethoxyethane and 25 mL of methanol. Sodium methoxide (25% in methanol, 4.4 mL) was added dropwise.

The mixture was heated to reflux for 3 h, then stirred at room temperature overnight. An additional 1.1 mL of 25% sodium methoxide in methanol was added and the mixture was heated to reflux for 6 h, and then stirred at room temperature overnight. The solvents were removed in vacuo and the residue taken up in 100 mL of ethyl acetate. The mixture was extracted with 50 mL of water and then with 50 mL of saturated aqueous sodium chloride. The organic layer was dried ($MgSO_4$), filtered, and concentrated to give 2.8 g of an oil. Trituration in hexane/n-butyl chloride formed a solid which was collected by filtration to yield 2.19 g of the title compound of Step G, a compound of the invention. $^1$H NMR ($CDCl_3$): δ 7.56 (m,2H), 7.44 (m,3H), 7.25 (m,2H), 5.26 (AB quartet,2H), 3.9 (s,3H), 3.41 (s,3H), 2.1 (s,3H).

EXAMPLE 5

Step A: Preparation of 1-(3,5-dichlorophenoxy)-2-propanone

To a stirred solution of 3,5-dichlorophenol (0.49 g, 3 mmol) in acetone (10 mL) under a nitrogen atmosphere was added potassium carbonate (0.42 g, 3 mmol). In a separate flask, chloroacetone (0.34 mL, 4.2 mmol) and potassium iodide (0.02 g, 0.12 mmol) were dissolved in acetone (15 mL), heated at reflux for 10 min and then allowed to cool to room temperature. The chloroacetone solution was then added to the dichlorophenol solution dropwise via an addition funnel. The resulting mixture was stirred at room temperature overnight. The resulting solids were filtered off and the filtrate was concentrated under reduced pressure to yield the title compound of Step A (0.65 g) as a semisolid. 400 MHz $^1$H NMR ($CDCl_3$): δ 7.01 (t,1H), 6.8 (d,2H), 4.5 (s,2H), 2.3 (s,3H). This material was used in Step D without further characterization.

Step B: Preparation of N-[[2-(1,5-dihydro-3-methoxy-1-methyl-5-oxo4H-1,2,4-triazol4-yl)phenyl]methoxy]benzamide To a solution of benzohydroxamic acid (6.03 g, 44 mmol) in methanol (60 mL) under a nitrogen atmosphere was added sodium methoxide (25% solution in methanol, 37 mL, 160 mmol) via an addition funnel. The resulting mixture was stirred at room temperature for 15 min. The title compound of Step E in Example 4 (10.32 g, 40 mmol) and then DME (40 mL) were added and the resulting mixture was heated under reflux for 5 h. After cooling to room temperature, the reaction mixture was concentrated under reduced pressure. The residue was diluted with 1 N aqueous HCl and was extracted three times with ethyl acetate. After drying ($MgSO_4$), the combined organic extracts were concentrated under reduced pressure to yield the title compound of Step B (11.6 g) as an oil. 400 MHz $^1$H NMR ($CDCl_3$): δ 9.86 (s,1H), 7.59 (d,2H), 7.5 (m,4H), 7.3 (m,3H), 5.16 (d,1H), 4.94 (d,1H), 3.94 (s,3H), 3.41 (s,3H). Minor impurity signals: 4.4 (q,4H), 3.45 (s,3H), 3.31 (s,3H). This material was used in Step C without further characterization.

Step C: Preparation of 4-[2-[(aminooxy)methyl]phenyl]-2,4-dihydro-5-methoxy-2-methyl-3H-1,2,4-triazol-3-one hydrochloride To a stirred solution of the title compound of Step B (11.6 g, 32.7 mmol) in ethanol (200 mL) under a nitrogen atmosphere was added concentrated sulfuric acid (4 mL). The resulting mixture was stirred at room temperature overnight. The reaction mixture was concentrated under reduced pressure and the residue was partitioned between water and diethyl ether. The aqueous phase was basified with 1 N aqueous NaOH and was extracted three times with ethyl acetate and then three times with methylene chloride. The ethyl acetate and methylene chloride extracts were combined, dried ($MgSO_4$), and then concentrated under reduced pressure. The resulting residue was dissolved in diethyl ether (300 mL) and isopropanol (6 mL). To this solution was added 1 N HCl in diethyl ether (35 mL) dropwise via addition funnel at 0 ° C. The resulting precipitate was collected by filtration affording the title compound of Step C (5.56 g) as a yellow solid melting at 117–120 ° C. 400 MHz $^1$H NMR ($Me_2SO$-$d_6$): δ 7.57 (m,3H), 7.43 (m,1H), 4.92 (s,2H), 3.89 (s,3H), 3.33 (s,3H).

Step D: Preparation of 4-[2-[[[[2-(3,5-dichlorophenoxy)-1-methylethylidene]amino]oxy]methyl]phenyl]-2,4-dihydro-5-methoxy-2-methyl-3H-1,2,4-triazol-3-one To a stirred solution of the title compound of Step A (0.33 g, 1.5 mmol) in pyridine (30 mL) under a nitrogen atmosphere was added the title compound of Step C (0.43 g, 1.5 mmol) and the resulting mixture was heated at 90 ° C. for 2 h. The reaction mixture was allowed to cool to room temperature overnight. The reaction mixture was concentrated under reduced pressure and the residue was diluted with 1 N aqueous HCl and was extracted three times with ethyl acetate. After drying ($MgSO_4$), the combined organic extracts were concentrated under reduced pressure. Chromatography of the residue on silica gel (200 g) with 1:1 hexane: ethyl acetate afforded 0.14 g of the title compound of Step D, a compound of the invention, as an oil. 300 MHz $^1$H NMR $CDCl_3$): δ 7.44 (m,3H), 7.23 (m,1H), 6.96 (m,1H), 6.81 (m,2H), 5.12 (q,2H), 4.44 (s,2H), 3.9 (s,3H), 3.43 (s,3H), 1.89 (s,3H).

EXAMPLE 6

Step A: Preparation of 2,2-dimethyl-N-(2-methylphenyl)hydrazinecarboxamide o-Tolyl isocyanate (10.0 g) was dissolved in 75 mL of toluene under nitrogen. The solution was cooled to 5° C. and to this was slowly added a solution of 1,1-dimethylhydrazine (5.7 mL) in toluene. After addition, the ice-bath was removed and the resulting slurry was allowed to stir an additional 10 minutes. The solid was filtered off and rinsed successively with hexane, a small amount of 20% diethyl ether/hexane, and then hexanes again. This afforded 11.1 g (77%) of the title compound of Step A. $^1$H NMR ($CDCl_3$): δ 8.1 (br s,1H), 7.94 (d,1H), 7.21–7.15 (m,3H), 6.99 (t,1H), 5.23 (br s,1H), 2.63 (s,6H), 2.27 (s,3H).

Step B: Preparation of 5-chloro-2,4-dihydro-2-methyl-4-(2-methylphenyl)-3H-1,2,4-triazol-3-one To a solution of 11.1 g of the title compound of Step A dissolved in 600 mL of methylene chloride under nitrogen was added 17.1 g of triphosgene. The solution was heated at reflux overnight, cooled, and then concentrated under reduced pressure. The resulting residue was dissolved in ethyl acetate, washed with water and then washed with saturated aqueous NaCl. The organic phase was dried ($MgSO_4$), filtered, and concentrated under reduced pressure. The residue was purified by flash chromatography (30–50% ethyl acetate/hexanes as eluent) to afford 8.25 g (64% yield) of the title compound of Step B. $^1$H NMR ($CDCl_3$): δ 7.42–7.30 (m,3H), 7.17 (d,1H), 3.54 (s,3H), 2.22 (s,3H).

Step C: Preparation of 2,4-dihydro-5-methoxy-2-methyl-4-(2-methylphenyl)-3H-1,2,4-triazol-3-one 8.25 g of the title compound of Step B was dissolved in 80 mL of 1:1 dimethoxyethane/methanol under $N_2$. 14.0 mL of sodium methoxide (30% solution in methanol) was added and the solution was heated at reflux for 3 h. The mixture was allowed to cool, diluted with ethyl acetate, washed with water, and then washed with saturated aqueous NaCl. The combined organic extracts were dried ($MgSO_4$), filtered, and concentrated under reduced pressure. The residue was purified by flash chromatography (50–70% ethyl acetate/hexanes as eluent) and triturated with 50% diethyl ether-lhexanes to afford 6.7 g of the title compound of Step C (95% pure). $^1$H NMR ($CDCl_3$): δ 7.35–7.27 (m,3H), 7.18 (d,1H), 3.94 (s,3H), 3.46 (s,3H), 2.2 (s,3H).

Step D: Preparation of 4-[2-(bromomethyl)phenyl]-2,4-dihydro-5-methoxy-2-methyl-3H-1,2,4-triazol-3-one To a solution/suspension of 6.7 g of the title compound of Step C dissolved in 95 mL of carbon tetrachloride under $N_2$ was added N-bromosuccinirnide (6.53 g) followed by a catalytic amount of benzoyl peroxide. The solution was heated at reflux for 2 h. Another 1.63 g of N-bromosuccinimide and a catalytic amount of benzoyl peroxide were added and the solution was heated at reflux for an hour. After cooling, methylene chloride was added and the organic layer was washed successively with water, 0.1 N sodium thiosulfate solution, and then saturated aqueous NaCl. The combined organic extracts were dried ($MgSO_4$), filtered, and concentrated under reduced pressure. The residue was purified by flash chromatography (3–10% diethyl ether/methylene chloride as eluent) to afford 3.12 g of the title compound of Step D. $^1$H NMR ($CDCl_3$): δ 7.5 (m,1H), 7.44 (m,2H), 7.22 (m,1H), 4.60 (d,1H), 4.36 (d,1H), 3.96 (s,3H), 3.47 (s,3H).

Step E: Preparation of methyl (4-bromophenyl) carbamodithioate

To a stirred solution of carbon disulfide (6 mL, 100 mmol) at 0 ° C. under a nitrogen atmosphere was added a mixture of p-bromoaniline (1.72 g, 10 mmol) and triethylamine (1.4 mL, 10 mmol) dropwise via an addition funnel. The reaction mixture was stirred at 0 ° C. for 1.5 h, and then allowed to warm to room temperature overnight. To the reaction mixture was added iodomethane (0.62 mL, 10 mmol). The reaction mixture was stirred at room temperature for 2 h. The reaction mixture was diluted with diethyl ether (40 mL), and the resulting precipitate was filtered off. The filtrate was concentrated under reduced pressure and trituration of the residue with hexane afforded the title compound of Step E (2.34 g) as a solid melting at 111–112 ° C. 300 MHz $^1$H NMR ($CDCl_3$): δ 8.67 (s,1H), 7.53 (d,2H), 7.38 (d,2H), 2.67 (s,3H).

Step F: Preparation of [[2-(1,5-dihydro-3-methoxy-1-methyl-5-oxo-4H-1,2,4-triazol-4-yl)phenyl]methyl]methyl (4-bromophenyl)carbonimidodithioate To a stirred solution of the title compound of Step E (0.088 g, 0.33 mmol) in THF (25 mL) under a nitrogen atmosphere was added 60% sodium hydride (0.02 g, 0.40 mmol) and the resulting mixture was stirred at room temperature for 15 min. To this solution was added the title compound of Step D and the mixture was stirred for 4 h. The reaction mixture was diluted with water (100 mL) and extracted two times with ethyl acetate. After drying ($MgSO_4$), the combined organic extracts were concentrated under reduced pressure. The residue was purified by passing through a 150 mL medium-fritted filter funnel containing 50 g of silica gel with 1:1 hexane:ethyl acetate. This afforded 0.16 g of the title compound of Step F, a compound of the invention, as an oil. 400 MHz $^1$H NMR ($CDCl_3$): δ 7.55 (s,1H), 7.4 (m,4H), 7.2 (m,1H), 6.7 (m,2H), 4.33 (m,2H), 3.86 (s,3H), 3.43 (s,3H), 2.44 (s,3H).

EXAMPLE 7

N'-[[2-(1,5-dihydro-3-methoxy-1-methyl-5-oxo-4H-1,2,4-triazol-4-yl)phenyl]methoxy]-3,5-bis(trifluoromethyl)benzenecarboximidamide To a stirred solution of 0.95 g of 3,5-bis(trifluoromethyl)benzarnidoxime in 9 mL of tetrahydrofuran under $N_2$ was added 0.15 g of 60% sodium hydride and then 0.75 g of the title compound of Step E in Example 4. The reaction mixture was allowed to stir overnight, then 1.7 mL of 30% sodium methoxide in methanol was added and the reaction again was allowed to stir overnight. The reaction mixture was then diluted with ethyl acetate, washed with distilled water, then washed with saturated aqueous NaCl, dried over $MgSO_4$, and finally concentrated under reduced pressure. Purification of the resulting residue by flash chromatography on silica gel using 50% ethyl acetate in hexane afforded 0.75 g of the title compound of Example 7, a compound of the invention, as a white solid melting at 177–178 ° C. $^1$H NMR ($CDCl_3$): δ 8.05 (s,2H), 7.9 (s,1H), 7.6 (m,1H), 7.4–7.55 (m,2H), 7.3 (1H), 5.1 (m,2H), 5.05 (br s,2H), 3.92 (s,3H), 3.42 (s,3H).

EXAMPLE 8

Step A: Preparation of 2-(3-chloro-1,5-dihydro-1-methyl-5-oxo-4H-1,2,4-triazol-4-yl)benzaldehyde The title compound of Step E in Example 4 (0.50 g, 1.9 mmol) was dissolved in carbon tetrachloride (15 mL) and then 4-methylmorpholine N-oxide (0.54 g, 4.6 mmol) was added. The mixture was heated at reflux for 5 h, then cooled to room temperature and stirred for 18 h. The solution was diluted with water and extracted three times with ethyl acetate. The combined organic phase was washed with saturated aqueous NaCl, dried ($MgSO_4$), filtered and concentrated to an oil which was purified by flash column chromatography on silica gel to give 0.22 g of the title compound of Step A as a white solid melting at 136–138° C. $^1$H NMR (300 MHz, $CDCl_3$): δ 9.98 (s,1H), 8.02 (dd,1H, J=8, 2 Hz), 7.79 (td,1H, J=8, 2 Hz), 7.72 (td,1H, J=8, 2 Hz), 7.40 (dd,1H, J=8, 1 Hz), 3.56 (s,3H).

Step B: Preparation of 5-chloro-2,4-dihydro-2-methyl-4-[2-[[methyl[3-(trifluoromethyl)-2-pyridinyl]hydrazono]methyl]phenyl]-3H-1,2,4-triazol-3-one The title compound of Step A (0.20 g, 0.80 mmol) was dissolved in absolute ethanol (7 mL) and a solution of 1-[3-(trifluoromethyl)pyridin-2-yl]-1-methylhydrazine in ethanol (3 mL) was added followed by 3 drops of glacial acetic acid. The mixture was warmed to 50° C. for 1 h, cooled to room temperature and then diluted with aqueous sodium bicarbonate and extracted three times with ethyl acetate. The combined organic phases were dried ($MgSO_4$), filtered and concentrated to give 0.38 g of the title compound of Step B as a yellow solid. $^1$H NMR (300 MHz. $CDCl_3$): δ 8.42 (d.1H. J=5 Hz), 8.16 (d,1H, J=8 Hz), 8.01 (d,1H, J=8 Hz), 7.51 (t,1H, J=8 Hz), 7.42 (t,1H), J=8 Hz), 7.35 (s,1H), 7.21 (d,1H, J=8 Hz), 7.03 (dd,1H, J=8, 5 Hz), 3.56 (s,6H).

Step C: Preparation of 2,4-dihydro-5-methoxy-2-methyl-4-[2-[[methyl[3-(trifluoromethyl)-2-pyridinyl]hydrazono]methyl]phenyl]-3H-1,2,4-triazol-3-one The title compound of Step B (0.38 g, 0.93 mmol) was dissolved in THF (10 mL) and then sodium methoxide (25% in methanol, 0.56 mL) was added dropwise. The mixture was heated at reflux for 1 h, cooled to room temperature and then diluted with water and extracted three times with ethyl acetate. The combined organic phases were washed with saturated aqueous NaCl, dried ($MgSO_4$), filtered and concentrated to an oil which was purified by flash column chromatography on silica gel to afford 0.27 g of the title compound of Step C, a compound of the invention, as a pale yellow solid melting at 185–187° C. $^1$H NMR (300 MHz, $CDCl_3$): δ 8.41 (dd,1H, J=5, 1.5 Hz), 8.12 (dd,1H, J=8, 1.5 Hz), 8.01 (dd,1H, J=8, 1.5Hz), 7.42 (m,3H), 7.23 (d,1H J=8 Hz), 15 7.02 (dd,1H, J=8, 5Hz), 3.93 (s,3H), 3.56 (s,3H), 3.48 (s,3H).

By the procedures described herein together with methods known in the art, the following compounds of Tables 1 to 14 can be prepared. The following abbreviations are used in the Tables which follow: t=tertiary, n=normal, i=iso, c=cyclo, Me=methyl, Et=ethyl, Pr=propyl, i-Pr=isopropyl, Bu=butyl, Ph=phenyl, nap=naphthalenyl, MeO and OMe=methoxy, EtO=ethoxy, PhO=phenoxy, MeS and SMe=methylthio, EtS=ethylthio, CN=cyano, $NO_2$=nitro, and $SO_2Me$=methylsulfonyl.

TABLE 1

Compounds of Formula I where E = 1,2-phenylene, A = N, G = N, W = O, X = OMe, R² = Me, the floating double bond is attached to A and

| Y | Y | Y | Y |
|---|---|---|---|

Z = 3-CF₃-Ph

| Y | Y | Y | Y |
|---|---|---|---|
| CH₂O—N═C(CN)C(═O) | CH₂OC(═S)N(Me) | OC(═S)N(Me)C(═O) | (MeS)C═N—OCH₂ |
| CH═C(Cl)C(═O)O | CH₂O—N═C(Me)N(Me) | CH₂C(═O)O | O—N═C(SMe) |
| CH₂O—N═C(Cl) | CH₂O—N═C(Me)OCH₂ | CH₂CH₂C(═O)O | CH(c-Pr)O—N═C(Me) |
| C(═O) | CH₂O—N═C(Me)—N═N | N═C(Me)C(═O)O | (MeS)C═N—O |
| CH₂O—N═C(SMe) | CH₂O—N═C(Me)C(═O) | CH₂CH(c-Pr) | OC(═S)NHC(═O) |
| N═C(Cl)C(═O)O | CH═N—N(Me) | CH═C(c-Pr) | CH═C(CN)C(═O)O |
| CH₂O—N═C(SO₂Me) | CH₂N(COCH₃)N═C(Me) | CH₂OC(═O)N(c-Pr) | CH═C(Br)C(═O)O |
| CH═N—N═C(Me) | NH | N(Me) | CH═C(Cl)C(═O)NH |
| CH₂SC(Et)═N | CH₂O—N(Me)C(═O)N(Me) | CH═C(CN) | CH═C(Cl)C(═O)N(Me) |
| C≡C—C(═O)O | CH₂O—N(Me)C(═S)N(Me) | CH(c-Pr)O | CH═C(Cl)C(═O)S |
| CH₂SC(c-Pr)═N | CH₂O—N═C(SMe)N(Me) | SCH(c-Pr) | CH═C(Cl)C(═S)O |
| CH₂SC(Me)═N | CH₂O—N═C(SMe)OCH₂ | CH═N—OCH(c-Pr) | CH₂C(═O)NH |
| CH₂CH₂C(═O)NH | CH═C(Cl)C(═S)NH | C≡C—C(═O)NH | N═C(Cl)C(═O)NH |
| CH₂OC(═S)NH | CH₂SC(SMe)═N | CH₂O—N═C(NH₂) | CH₂O—N═C(NHMe) |
| CH₂OC(═O)O | CH₂OC(═S)O | CH₂OC(═O)S | CH₂OC(═S)S |
| CH₂SC(═O)N(Me) | CH₂SC(═O)NH | CH₂SC(═S)N(Me) | CH₂SC(═S)NH |
| CH₂SC(═O)O | CH₂SC(═S)O | CH₂SC(═O)S | CH₂SC(═S)S |
| CH₂SC(═NMe)S | CH₂N(Me)C(═O)N(Me) | CH₂O—N═C(Me)CH₂O | CH₂O—N═C(SMe)CH₂O |
| CH₂O—N═C(Me)CH₂S | CH₂O—N═C(SMe)CH₂S | OCH₂CH₂O—N═C(Me) | CH₂OC(Me)═C(CN) |
| CH₂N(Me)—N═C(Me) | | | |

Z = 3-Me₃Si-Ph

| Y | Y | Y | Y |
|---|---|---|---|
| CH₂O—N═C(CN)C(═O) | CH₂OC(═S)N(Me) | OC(═S)N(Me)C(═O) | (MeS)C═N—OCH₂ |
| CH═C(Cl)C(═O)O | CH₂O—N═C(Me)N(Me) | CH₂C(═O)O | O—N═C(SMe) |
| CH₂O—N═C(Cl) | CH₂O—N═C(Me)OCH₂ | CH₂CH₂C(═O)O | CH(c-Pr)O—N═C(Me) |
|  | CH₂O—N═C(Me)—N═N | N═C(Me)C(═O)O | (MeS)C═N—O |
| CH₂O—N═C(SMe) | CH₂O—N═C(Me)C(═O) | CH₂CH(c-Pr) | OC(═S)NHC(═O) |
| N═C(Cl)C(═O)O | CH═N—N(Me) | CH═C(c-Pr) | CH═C(CN)C(═O)O |
| CH₂O—N═C(SO₂Me) | CH₂N(COCH₃)N═C(Me) | CH₂OC(═O)N(c-Pr) | CH═C(Br)C(═O)O |
| CH═N—N═C(Me) |  |  | CH═C(Cl)C(═O)NH |
| CH₂SC(Et)═N | CH₂O—N(Me)C(═O)N(Me) | CH═C(CN) | CH═C(Cl)C(═O)N(Me) |
| C≡C—C(═O)O | CH₂O—N(Me)C(═S)N(Me) | CH(c-Pr)O | CH═C(Cl)C(═O)S |
| CH₂SC(c-Pr)═N | CH₂O—N═C(SMe)N(Me) | SCH(c-Pr) | CH═C(Cl)C(═S)O |
| CH₂SC(Me)═N | CH₂O—N═C(SMe)OCH₂ | CH═N—OCH(c-Pr) | CH₂C(═O)NH |
| CH₂CH₂C(═O)NH | CH═C(Cl)C(═S)NH | C≡C—C(═O)NH | N═C(Cl)C(═O)NH |
| CH₂OC(═S)NH | CH₂SC(SMe)═N | CH₂O—N═C(NH₂) | CH₂O—N═C(NHMe) |
| CH₂OC(═O)O | CH₂OC(═S)O | CH₂OC(═O)S | CH₂OC(═S)S |
| CH₂SC(═O)N(Me) | CH₂SC(═O)NH | CH₂SC(═S)N(Me) | CH₂SC(═S)NH |
| CH₂SC(═O)O | CH₂SC(═S)O | CH₂SC(═O)S | CH₂SC(═S)S |
| CH₂SC(═NMe)S | CH₂N(Me)C(═O)N(Me) | CH₂O—N═C(Me)CH₂O | CH₂O—N═C(SMe)CH₂O |
| CH₂O—N═C(Me)CH₂S | CH₂O—N═C(SMe)CH₂S | OCH₂CH₂O—N═C(Me) | CH₂OC(Me)═C(CN) |
| CH₂N(Me)—N═C(Me) | | | |

Z = Ph

| Y | Y | Y | Y |
|---|---|---|---|
| CH₂O—N═C(CN)C(═O) | CH₂OC(═S)N(Me) | OC(═S)N(Me)C(═O) | (MeS)C═N—OCH₂ |
| CH═C(Cl)C(═O)O | CH₂O—N═C(Me)N(Me) | CH₂C(═O)O | O—N═C(SMe) |
| CH₂O—N═C(Cl) | CH₂O—N═C(Me)OCH₂ | CH₂CH₂C(═O)O | CH(c-Pr)O—N═C(Me) |
| C(═O) | CH₂O—N═C(Me)—N═N | N═C(Me)C(═O)O | (MeS)C═N—O |
| CH₂O—N═C(SMe) | CH₂O—N═C(Me)C(═O) | CH₂CH(c-Pr) | OC(═S)NHC(═O) |
| N═C(Cl)C(═O)O | CH═N—N(Me) | CH═C(c-Pr) | CH═C(CN)C(═O)O |
| CH₂O—N═C(SO₂Me) | CH₂N(COCH₃)N═C(Me) | CH₂OC(═O)N(c-Pr) | CH═C(Br)C(═O)O |
| CH═N—N═C(Me) | NH | N(Me) | CH═C(Cl)C(═O)NH |
| CH₂SC(Et)═N | CH₂O—N(Me)C(═O)N(Me) | CH═C(CN) | CH═C(Cl)C(═O)N(Me) |
| C≡C—C(═O)O | CH₂O—N(Me)C(═S)N(Me) | CH(c-Pr)O | CH═C(Cl)C(═O)S |
| CH₂SC(c-Pr)═N | CH₂O—N═C(SMe)N(Me) | SCH(c-Pr) | CH═C(Cl)C(═S)O |
| CH₂SC(Me)═N | CH₂O—N═C(SMe)OCH₂ | CH═N—OCH(c-Pr) | CH₂C(═O)NH |
| CH₂CH₂C(═O)NH | CH═C(Cl)C(═S)NH | C≡C—C(═O)NH | N═C(Cl)C(═O)NH |
| CH₂OC(═S)NH | CH₂SC(SMe)═N | CH₂O—N═C(NH₂) | CH₂O—N═C(NHMe) |
| CH₂OC(═O)O | CH₂OC(═S)O | CH₂OC(═O)S | CH₂OC(═S)S |
| CH₂SC(═O)N(Me) | CH₂SC(═O)NH | CH₂SC(═S)N(Me) | CH₂SC(═S)NH |
| CH₂SC(═O)O | CH₂SC(═S)O | CH₂SC(═O)S | CH₂SC(═S)S |
| CH₂SC(═NMe)S | CH₂N(Me)C(═O)N(Me) | CH₂O—N═C(Me)CH₂O | CH₂O—N═C(SMe)CH₂O |
| CH₂O—N═C(Me)CH₂S | CH₂O—N═C(SMe)CH₂S | OCH₂CH₂O—N═C(Me) | CH₂OC(Me)═C(CN) |
| CH₂N(Me)—N═C(Me) | | | |

Z = t-Bu

| Y | Y | Y | Y |
|---|---|---|---|
| CH₂O—N═C(CN)C(═O) | CH₂OC(═S)N(Me) | OC(═S)N(Me)C(═O) | (MeS)C═N—OCH₂ |
| CH═C(Cl)C(═O)O | CH₂O—N═C(Me)N(Me) | CH₂C(═O)O | O—N═C(SMe) |
| CH₂O—N═C(Cl) | CH₂O—N═C(Me)OCH₂ | CH₂CH₂C(═O)O | CH(c-Pr)O—N═C(Me) |
| C(═O) | CH₂O—N═C(Me)—N═N | N═C(Me)C(═O)O | (MeS)C═N—O |
| CH₂O—N═C(SMe) | CH₂O—N═C(Me)C(═O) |  | OC(═S)NHC(═O) |
| N═C(Cl)C(═O)O | CH═N—N(Me) |  | CH═C(CN)C(═O)O |

TABLE 1-continued

Compounds of Formula I where E = 1,2-phenylene, A = N, G = N, W = O, X = OMe, R² = Me, the floating double bond is attached to A and

| Y | Y | Y | Y |
|---|---|---|---|
| CH₂O—N=C(SO₂Me) | CH₂N(COCH₃)N=C(Me) | CH₂OC(=O)N(c-Pr) | CH=C(Br)C(=O)O |
| CH=N—N=C(Me) | NH | N(Me) | CH=C(Cl)C(=O)NH |
| CH₂SC(Et)=N | CH₂O—N(Me)C(=O)N(Me) | | CH=C(Cl)C(=O)N(Me) |
| C≡C—C(=O)O | CH₂O—N(Me)C(=S)N(Me) | CH(c-Pr)O | CH=C(Cl)C(=O)S |
| CH₂SC(c-Pr)=N | CH₂O—N=C(SMe)N(Me) | | CH=C(Cl)C(=S)O |
| CH₂SC(Me)=N | CH₂O—N=C(SMe)OCH₂ | | CH₂C(=O)NH |
| CH₂CH₂C(=O)NH | CH=C(Cl)C(=S)NH | C≡C—C(=O)NH | N=C(Cl)C(=O)NH |
| CH₂OC(=S)NH | CH₂SC(SMe)=N | CH₂O—N=C(NH₂) | CH₂O—N=C(NHMe) |
| CH₂OC(=O)O | CH₂OC(=S)O | CH₂OC(=O)S | CH₂OC(=S)S |
| CH₂SC(=O)N(Me) | CH₂SC(=O)NH | CH₂SC(=S)N(Me) | CH₂SC(=S)NH |
| CH₂SC(=O)O | CH₂SC(=S)O | CH₂SC(=O)S | CH₂SC(=S)S |
| CH₂SC(=NMe)S | CH₂N(Me)C(=O)N(Me) | CH₂O—N=C(Me)CH₂O | CH₂O—N=C(SMe)CH₂O |
| CH₂O—N=C(Me)CH₂S | CH₂O—N=C(SMe)CH₂S | OCH₂CH₂O—N=C(Me) | CH₂OC(Me)=C(CN) |
| CH₂N(Me)—N=C(Me) | | | |

Z = 3,5-diCl-Ph

| Y | Y | Y | Y |
|---|---|---|---|
| CH₂O—N=C(CN)C(=O) | CH₂OC(=S)N(Me) | OC(=S)N(Me)C(=O) | (MeS)C=N—OCH₂ |
| CH=C(Cl)C(=O)O | CH₂O—N=C(Me)N(Me) | CH₂C(=O)O | O—N=C(SMe) |
| CH₂O—N=C(Cl) | CH₂O—N=C(Me)OCH₂ | CH₂CH₂C(=O)O | CH(c-Pr)O—N=C(Me) |
| C(=O) | CH₂O—N=C(Me)—N=N | N=C(Me)C(=O)O | (MeS)C=N—O |
| CH₂O—N=C(SMe) | CH₂O—N=C(Me)C(=O) | CH₂CH(c-Pr) | OC(=S)NHC(=O) |
| N=C(Cl)C(=O)O | CH=N—N(Me) | CH=C(c-Pr) | CH=C(CN)C(=O)O |
| CH₂O—N=C(SO₂Me) | CH₂N(COCH₃)N=C(Me) | CH₂OC(=O)N(c-Pr) | CH=C(Br)C(=O)O |
| CH=N—N=C(Me) | NH | N(Me) | CH=C(Cl)C(=O)NH |
| CH₂SC(Et)=N | CH₂O—N(Me)C(=O)N(Me) | CH=C(CN) | CH=C(Cl)C(=O)N(Me) |
| C≡C—C(=O)O | CH₂O—N(Me)C(=S)N(Me) | CH(c-Pr)O | CH=C(Cl)C(=O)S |
| CH₂SC(c-Pr)=N | CH₂O—N=C(SMe)N(Me) | SCH(c-Pr) | CH=C(Cl)C(=S)O |
| CH₂SC(Me)=N | CH₂O—N=C(SMe)OCH₂ | CH=N—OCH(c-Pr) | CH₂C(=O)NH |
| CH₂CH₂C(=O)NH | CH=C(Cl)C(=S)NH | C≡C—C(=O)NH | N=C(Cl)C(=O)NH |
| CH₂OC(=S)NH | CH₂SC(SMe)=N | CH₂O—N=C(NH₂) | CH₂O—N=C(NHMe) |
| CH₂OC(=O)O | CH₂OC(=S)O | CH₂OC(=O)S | CH₂OC(=S)S |
| CH₂SC(=O)N(Me) | CH₂SC(=O)NH | CH₂SC(=S)N(Me) | CH₂SC(=S)NH |
| CH₂SC(=O)O | CH₂SC(=S)O | CH₂SC(=O)S | CH₂SC(=S)S |
| CH₂SC(=NMe)S | CH₂N(Me)C(=O)N(Me) | CH₂O—N=C(Me)CH₂O | CH₂O—N=C(SMe)CH₂O |
| CH₂O—N=C(Me)CH₂S | CH₂O—N=C(SMe)CH₂S | OCH₂CH₂O—N=C(Me) | CH₂OC(Me)=C(CN) |
| CH₂N(Me)—N=C(Me) | | | |

TABLE 2

Compounds of Formula I where E = 1,2-phenylene, A = O, G = C, W = O, X = OMe, R² = Me, the floating double bond is attached to G and

| Y | Y | Y | Y |
|---|---|---|---|

Z = 3-CF₃-Ph

| Y | Y | Y | Y |
|---|---|---|---|
| CH₂O—N=C(CN)C(=O) | CH₂OC(=S)N(Me) | OC(=S)N(Me)C(=O) | (MeS)C=N—OCH₂ |
| CH=C(Cl)C(=O)O | CH₂O—N=C(Me)N(Me) | CH₂C(=O)O | O—N=C(SMe) |
| CH₂O—N=C(Cl) | CH₂O—N=C(Me)OCH₂ | CH₂CH₂C(=O)O | CH(c-Pr)O—N=C(Me) |
| C(=O) | CH₂O—N=C(Me)—N=N | N=C(Me)C(=O)O | (MeS)C=N—O |
| CH₂O—N=C(SMe) | CH₂O—N=C(Me)C(=O) | CH₂CH(c-Pr) | OC(=S)NHC(=O) |
| N=C(Cl)C(=O)O | CH=N—N(Me) | CH=C(c-Pr) | CH=C(CN)C(=O)O |
| CH₂O—N=C(SO₂Me) | CH₂N(COCH₃)N=C(Me) | CH₂OC(=O)N(c-Pr) | CH=C(Br)C(=O)O |
| CH=N—N=C(Me) | NH | N(Me) | CH=C(Cl)C(=O)NH |
| CH₂SC(Et)=N | CH₂O—N(Me)C(=O)N(Me) | CH=C(CN) | CH=C(Cl)C(=O)N(Me) |
| C≡C—C(=O)O | CH₂O—N(Me)C(=S)N(Me) | CH(c-Pr)O | CH=C(Cl)C(=O)S |
| CH₂SC(c-Pr)=N | CH₂O—N=C(SMe)N(Me) | SCH(c-Pr) | CH=C(Cl)C(=S)O |
| CH₂SC(Me)=N | CH₂O—N=C(SMe)OCH₂ | CH=N—OCH(c-Pr) | CH₂C(=O)NH |
| CH₂CH₂C(=O)NH | CH=C(Cl)C(=S)NH | C≡C—C(=O)NH | N=C(Cl)C(=O)NH |
| CH₂OC(=S)NH | CH₂SC(SMe)=N | CH₂O—N=C(NH₂) | CH₂O—N=C(NHMe) |
| CH₂OC(=O)O | CH₂OC(=S)O | CH₂OC(=O)S | CH₂OC(=S)S |
| CH₂SC(=O)N(Me) | CH₂SC(=O)NH | CH₂SC(=S)N(Me) | CH₂SC(=S)NH |
| CH₂SC(=O)O | CH₂SC(=S)O | CH₂SC(=O)S | CH₂SC(=S)S |
| CH₂SC(=NMe)S | CH₂N(Me)C(=O)N(Me) | CH₂O—N=C(Me)CH₂O | CH₂O—N=C(SMe)CH₂O |
| CH₂O—N=C(Me)CH₂S | CH₂O—N=C(SMe)CH₂S | OCH₂CH₂O—N=C(Me) | CH₂OC(Me)=C(CN) |
| CH₂N(Me)—N=C(Me) | | | |

Z = 3-Me₃Si-Ph

| Y | Y | Y | Y |
|---|---|---|---|
| CH₂O—N=C(CN)C(=O) | CH₂OC(=S)N(Me) | OC(=S)N(Me)C(=O) | (MeS)C=N—OCH₂ |
| CH=C(Cl)C(=O)O | CH₂O—N=C(Me)N(Me) | CH₂C(=O)O | O—N=C(SMe) |
| CH₂O—N=C(Cl) | CH₂O—N=C(Me)OCH₂ | CH₂CH₂C(=O)O | CH(c-Pr)O—N=C(Me) |

TABLE 2-continued

Compounds of Formula I where E = 1,2-phenylene, A = O, G = C, W = O, X = OMe, R² = Me, the floating double bond is attached to G and

| Y | Y | Y | Y |
|---|---|---|---|
|  | CH₂O—N=C(Me)—N=N | N=C(Me)C(=O)O | (MeS)C=N—O |
| CH₂O—N=C(SMe) | CH₂O—N=C(Me)C(=O) | CH₂CH(c-Pr) | OC(=S)NHC(=O) |
| N=C(Cl)C(=O)O | CH=N—N(Me) | CH=C(c-Pr) | CH=C(CN)C(=O)O |
| CH₂O—N=C(SO₂Me) | CH₂N(COCH₃)N=C(Me) | CH₂OC(=O)N(c-Pr) | CH=C(Br)C(=O)O |
| CH=N—N=C(Me) |  |  | CH=C(Cl)C(=O)NH |
| CH₂SC(Et)=N | CH₂O—N(Me)C(=O)N(Me) | CH=C(CN) | CH=C(Cl)C(=O)N(Me) |
| C≡C—C(=O)O | CH₂O—N(Me)C(=S)N(Me) | CH(c-Pr)O | CH=C(Cl)C(=O)S |
| CH₂SC(c-Pr)=N | CH₂O—N=C(SMe)N(Me) | SCH(c-Pr) | CH=C(Cl)C(=S)O |
| CH₂SC(Me)=N | CH₂O—N=C(SMe)OCH₂ | CH=N—OCH(c-Pr) | CH₂C(=O)NH |
| CH₂CH₂C(=O)NH | CH=C(Cl)C(=S)NH | C≡C—C(=O)NH | N=C(Cl)C(=O)NH |
| CH₂OC(=S)NH | CH₂SC(SMe)=N | CH₂O—N=C(NH₂) | CH₂O—N=C(NHMe) |
| CH₂OC(=O)O | CH₂OC(=S)O | CH₂OC(=O)S | CH₂OC(=S)S |
| CH₂SC(=O)N(Me) | CH₂SC(=O)NH | CH₂SC(=S)N(Me) | CH₂SC(=S)NH |
| CH₂SC(=O)O | CH₂SC(=S)O | CH₂SC(=O)S | CH₂SC(=S)S |
| CH₂SC(=NMe)S | CH₂N(Me)C(=O)N(Me) | CH₂O—N=C(Me)CH₂O | CH₂O—N=C(SMe)CH₂O |
| CH₂O—N=C(Me)CH₂S | CH₂O—N=C(SMe)CH₂S | OCH₂CH₂O—N=C(Me) | CH₂OC(Me)=C(CN) |
| CH₂N(Me)—N=C(Me) |  |  |  |

Z = Ph

| Y | Y | Y | Y |
|---|---|---|---|
| CH₂O—N=C(CN)C(=O) | CH₂OC(=S)N(Me) | OC(=S)N(Me)C(=O) | (MeS)C=N—OCH₂ |
| CH=C(Cl)C(=O)O | CH₂O—N=C(Me)N(Me) | CH₂C(=O)O | O—N=C(SMe) |
| CH₂O—N=C(Cl) | CH₂O—N=C(Me)OCH₂ | CH₂CH₂C(=O)O | CH(c-Pr)O—N=C(Me) |
| C(=O) | CH₂O—N=C(Me)—N=N | N=C(Me)C(=O)O | (MeS)C=N—O |
| CH₂O—N=C(SMe) | CH₂O—N=C(Me)C(=O) | CH₂CH(c-Pr) | OC(=S)NHC(=O) |
| N=C(Cl)C(=O)O | CH=N—N(Me) | CH=C(c-Pr) | CH=C(CN)C(=O)O |
| CH₂O—N=C(SO₂Me) | CH₂N(COCH₃)N=C(Me) | CH₂OC(=O)N(c-Pr) | CH=C(Br)C(=O)O |
| CH=N—N=C(Me) | NH | N(Me) | CH=C(Cl)C(=O)NH |
| CH₂SC(Et)=N | CH₂O—N(Me)C(=O)N(Me) | CH=C(CN) | CH=C(Cl)C(=O)N(Me) |
| C≡C—C(=O)O | CH₂O—N(Me)C(=S)N(Me) | CH(c-Pr)O | CH=C(Cl)C(=O)S |
| CH₂SC(c-Pr)=N | CH₂O—N=C(SMe)N(Me) | SCH(c-Pr) | CH=C(Cl)C(=S)O |
| CH₂SC(Me)=N | CH₂O—N=C(SMe)OCH₂ | CH=N—OCH(c-Pr) | CH₂C(=O)NH |
| CH₂CH₂C(=O)NH | CH=C(Cl)C(=S)NH | C≡C—C(=O)NH | N=C(Cl)C(=O)NH |
| CH₂OC(=S)NH | CH₂SC(SMe)=N | CH₂O—N=C(NH₂) | CH₂O—N=C(NHMe) |
| CH₂OC(=O)O | CH₂OC(=S)O | CH₂OC(=O)S | CH₂OC(=S)S |
| CH₂SC(=O)N(Me) | CH₂SC(=O)NH | CH₂SC(=S)N(Me) | CH₂SC(=S)NH |
| CH₂SC(=O)O | CH₂SC(=S)O | CH₂SC(=O)S | CH₂SC(=S)S |
| CH₂SC(=NMe)S | CH₂N(Me)C(=O)N(Me) | CH₂O—N=C(Me)CH₂O | CH₂O—N=C(SMe)CH₂O |
| CH₂O—N=C(Me)CH₂S | CH₂O—N=C(SMe)CH₂S | OCH₂CH₂O—N=C(Me) | CH₂OC(Me)=C(CN) |
| CH₂N(Me)—N=C(Me) |  |  |  |

Z = t-Bu

| Y | Y | Y | Y |
|---|---|---|---|
| CH₂O—N=C(CN)C(=O) | CH₂OC(=S)N(Me) | OC(=S)N(Me)C(=O) | (MeS)C=N—OCH₂ |
| CH=C(Cl)C(=O)O | CH₂O—N=C(Me)N(Me) | CH₂C(=O)O | O—N=C(SMe) |
| CH₂O—N=C(Cl) | CH₂O—N=C(Me)OCH₂ | CH₂CH₂C(=O)O | CH(c-Pr)O—N=C(Me) |
| C(=O) | CH₂O—N=C(Me)—N=N | N=C(Me)C(=O)O | (MeS)C=N—O |
| CH₂O—N=C(SMe) | CH₂O—N=C(Me)C(=O) |  | OC(=S)NHC(=O) |
| N=C(Cl)C(=O)O | CH=N—N(Me) |  | CH=C(CN)C(=O)O |
| CH₂O—N=C(SO₂Me) | CH₂N(COCH₃)N=C(Me) | CH₂OC(=O)N(c-Pr) | CH=C(Br)C(=O)O |
| CH=N—N=C(Me) | NH | N(Me) | CH=C(Cl)C(=O)NH |
| CH₂SC(Et)=N | CH₂O—N(Me)C(=O)N(Me) |  | CH=C(Cl)C(=O)N(Me) |
| C≡C—C(=O)O | CH₂O—N(Me)C(=S)N(Me) | CH(c-Pr)O | CH=C(Cl)C(=O)S |
| CH₂SC(c-Pr)=N | CH₂O—N=C(SMe)N(Me) |  | CH=C(Cl)C(=S)O |
| CH₂SC(Me)=N | CH₂O—N=C(SMe)OCH₂ |  | CH₂C(=O)NH |
| CH₂CH₂C(=O)NH | CH=C(Cl)C(=S)NH | C≡C—C(=O)NH | N=C(Cl)C(=O)NH |
| CH₂OC(=S)NH | CH₂SC(SMe)=N | CH₂O—N=C(NH₂) | CH₂O—N=C(NHMe) |
| CH₂OC(=O)O | CH₂OC(=S)O | CH₂OC(=O)S | CH₂OC(=S)S |
| CH₂SC(=O)N(Me) | CH₂SC(=O)NH | CH₂SC(=S)N(Me) | CH₂SC(=S)NH |
| CH₂SC(=O)O | CH₂SC(=S)O | CH₂SC(=O)S | CH₂SC(=S)S |
| CH₂SC(=NMe)S | CH₂N(Me)C(=O)N(Me) | CH₂O—N=C(Me)CH₂O | CH₂O—N=C(SMe)CH₂O |
| CH₂O—N=C(Me)CH₂S | CH₂O—N=C(SMe)CH₂S | OCH₂CH₂O—N=C(Me) | CH₂OC(Me)=C(CN) |
| CH₂N(Me)—N=C(Me) |  |  |  |

Z = 3,5-diCl-Ph

| Y | Y | Y | Y |
|---|---|---|---|
| CH₂O—N=C(CN)C(=O) | CH₂OC(=S)N(Me) | OC(=S)N(Me)C(=O) | (MeS)C=N—OCH₂ |
| CH=C(Cl)C(=O)O | CH₂O—N=C(Me)N(Me) | CH₂C(=O)O | O—N=C(SMe) |
| CH₂O—N=C(Cl) | CH₂O—N=C(Me)OCH₂ | CH₂CH₂C(=O)O | CH(c-Pr)O—N=C(Me) |
| C(=O) | CH₂O—N=C(Me)—N=N | N=C(Me)C(=O)O | (MeS)C=N—O |
| CH₂O—N=C(SMe) | CH₂O—N=C(Me)C(=O) | CH₂CH(c-Pr) | OC(=S)NHC(=O) |
| N=C(Cl)C(=O)O | CH=N—N(Me) | CH=C(c-Pr) | CH=C(CN)C(=O)O |
| CH₂O—N=C(SO₂Me) | CH₂N(COCH₃)N=C(Me) | CH₂OC(=O)N(c-Pr) | CH=C(Br)C(=O)O |
| CH=N—N=C(Me) | NH | N(Me) | CH=C(Cl)C(=O)NH |
| CH₂SC(Et)=N | CH₂O—N(Me)C(=O)N(Me) | CH=C(CN) | CH=C(Cl)C(=O)N(Me) |
| C≡C—C(=O)O | CH₂O—N(Me)C(=S)N(Me) | CH(c-Pr)O | CH=C(Cl)C(=O)S |
| CH₂SC(c-Pr)=N | CH₂O—N=C(SMe)N(Me) | SCH(c-Pr) | CH=C(Cl)C(=S)O |

TABLE 2-continued

Compounds of Formula I where E = 1,2-phenylene, A = O, G = C, W = O, X = OMe, $R^2$ = Me, the floating double bond is attached to G and

| Y | Y | Y | Y |
|---|---|---|---|
| $CH_2SC(Me)=N$ | $CH_2O-N=C(SMe)OCH_2$ | $CH=N-OCH(c-Pr)$ | $CH_2C(=O)NH$ |
| $CH_2CH_2C(=O)NH$ | $CH=C(Cl)C(=S)NH$ | $C\equiv C-C(=O)NH$ | $N=C(Cl)C(=O)NH$ |
| $CH_2OC(=S)NH$ | $CH_2SC(SMe)=N$ | $CH_2O-N=C(NH_2)$ | $CH_2O-N=C(NHMe)$ |
| $CH_2OC(=O)O$ | $CH_2OC(=S)O$ | $CH_2OC(=O)S$ | $CH_2OC(=S)S$ |
| $CH_2SC(=O)N(Me)$ | $CH_2SC(=O)NH$ | $CH_2SC(=S)N(Me)$ | $CH_2SC(=S)NH$ |
| $CH_2SC(=O)O$ | $CH_2SC(=S)O$ | $CH_2SC(=O)S$ | $CH_2SC(=S)S$ |
| $CH_2SC(=NMe)S$ | $CH_2N(Me)C(=O)N(Me)$ | $CH_2O-N=C(Me)CH_2O$ | $CH_2O-N=C(SMe)CH_2O$ |
| $CH_2O-N=C(Me)CH_2S$ | $CH_2O-N=C(SMe)CH_2S$ | $OCH_2CH_2O-N=C(Me)$ | $CH_2OC(Me)=C(CN)$ |
| $CH_2N(Me)-N=C(Me)$ | | | |

TABLE 3

Compounds of Formula I where E = 1,2-phenylene, A = N, G = N, W = O, X = OMe, $R^2$ = Me, the floating double bond is attached to A and

| Z | Z | Z | Z |
|---|---|---|---|
| \multicolumn{4}{c}{Y = CH=C(Cl)C(=O)O} | | | |
| 2-Br-Ph | i-Pr | $PhC\equiv CCH_2$ | 4-$Me_3$Ge-2-pyridinyl |
| 2-CN-Ph | c-pentyl | 2-Et-Ph | 4-$CF_3$-2-nap |
| 2-$CF_3$-Ph | $PhCH_2$ | 2-Cl-Ph | (c-Pr)$CH_2$ |
| c-hexyl | 1-phenylethyl | 2,4,6-triCl-Ph | 3-pentynyl |
| $PhCH_2CH_2$ | (4-Cl-Ph)$CH_2$ | 3-PhO-Ph | 4-octenyl |
| (2-CN-Ph)$CH_2$ | (3-F-Ph)$CH_2$ | 6-Ph-2-pyridinyl | hexyl |
| $CF_3CH_2$ | 2,5-diMe-Ph | 6-$CF_3$-2-pyridinyl | 4-(PhO)-c-hexyl |
| 2-MeS-Ph | $HC\equiv CCH_2$ | 4-Me-2-pyrimidinyl | 2-$CF_3$O-Ph |
| 4-Cl-Ph | $H_2C=CHCH_2$ | 6-MeO-4-pyrimidinyl | 3-(2-Et-PhO)-Ph |
| 3-Me-Ph | $PhCH=CHCH_2$ | 2-Ph-4-thiazolyl | 6-$CF_3$-4-pyrimidinyl |
| | 2-Me-Ph | 3-$OCF_2$H-Ph | $PhCH=CHCH(Me)$ |
| 3-Cl-2-Me-Ph | 2-Me-4-Cl-Ph | 5-Me-2-nap | 4,6-diMe-O-2-pyrimidinyl |
| 3-t-Bu-Ph | | 6-$Me_3$Si-2-nap | 3-(2-Me-PhO)-Ph |
| 3-F-Ph | 3,5-di$CF_3$-Ph | 7-$OCF_3$-2-nap | 2-F-Ph |
| 4-$CF_3$-Ph | 2-MeO-Ph | 4-PhO-2-pyridinyl | 4-Me-Ph |
| 3,4-diCl-Ph | 3-$CF_3$O-Ph | 4-EtO-2-pyrimidinyl | 4-MeO-2-pyrimidinyl |
| 3,4-di$CF_3$-Ph | 3-Et-Ph | 4-$CF_3$-2-pyridinyl | 5-Me-2-furanyl |
| 3-EtO-Ph | 3-Ph-Ph | 4-$CF_3$-2-pyrimidinyl | 4-Ph-Ph |
| | 3,4-diMe-Ph | 6-$CF_3$-2-pyrazinyl | 2-I-Ph |
| 2-nap | 3,5-diMe-Ph | 5-$CF_3$-3-pyridinyl | 2,5-diMe-3-thienyl |
| 3-$SF_5$-Ph | 3-MeS-Ph | 4-t-Bu-2-nap | 3-MeO-6-pyridazinyl |
| | | 3,5-diBr-Ph | 5-PhO-2-pyrimidinyl |
| 4-F-3-$CF_3$-Ph | 4-$Me_3$Si-Ph | 4-t-Bu-2-pyridinyl | 6-PhO-2-pyridinyl |
| 5-F-3-$CF_3$-Ph | 3-$Me_3$Ge-Ph | 4-Ph-2-pyridinyl | (4-Br-Ph)$CH_2$ |
| i-Bu | 4-$Me_3$Ge-Ph | 4-$Me_3$Si-2-pyridinyl | n-Bu |
| \multicolumn{4}{c}{Y = CH=N-N=C(Me)} | | | |
| 2-Br-Ph | i-Pr | $PhC\equiv CCH_2$ | 4-$Me_3$Ge-2-pyridinyl |
| 2-CN-Ph | c-pentyl | 2-Et-Ph | 4-$CF_3$-2-nap |
| 2-$CF_3$-Ph | $PhCH_2$ | 2-Cl-Ph | (c-Pr)$CH_2$ |
| c-hexyl | 1-phenylethyl | 2,4,6-triCl-Ph | 3-pentynyl |
| $PhCH_2CH_2$ | (4-Cl-Ph)$CH_2$ | 3-PhO-Ph | 4-octenyl |
| (2-CN-Ph)$CH_2$ | (3-F-Ph)$CH_2$ | 6-Ph-2-pyridinyl | hexyl |
| $CF_3CH_2$ | 2,5-diMe-Ph | 6-$CF_3$-2-pyridinyl | 4-(PhO)-c-hexyl |
| 2-MeS-Ph | $HC\equiv CCH_2$ | 4-Me-2-pyrimidinyl | 2-$CF_3$O-Ph |
| 4-Cl-Ph | $H_2C=CHCH_2$ | 6-MeO-4-pyrimidinyl | 3-(2-Et-PhO)-Ph |
| 3-Me-Ph | $PhCH=CHCH_2$ | 2-Ph-4-thiazolyl | 6-$CF_3$-4-pyrimidinyl |
| | 2-Me-Ph | 3-$OCF_2$H-Ph | $PhCH=CHCH(Me)$ |
| 3-Cl-2-Me-Ph | 2-Me-4-Cl-Ph | 5-Me-2-nap | 4,6-diMe-O-2-pyrimidinyl |
| 3-t-Bu-Ph | | 6-$Me_3$Si-2-nap | 3-(2-Me-PhO)-Ph |
| 3-F-Ph | 3,5-di$CF_3$-Ph | 7-$OCF_3$-2-nap | 2-F-Ph |
| 4-$CF_3$-Ph | 2-MeO-Ph | 4-PhO-2-pyridinyl | 4-Me-Ph |
| 3,4-diCl-Ph | 3-$CF_3$O-Ph | 4-EtO-2-pyrimidinyl | 4-MeO-2-pyrimidinyl |
| 3,4-di$CF_3$-Ph | 3-Et-Ph | 4-$CF_3$-2-pyridinyl | 5-Me-2-furanyl |
| 3-EtO-Ph | 3-Ph-Ph | 4-$CF_3$-2-pyrimidinyl | 4-Ph-Ph |
| | 3,4-diMe-Ph | 6-$CF_3$-2-pyrazinyl | 2-I-Ph |
| 2-nap | 3,5-diMe-Ph | 5-$CF_3$-3-pyridinyl | 2,5-diMe-3-thienyl |
| 3-$SF_5$-Ph | 3-MeS-Ph | 4-t-Bu-2-nap | 3-MeO-6-pyridazinyl |
| | | 3,5-diBr-Ph | 5-PhO-2-pyrimidinyl |
| 4-F-3-$CF_3$-Ph | 4-$Me_3$Si-Ph | 4-t-Bu-2-pyridinyl | 6-PhO-2-pyridinyl |
| 5-F-3-$CF_3$-Ph | 3-$Me_3$Ge-Ph | 4-Ph-2-pyridinyl | (4-Br-Ph)$CH_2$ |

TABLE 3-continued

Compounds of Formula I where E = 1,2-phenylene,
A = N, G = N, W = O, X = OMe, R² = Me,
the floating double bond is attached to A and

| Z | Z | Z | Z |
|---|---|---|---|
| i-Bu | 4-Me₃Ge-Ph | 4-Me₃Si-2-pyridinyl | n-Bu |

Y = CH₂SC(Et)=N

| 2-Br-Ph | i-Pr | PhC≡CCH₂ | 4-Me₃Ge-2-pyridinyl |
| 2-CN-Ph | c-pentyl | 2-Et-Ph | 4-CF₃-2-nap |
| 2-CF₃-Ph | PhCH₂ | 2-Cl-Ph | (c-Pr)CH₂ |
| c-hexyl | 1-phenylethyl | 2,4,6-triCl-Ph | 3-pentynyl |
| PhCH₂CH₂ | (4-Cl-Ph)CH₂ | 3-PhO-Ph | 4-octenyl |
| (2-CN-Ph)CH₂ | (3-F-Ph)CH₂ | 6-Ph-2-pyridinyl | hexyl |
| CF₃CH₂ | 2,5-diMe-Ph | 6-CF₃-2-pyridinyl | 4-(PhO)-c-hexyl |
| 2-MeS-Ph | HC≡CCH₂ | 4-Me-2-pyrimidinyl | 2-CF₃O-Ph |
| 4-Cl-Ph | H₂C=CHCH₂ | 6-MeO-4-pyrimidinyl | 3-(2-Et-PhO)-Ph |
| 3-Me-Ph | PhCH=CHCH₂ | 2-Ph-4-thiazolyl | 6-CF₃-4-pyrimidinyl |
|  | 2-Me-Ph | 3-OCF₂H-Ph | PhCH=CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-Me₃Si-2-nap | 3-(2-Me-PhO)-Ph |
| 3-F-Ph | 3,5-diCF₃-Ph | 7-OCF₃-2-nap | 2-F-Ph |
| 4-CF₃-Ph | 2-MeO-Ph | 4-PhO-2-pyridinyl | 4-Me-Ph |
| 3,4-diCl-Ph | 3-CF₃O-Ph | 4-EtO-2-pyrimidinyl | 4-MeO-2-pyrimidinyl |
| 3,4-diCF₃-Ph | 3-Et-Ph | 4-CF₃-2-pyridinyl | 5-Me-2-furanyl |
| 3-EtO-Ph | 3-Ph-Ph | 4-CF₃-2-pyrimidinyl | 4-Ph-Ph |
|  | 3,4-diMe-Ph | 6-CF₃-2-pyrazinyl | 2-I-Ph |
| 2-nap | 3,5-diMe-Ph | 5-CF₃-3-pyridinyl | 2,5-diMe-3-thienyl |
| 3-SF₅-Ph | 3-MeS-Ph | 4-t-Bu-2-nap | 3-MeO-6-pyridazinyl |
|  |  | 3,5-diBr-Ph | 5-PhO-2-pyrimidinyl |
| 4-F-3-CF₃-Ph | 4-Me₃Si-Ph | 4-t-Bu-2-pyridinyl | 6-PhO-2-pyridinyl |
| 5-F-3-CF₃-Ph | 3-Me₃Ge-Ph | 4-Ph-2-pyridinyl | (4-Br-Ph)CH₂ |
| i-Bu | 4-Me₃Ge-Ph | 4-Me₃Si-2-pyridinyl | n-Bu |

Y = CH₂O—N=C(SMe)

| 2-Br-Ph | i-Pr | PhC≡CCH₂ | 4-Me₃Ge-2-pyridinyl |
| 2-CN-Ph | c-pentyl | 2-Et-Ph |  |
| 2-CF₃-Ph | PhCH₂ | 2-Cl-Ph | (c-Pr)CH₂ |
| c-hexyl | 1-phenylethyl | 2,4,6-triCl-Ph | 3-pentynyl |
| PhCH₂CH₂ | (4-Cl-Ph)CH₂ | 3-PhO-Ph | 4-octenyl |
| (2-CN-Ph)CH₂ | (3-F-Ph)CH₂ | 6-Ph-2-pyridinyl | hexyl |
| CF₃CH₂ | 2,5-diMe-Ph | 6-CF₃-2-pyridinyl | 4-(PhO)-c-hexyl |
| 2-MeS-Ph | HC≡CCH₂ | 4-Me-2-pyrimidinyl | 2-CF₃O-Ph |
| 4-Cl-Ph | H₂C=CHCH₂ | 6-MeO-4-pyrimidinyl | 3-(2-Et-PhO)-Ph |
| 3-Me-Ph | PhCH=CHCH₂ | 2-Ph-4-thiazolyl | 6-CF₃-4-pyrimidinyl |
|  | 2-Me-Ph | 3-OCF₂H-Ph | PhCH=CHCH(Me) |
| 3-Cl-2-Me-Ph | 2-Me-4-Cl-Ph |  | 4,6-diMe-O-2-pyrimidinyl |
| 3-t-Bu-Ph |  |  | 3-(2-Me-PhO)-Ph |
| 3-F-Ph | 3,5-diCF₃-Ph |  | 2-F-Ph |
| 4-CF₃-Ph | 2-MeO-Ph | 4-PhO-2-pyridinyl | 4-Me-Ph |
| 3,4-diCl-Ph | 3-CF₃O-Ph | 4-EtO-2-pyrimidinyl | 4-MeO-2-pyrimidinyl |
| 3,4-diCF₃-Ph | 3-Et-Ph | 4-CF₃-2-pyridinyl | 5-Me-2-furanyl |
| 3-EtO-Ph | 3-Ph-Ph | 4-CF₃-2-pyrimidinyl | 4-Ph-Ph |
|  | 3,4-diMe-Ph | 6-CF₃-2-pyrazinyl | 2-I-Ph |
|  | 3,5-diMe-Ph | 5-CF₃-3-pyridinyl | 2,5-diMe-3-thienyl |
| 3-SF₅-Ph | 3-MeS-Ph |  | 3-MeO-6-pyridazinyl |
|  |  | 3,5-diBr-Ph | 5-PhO-2-pyrimidinyl |
| 4-F-3-CF₃-Ph | 4-Me₃Si-Ph | 4-t-Bu-2-pyridinyl | 6-PhO-2-pyridinyl |
| 5-F-3-CF₃-Ph | 3-Me₃Ge-Ph | 4-Ph-2-pyridinyl | (4-Br-Ph)CH₂ |
| i-Bu | 4-Me₃Ge-Ph | 4-Me₃Si-2-pyridinyl | n-Bu |

Y = CH₂O—N=C(Me)CH₂S

| 2-Br-Ph | i-Pr | PhC≡CCH₂ | 4-Me₃Ge-2-pyridinyl |
| 2-CN-Ph | c-pentyl | 2-Et-Ph | 4-CF₃-2-nap |
| 2-CF₃-Ph | PhCH₂ | 2-Cl-Ph | (c-Pr)CH₂ |
| c-hexyl | 1-phenylethyl | 2,4,6-triCl-Ph | 3-pentynyl |
| PhCH₂CH₂ | (4-Cl-Ph)CH₂ | 3-PhO-Ph | 4-octenyl |
| (2-CN-Ph)CH₂ | (3-F-Ph)CH₂ | 6-Ph-2-pyridinyl | hexyl |
| CF₃CH₂ | 2,5-diMe-Ph | 6-CF₃-2-pyridinyl | 4-(PhO)-c-hexyl |
| 2-MeS-Ph | HC≡CCH₂ | 4-Me-2-pyrimidinyl | 2-CF₃O-Ph |
| 4-Cl-Ph | H₂C=CHCH₂ | 6-MeO-4-pyrimidinyl | 3-(2-Et-PhO)-Ph |
| 3-Me-Ph | PhCH=CHCH₂ | 2-Ph-4-thiazolyl | 6-CF₃-4-pyrimidinyl |
|  | 2-Me-Ph | 3-OCF₂H-Ph | PhCH=CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-Me₃Si-2-nap | 3-(2-Me-PhO)-Ph |
| 3-F-Ph | 3,5-diCF₃-Ph | 7-OCF₃-2-nap | 2-F-Ph |
| 4-CF₃-Ph | 2-MeO-Ph | 4-PhO-2-pyridinyl | 4-Me-Ph |
| 3,4-diCl-Ph | 3-CF₃O-Ph | 4-EtO-2-pyrimidinyl | 4-MeO-2-pyrimidinyl |

TABLE 3-continued

Compounds of Formula I where E = 1,2-phenylene,
A = N, G = N, W = O, X = OMe, $R^2$ = Me,
the floating double bond is attached to A and

| Z | Z | Z | Z |
|---|---|---|---|
| 3,4-diCF$_3$-Ph | 3-Et-Ph | 4-CF$_3$-2-pyridinyl | 5-Me-2-furanyl |
| 3-EtO-Ph | 3-Ph-Ph | 4-CF$_3$-2-pyrimidinyl | 4-Ph-Ph |
|  | 3,4-diMe-Ph | 6-CF$_3$-2-pyrazinyl | 2-I-Ph |
| 2-nap | 3,5-diMe-Ph | 5-CF$_3$-3-pyridinyl | 2,5-diMe-3-thienyl |
| 3-SF$_5$-Ph | 3-MeS-Ph | 4-t-Bu-2-nap | 3-MeO-6-pyridazinyl |
|  |  | 3,5-diBr-Ph | 5-PhO-2-pyrimidinyl |
| 4-F-3-CF$_3$-Ph | 4-Me$_3$Si-Ph | 4-t-Bu-2-pyridinyl | 6-PhO-2-pyridinyl |
| 5-F-3-CF$_3$-Ph | 3-Me$_3$Ge-Ph | 4-Ph-2-pyridinyl | (4-Br-Ph)CH$_2$ |
| i-Bu | 4-Me$_3$Ge-Ph | 4-Me$_3$Si-2-pyridinyl | n-Bu |

Y = CH$_2$O—N═C(Me)CH$_2$O

| Z | Z | Z | Z |
|---|---|---|---|
| 2-Br-Ph | i-Pr | PhC≡CCH$_2$ | 4-Me$_3$Ge-2-pyridinyl |
| 2-CN-Ph | c-pentyl | 2-Et-Ph | 4-CF$_3$-2-nap |
| 2-CF$_3$-Ph | PhCH$_2$ | 2-Cl-Ph | (c-Pr)CH$_2$ |
| c-hexyl | 1-phenylethyl | 2,4,6-triCl-Ph | 3-pentynyl |
| PhCH$_2$CH$_2$ | (4-Cl-Ph)CH$_2$ | 3-PhO-Ph | 4-octenyl |
| (2-CN-Ph)CH$_2$ | (3-F-Ph)CH$_2$ | 6-Ph-2-pyridinyl | hexyl |
| CF$_3$CH$_2$ | 2,5-diMe-Ph | 6-CF$_3$-2-pyridinyl | 4-(PhO)-c-hexyl |
| 2-MeS-Ph | HC≡CCH$_2$ | 4-Me-2-pyrimidinyl | 2-CF$_3$O-Ph |
| 4-Cl-Ph | H$_2$C═CHCH$_2$ | 6-MeO-4-pyrimidinyl | 3-(2-Et-PhO)-Ph |
| 3-Me-Ph | PhCH═CHCH$_2$ | 2-Ph-4-thiazolyl | 6-CF$_3$-4-pyrimidinyl |
|  | 2-Me-Ph | 3-OCF$_2$H-Ph | PhCH═CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-Me$_3$Si-2-nap | 3-(2-Me-PhO)-Ph |
| 3-F-Ph | 3,5-diCF$_3$-Ph | 7-OCF$_3$-2-nap | 2-F-Ph |
| 4-CF$_3$-Ph | 2-MeO-Ph | 4-PhO-2-pyridinyl | 4-Me-Ph |
| 3,4-diCl-Ph | 3-CF$_3$O-Ph | 4-EtO-2-pyrimidinyl | 4-MeO-2-pyrimidinyl |
| 3,4-diCF$_3$-Ph | 3-Et-Ph | 4-CF$_3$-2-pyridinyl | 5-Me-2-furanyl |
| 3-EtO-Ph | 3-Ph-Ph | 4-CF$_3$-2-pyrimidinyl | 4-Ph-Ph |
|  | 3,4-diMe-Ph | 6-CF$_3$-2-pyrazinyl | 2-I-Ph |
| 2-nap | 3,5-diMe-Ph | 5-CF$_3$-3-pyridinyl | 2,5-diMe-3-thienyl |
| 3-SF$_5$-Ph | 3-MeS-Ph | 4-t-Bu-2-nap | 3-MeO-6-pyridazinyl |
|  |  | 3,5-diBr-Ph | 5-PhO-2-pyrimidinyl |
| 4-F-3-CF$_3$-Ph | 4-Me$_3$Si-Ph | 4-t-Bu-2-pyridinyl | 6-PhO-2-pyridinyl |
| 5-F-3-CF$_3$-Ph | 3-Me$_3$Ge-Ph | 4-Ph-2-pyridinyl | (4-Br-Ph)CH$_2$ |
| i-Bu | 4-Me$_3$Ge-Ph | 4-Me$_3$Si-2-pyridinyl | n-Bu |

Y = CH═N—N(Me)

| Z | Z | Z | Z |
|---|---|---|---|
| 2-Br-Ph | i-Pr | PhC≡CCH$_2$ | 4-Me$_3$Ge-2-pyridinyl |
| 2-CN-Ph | c-pentyl | 2-Et-Ph | 4-CF$_3$-2-nap |
| 2-CF$_3$-Ph | PhCH$_2$ | 2-Cl-Ph | (c-Pr)CH$_2$ |
| c-hexyl | 1-phenylethyl | 2,4,6-triCl-Ph | 3-pentynyl |
| PhCH$_2$CH$_2$ | (4-Cl-Ph)CH$_2$ | 3-PhO-Ph | 4-octenyl |
| (2-CN-Ph)CH$_2$ | (3-F-Ph)CH$_2$ | 6-Ph-2-pyridinyl | hexyl |
| CF$_3$CH$_2$ | 2,5-diMe-Ph | 6-CF$_3$-2-pyridinyl | 4-(PhO)-c-hexyl |
| 2-MeS-Ph | HC≡CCH$_2$ | 4-Me-2-pyrimidinyl | 2-CF$_3$O-Ph |
| 4-Cl-Ph | H$_2$C═CHCH$_2$ | 6-MeO-4-pyrimidinyl | 3-(2-Et-PhO)-Ph |
| 3-Me-Ph | PhCH═CHCH$_2$ | 2-Ph-4-thiazolyl | 6-CF$_3$-4-pyrimidinyl |
|  | 2-Me-Ph | 3-OCF$_2$H-Ph | PhCH═CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-Me$_3$Si-2-nap | 3-(2-Me-PhO)-Ph |
| 3-F-Ph | 3,5-diCF$_3$-Ph | 7-OCF$_3$-2-nap | 2-F-Ph |
| 4-CF$_3$-Ph | 2-MeO-Ph | 4-PhO-2-pyridinyl | 4-Me-Ph |
| 3,4-diCl-Ph | 3-CF$_3$O-Ph | 4-EtO-2-pyrimidinyl | 4-MeO-2-pyrimidinyl |
| 3,4-diCF$_3$-Ph | 3-Et-Ph | 4-CF$_3$-2-pyridinyl | 5-Me-2-furanyl |
| 3-EtO-Ph | 3-Ph-Ph | 4-CF$_3$-2-pyrimidinyl | 4-Ph-Ph |
|  | 3,4-diMe-Ph | 6-CF$_3$-2-pyrazinyl | 2-I-Ph |
| 2-nap | 3,5-diMe-Ph | 5-CF$_3$-3-pyridinyl | 2,5-diMe-3-thienyl |
| 3-SF$_5$-Ph | 3-MeS-Ph | 4-t-Bu-2-nap | 3-MeO-6-pyridazinyl |
|  |  | 3,5-diBr-Ph | 5-PhO-2-pyrimidinyl |
| 4-F-3-CF$_3$-Ph | 4-Me$_3$Si-Ph | 4-t-Bu-2-pyridinyl | 6-PhO-2-pyridinyl |
| 5-F-3-CF$_3$-Ph | 3-Me$_3$Ge-Ph | 4-Ph-2-pyridinyl | (4-Br-Ph)CH$_2$ |
| i-Bu | 4-Me$_3$Ge-Ph | 4-Me$_3$Si-2-pyridinyl | n-Bu |

TABLE 4

Compounds of Formula I where E = 1,2-phenylene,
A = O, G = C, W = O, X = OMe, R$^2$ = Me,
the floating double bond is attached to G and

| Z | Z | Z | Z |
|---|---|---|---|
| Y = CH=C(Cl)C(=O)O | | | |
| 2-Br-Ph | i-Pr | PhC≡CCH$_2$ | 4-Me$_3$Ge-2-pyridinyl |
| 2-CN-Ph | c-pentyl | 2-Et-Ph | 4-CF$_3$-2-nap |
| 2-CF$_3$-Ph | PhCH$_2$ | 2-Cl-Ph | (c-Pr)CH$_2$ |
| c-hexyl | 1-phenylethyl | 2,4,6-triCl-Ph | 3-pentynyl |
| PhCH$_2$CH$_2$ | (4-Cl-Ph)CH$_2$ | 3-PhO-Ph | 4-octenyl |
| (2-CN-Ph)CH$_2$ | (3-F-Ph)CH$_2$ | 6-Ph-2-pyridinyl | hexyl |
| CF$_3$CH$_2$ | 2,5-diMe-Ph | 6-CF$_3$-2-pyridinyl | 4-(PhO)-c-hexyl |
| 2-MeS-Ph | HC≡CCH$_2$ | 4-Me-2-pyrimidinyl | 2-CF$_3$O-Ph |
| 4-Cl-Ph | H$_2$C=CHCH$_2$ | 6-MeO-4-pyrimidinyl | 3-(2-Et-PhO)-Ph |
| 3-Me-Ph | PhCH=CHCH$_2$ | 2-Ph-4-thiazolyl | 6-CF$_3$-4-pyrimidinyl |
|  | 2-Me-Ph | 3-OCF$_2$H-Ph | PhCH=CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-Me$_3$Si-2-nap | 3-(2-Me-PhO)-Ph |
| 3-F-Ph | 3,5-diCF$_3$-Ph | 7-OCF$_3$-2-nap | 2-F-Ph |
| 4-CF$_3$-Ph | 2-MeO-Ph | 4-PhO-2-pyridinyl | 4-Me-Ph |
| 3,4-diCl-Ph | 3-CF$_3$O-Ph | 4-EtO-2-pyrimidinyl | 4-MeO-2-pyrimidinyl |
| 3,4-diCF$_3$-Ph | 3-Et-Ph | 4-CF$_3$-2-pyridinyl | 5-Me-2-furanyl |
| 3-EtO-Ph | 3-Ph-Ph | 4-CF$_3$-2-pyrimidinyl | 4-Ph-Ph |
|  | 3,4-diMe-Ph | 6-CF$_3$-2-pyrazinyl | 2-I-Ph |
| 2-nap | 3,5-diMe-Ph | 5-CF$_3$-3-pyridinyl | 2,5-diMe-3-thienyl |
| 3-SF$_5$-Ph | 3-MeS-Ph | 4-t-Bu-2-nap | 3-MeO-6-pyridazinyl |
|  | 3,5-diBr-Ph |  | 5-PhO-2-pyrimidinyl |
| 4-F-3-CF$_3$-Ph | 4-Me$_3$Si-Ph | 4-t-Bu-2-pyridinyl | 6-PhO-2-pyridinyl |
| 5-F-3-CF$_3$-Ph | 3-Me$_3$Ge-Ph | 4-Ph-2-pyridinyl | (4-Br-Ph)CH$_2$ |
| i-Bu | 4-Me$_3$Ge-Ph | 4-Me$_3$Si-2-pyridinyl | n-Bu |
| Y = CH=N—N=C(Me) | | | |
| 2-Br-Ph | i-Pr | PhC≡CCH$_2$ | 4-Me$_3$Ge-2-pyridinyl |
| 2-CN-Ph | c-pentyl | 2-Et-Ph | 4-CF$_3$-2-nap |
| 2-CF$_3$-Ph | PhCH$_2$ | 2-Cl-Ph | (c-Pr)CH$_2$ |
| c-hexyl | 1-phenylethyl | 2,4,6-triCl-Ph | 3-pentynyl |
| PhCH$_2$CH$_2$ | (4-Cl-Ph)CH$_2$ | 3-PhO-Ph | 4-octenyl |
| (2-CN-Ph)CH$_2$ | (3-F-Ph)CH$_2$ | 6-Ph-2-pyridinyl | hexyl |
| CF$_3$CH$_2$ | 2,5-diMe-Ph | 6-CF$_3$-2-pyridinyl | 4-(PhO)-c-hexyl |
| 2-MeS-Ph | HC≡CCH$_2$ | 4-Me-2-pyrimidinyl | 2-CF$_3$O-Ph |
| 4-Cl-Ph | H$_2$C=CHCH$_2$ | 6-MeO-4-pyrimidinyl | 3-(2-Et-PhO)-Ph |
| 3-Me-Ph | PhCH=CHCH$_2$ | 2-Ph-4-thiazolyl | 6-CF$_3$-4-pyrimidinyl |
|  | 2-Me-Ph | 3-OCF$_2$H-Ph | PhCH=CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-Me$_3$Si-2-nap | 3-(2-Me-PhO)-Ph |
| 3-F-Ph | 3,5-diCF$_3$-Ph | 7-OCF$_3$-2-nap | 2-F-Ph |
| 4-CF$_3$-Ph | 2-MeO-Ph | 4-PhO-2-pyridinyl | 4-Me-Ph |
| 3,4-diCl-Ph | 3-CF$_3$O-Ph | 4-EtO-2-pyrimidinyl | 4-MeO-2-pyrimidinyl |
| 3,4-diCF$_3$-Ph | 3-Et-Ph | 4-CF$_3$-2-pyridinyl | 5-Me-2-furanyl |
| 3-EtO-Ph | 3-Ph-Ph | 4-CF$_3$-2-pyrimidinyl | 4-Ph-Ph |
|  | 3,4-diMe-Ph | 6-CF$_3$-2-pyrazinyl | 2-I-Ph |
| 2-nap | 3,5-diMe-Ph | 5-CF$_3$-3-pyridinyl | 2,5-diMe-3-thienyl |
| 3-SF$_5$-Ph | 3-MeS-Ph | 4-t-Bu-2-nap | 3-MeO-6-pyridazinyl |
|  | 3,5-diBr-Ph |  | 5-PhO-2-pyrimidinyl |
| 4-F-3-CF$_3$-Ph | 4-Me$_3$Si-Ph | 4-t-Bu-2-pyridinyl | 6-PhO-2-pyridinyl |
| 5-F-3-CF$_3$-Ph | 3-Me$_3$Ge-Ph | 4-Ph-2-pyridinyl | (4-Br-Ph)CH$_2$ |
| i-Bu | 4-Me$_3$Ge-Ph | 4-Me$_3$Si-2-pyridinyl | n-Bu |
| Y = CH$_2$SC(Et)=N | | | |
| 2-Br-Ph | i-Pr | PhC≡CCH$_2$ | 4-Me$_3$Ge-2-pyridinyl |
| 2-CN-Ph | c-pentyl | 2-Et-Ph | 4-CF$_3$-2-nap |
| 2-CF$_3$-Ph | PhCH$_2$ | 2-Cl-Ph | (c-Pr)CH$_2$ |
| c-hexyl | 1-phenylethyl | 2,4,6-triCl-Ph | 3-pentynyl |
| PhCH$_2$CH$_2$ | (4-Cl-Ph)CH$_2$ | 3-PhO-Ph | 4-octenyl |
| (2-CN-Ph)CH$_2$ | (3-F-Ph)CH$_2$ | 6-Ph-2-pyridinyl | hexyl |
| CF$_3$CH$_2$ | 2,5-diMe-Ph | 6-CF$_3$-2-pyridinyl | 4-(PhO)-c-hexyl |
| 2-MeS-Ph | HC≡CCH$_2$ | 4-Me-2-pyrimidinyl | 2-CF$_3$O-Ph |
| 4-Cl-Ph | H$_2$C=CHCH$_2$ | 6-MeO-4-pyrimidinyl | 3-(2-Et-PhO)-Ph |
| 3-Me-Ph | PhCH=CHCH$_2$ | 2-Ph-4-thiazolyl | 6-CF$_3$-4-pyrimidinyl |
|  | 2-Me-Ph | 3-OCF$_2$H-Ph | PhCH=CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-Me$_3$Si-2-nap | 3-(2-Me-PhO)-Ph |
| 3-F-Ph | 3,5-diCF$_3$-Ph | 7-OCF$_3$-2-nap | 2-F-Ph |
| 4-CF$_3$-Ph | 2-MeO-Ph | 4-PhO-2-pyridinyl | 4-Me-Ph |
| 3,4-diCl-Ph | 3-CF$_3$O-Ph | 4-EtO-2-pyrimidinyl | 4-MeO-2-pyrimidinyl |
| 3,4-diCF$_3$-Ph | 3-Et-Ph | 4-CF$_3$-2-pyridinyl | 5-Me-2-furanyl |

TABLE 4-continued

Compounds of Formula I where E = 1,2-phenylene,
A = O, G = C, W = O, X = OMe, $R^2$ = Me,
the floating double bond is attached to G and

| Z | Z | Z | Z |
|---|---|---|---|
| 3-EtO-Ph | 3-Ph-Ph | 4-$CF_3$-2-pyrimidinyl | 4-Ph-Ph |
|  | 3,4-diMe-Ph | 6-$CF_3$-2-pyrazinyl | 2-I-Ph |
| 2-nap | 3,5-diMe-Ph | 5-$CF_3$-3-pyridinyl | 2,5-diMe-3-thienyl |
| 3-$SF_5$-Ph | 3-MeS-Ph | 4-t-Bu-2-nap | 3-MeO-6-pyridazinyl |
|  |  | 3,5-diBr-Ph | 5-PhO-2-pyrimidinyl |
| 4-F-3-$CF_3$-Ph | 4-$Me_3$Si-Ph | 4-t-Bu-2-pyridinyl | 6-PhO-2-pyridinyl |
| 5-F-3-$CF_3$-Ph | 3-$Me_3$Ge-Ph | 4-Ph-2-pyridinyl | (4-Br-Ph)$CH_2$ |
| i-Bu | 4-$Me_3$Ge-Ph | 4-$Me_3$Si-2-pyridinyl | n-Bu |

Y = $CH_2O-N=C(SMe)$

| Z | Z | Z | Z |
|---|---|---|---|
| 2-Br-Ph | i-Pr | PhC≡$CCH_2$ | 4-$Me_3$Ge-2-pyridinyl |
| 2-CN-Ph | c-pentyl | 2-Et-Ph |  |
| 2-$CF_3$-Ph | Ph$CH_2$ | 2-Cl-Ph | (c-Pr)$CH_2$ |
| c-hexyl | 1-phenylethyl | 2,4,6-triCl-Ph | 3-pentynyl |
| Ph$CH_2CH_2$ | (4-Cl-Ph)$CH_2$ | 3-PhO-Ph | 4-octenyl |
| (2-CN-Ph)$CH_2$ | (3-F-Ph)$CH_2$ | 6-Ph-2-pyridinyl | hexyl |
| $CF_3CH_2$ | 2,5-diMe-Ph | 6-$CF_3$-2-pyridinyl | 4-(PhO)-c-hexyl |
| 2-MeS-Ph | HC≡$CCH_2$ | 4-Me-2-pyrimidinyl | 2-$CF_3$O-Ph |
| 4-Cl-Ph | $H_2$C=CH$CH_2$ | 6-MeO-4-pyrimidinyl | 3-(2-Et-PhO)-Ph |
| 3-Me-Ph | PhCH=CH$CH_2$ | 2-Ph-4-thiazolyl | 6-$CF_3$-4-pyrimidinyl |
|  | 2-Me-Ph | 3-$OCF_2$H-Ph | PhCH=CHCH(Me) |
| 3-Cl-2-Me-Ph | 2-Me-4-Cl-Ph |  | 4,6-diMe-O-2-pyrimidinyl |
| 3-t-Bu-Ph |  |  | 3-(2-Me-PhO)-Ph |
| 3-F-Ph | 3,5-di$CF_3$-Ph |  | 2-F-Ph |
| 4-$CF_3$-Ph | 2-MeO-Ph | 4-PhO-2-pyridinyl | 4-Me-Ph |
| 3,4-diCl-Ph | 3-$CF_3$O-Ph | 4-EtO-2-pyrimidinyl | 4-MeO-2-pyrimidinyl |
| 3,4-di$CF_3$-Ph | 3-Et-Ph | 4-$CF_3$-2-pyridinyl | 5-Me-2-furanyl |
| 3-EtO-Ph | 3-Ph-Ph | 4-$CF_3$-2-pyrimidinyl | 4-Ph-Ph |
|  | 3,4-diMe-Ph | 6-$CF_3$-2-pyrazinyl | 2-I-Ph |
|  | 3,5-diMe-Ph | 5-$CF_3$-3-pyridinyl | 2,5-diMe-3-thienyl |
| 3-$SF_5$-Ph | 3-MeS-Ph |  | 3-MeO-6-pyridazinyl |
|  |  | 3,5-diBr-Ph | 5-PhO-2-pyrimidinyl |
| 4-F-3-$CF_3$-Ph | 4-$Me_3$Si-Ph | 4-t-Bu-2-pyridinyl | 6-PhO-2-pyridinyl |
| 5-F-3-$CF_3$-Ph | 3-$Me_3$Ge-Ph | 4-Ph-2-pyridinyl | (4-Br-Ph)$CH_2$ |
| i-Bu | 4-$Me_3$Ge-Ph | 4-$Me_3$Si-2-pyridinyl | n-Bu |

Y = $CH_2O-N=C(Me)CH_2S$

| Z | Z | Z | Z |
|---|---|---|---|
| 2-Br-Ph | i-Pr | PhC≡$CCH_2$ | 4-$Me_3$Ge-2-pyridinyl |
| 2-CN-Ph | c-pentyl | 2-Et-Ph | 4-$CF_3$-2-nap |
| 2-$CF_3$-Ph | Ph$CH_2$ | 2-Cl-Ph | (c-Pr)$CH_2$ |
| c-hexyl | 1-phenylethyl | 2,4,6-triCl-Ph | 3-pentynyl |
| Ph$CH_2CH_2$ | (4-Cl-Ph)$CH_2$ | 3-PhO-Ph | 4-octenyl |
| (2-CN-Ph)$CH_2$ | (3-F-Ph)$CH_2$ | 6-Ph-2-pyridinyl | hexyl |
| $CF_3CH_2$ | 2,5-diMe-Ph | 6-$CF_3$-2-pyridinyl | 4-(PhO)-c-hexyl |
| 2-MeS-Ph | HC≡$CCH_2$ | 4-Me-2-pyrimidinyl | 2-$CF_3$O-Ph |
| 4-Cl-Ph | $H_2$C=CH$CH_2$ | 6-MeO-4-pyrimidinyl | 3-(2-Et-PhO)-Ph |
| 3-Me-Ph | PhCH=CH$CH_2$ | 2-Ph-4-thiazolyl | 6-$CF_3$-4-pyrimidinyl |
|  | 2-Me-Ph | 3-$OCF_2$H-Ph | PhCH=CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-$Me_3$Si-2-nap | 3-(2-Me-PhO)-Ph |
| 3-F-Ph |  | 7-$OCF_3$-2-nap | 2-F-Ph |
| 4-$CF_3$-Ph | 2-MeO-Ph | 4-PhO-2-pyridinyl | 4-Me-Ph |
| 3,4-diCl-Ph | 3-$CF_3$O-Ph | 4-EtO-2-pyrimidinyl | 4-MeO-2-pyrimidinyl |
| 3,4-di$CF_3$-Ph | 3-Et-Ph | 4-$CF_3$-2-pyridinyl | 5-Me-2-furanyl |
| 3-EtO-Ph | 3-Ph-Ph | 4-$CF_3$-2-pyrimidinyl | 4-Ph-Ph |
|  | 3,4-diMe-Ph | 6-$CF_3$-2-pyrazinyl | 2-I-Ph |
| 2-nap | 3,5-diMe-Ph | 5-$CF_3$-3-pyridinyl | 2,5-diMe-3-thienyl |
| 3-$SF_5$-Ph | 3-MeS-Ph | 4-t-Bu-2-nap | 3-MeO-6-pyridazinyl |
|  |  | 3,5-diBr-Ph | 5-PhO-2-pyrimidinyl |
| 4-F-3-$CF_3$-Ph | 4-$Me_3$Si-Ph | 4-t-Bu-2-pyridinyl | 6-PhO-2-pyridinyl |
| 5-F-3-$CF_3$-Ph | 3-$Me_3$Ge-Ph | 4-Ph-2-pyridinyl | (4-Br-Ph)$CH_2$ |
| i-Bu | 4-$Me_3$Ge-Ph | 4-$Me_3$Si-2-pyridinyl | n-Bu |

Y = $CH_2O-N=C(Me)CH_2O$

| Z | Z | Z | Z |
|---|---|---|---|
| 2-Br-Ph | i-Pr | PhC≡$CCH_2$ | 4-$Me_3$Ge-2-pyridinyl |
| 2-CN-Ph | c-pentyl | 2-Et-Ph | 4-$CF_3$-2-nap |
| 2-$CF_3$-Ph | Ph$CH_2$ | 2-Cl-Ph | (c-Pr)$CH_2$ |
| c-hexyl | 1-phenylethyl | 2,4,6-triCl-Ph | 3-pentynyl |
| Ph$CH_2CH_2$ | (4-Cl-Ph)$CH_2$ | 3-PhO-Ph | 4-octenyl |
| (2-CN-Ph)$CH_2$ | (3-F-Ph)$CH_2$ | 6-Ph-2-pyridinyl | hexyl |
| $CF_3CH_2$ | 2,5-diMe-Ph | 6-$CF_3$-2-pyridinyl | 4-(PhO)-c-hexyl |
| 2-MeS-Ph | HC≡$CCH_2$ | 4-Me-2-pyrimidinyl | 2-$CF_3$O-Ph |
| 4-Cl-Ph | $H_2$C=CH$CH_2$ | 6-MeO-4-pyrimidinyl | 3-(2-Et-PhO)-Ph |

TABLE 4-continued

Compounds of Formula I where E = 1,2-phenylene,
A = O, G = C, W = O, X = OMe, R² = Me,
the floating double bond is attached to G and

| Z | Z | Z | Z |
|---|---|---|---|
| 3-Me-Ph | PhCH=CHCH₂ | 2-Ph-4-thiazolyl | 6-CF₃-4-pyrimidinyl |
|  | 2-Me-Ph | 3-OCF₂H-Ph | PhCH=CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-Me₃Si-2-nap | 3-(2-Me-PhO)-Ph |
| 3-F-Ph | 3,5-diCF₃-Ph | 7-OCF₃-2-nap | 2-F-Ph |
| 4-CF₃-Ph | 2-MeO-Ph | 4-PhO-2-pyridinyl | 4-Me-Ph |
| 3,4-diCl-Ph | 3-CF₃O-Ph | 4-EtO-2-pyrimidinyl | 4-MeO-2-pyrimidinyl |
| 3,4-diCF₃-Ph | 3-Et-Ph | 4-CF₃-2-pyridinyl | 5-Me-2-furanyl |
| 3-EtO-Ph | 3-Ph-Ph | 4-CF₃-2-pyrimidinyl | 4-Ph-Ph |
|  | 3,4-diMe-Ph | 6-CF₃-2-pyrazinyl | 2-I-Ph |
| 2-nap | 3,5-diMe-Ph | 5-CF₃-3-pyridinyl | 2,5-diMe-3-thienyl |
| 3-SF₅-Ph | 3-MeS-Ph | 4-t-Bu-2-nap | 3-MeO-6-pyridazinyl |
|  |  | 3,5-diBr-Ph | 5-PhO-2-pyrimidinyl |
| 4-F-3-CF₃-Ph | 4-Me₃Si-Ph | 4-t-Bu-2-pyridinyl | 6-PhO-2-pyridinyl |
| 5-F-3-CF₃-Ph | 3-Me₃Ge-Ph | 4-Ph-2-pyridinyl | (4-Br-Ph)CH₂ |
| i-Bu | 4-Me₃Ge-Ph | 4-Me₃Si-2-pyridinyl | n-Bu |

Y = CH=N—N(Me)

| | | | |
|---|---|---|---|
| 2-Br-Ph | i-Pr | PhC≡CCH₂ | 4-Me₃Ge-2-pyridinyl |
| 2-CN-Ph | c-pentyl | 2-Et-Ph | 4-CF₃-2-nap |
| 2-CF₃-Ph | PhCH₂ | 2-Cl-Ph | (c-Pr)CH₂ |
| c-hexyl | 1-phenylethyl | 2,4,6-triCl-Ph | 3-pentynyl |
| PhCH₂CH₂ | (4-Cl-Ph)CH₂ | 3-PhO-Ph | 4-octenyl |
| (2-CN-Ph)CH₂ | (3-F-Ph)CH₂ | 6-Ph-2-pyridinyl | hexyl |
| CF₃CH₂ | 2,5-diMe-Ph | 6-CF₃-2-pyridinyl | 4-(PhO)-c-hexyl |
| 2-MeS-Ph | HC≡CCH₂ | 4-Me-2-pyrimidinyl | 2-CF₃O-Ph |
| 4-Cl-Ph | H₂C=CHCH₂ | 6-MeO-4-pyrimidinyl | 3-(2-Et-PhO)-Ph |
| 3-Me-Ph | PhCH=CHCH₂ | 2-Ph-4-thiazolyl | 6-CF₃-4-pyrimidinyl |
|  | 2-Me-Ph | 3-OCF₂H-Ph | PhCH=CHCH(Me) |
| 3-Cl-2-Me-Ph | 2-Me-4-Cl-Ph | 5-Me-2-nap | 4,6-diMe-O-2-pyrimidinyl |
| 3-t-Bu-Ph |  | 6-Me₃Si-2-nap | 3-(2-Me-PhO)-Ph |
| 3-F-Ph | 3,5-diCF₃-Ph | 7-OCF₃-2-nap | 2-F-Ph |
| 4-CF₃-Ph | 2-MeO-Ph | 4-PhO-2-pyridinyl | 4-Me-Ph |
| 3,4-diCl-Ph | 3-CF₃O-Ph | 4-EtO-2-pyrimidinyl | 4-MeO-2-pyrimidinyl |
| 3,4-diCF₃-Ph | 3-Et-Ph | 4-CF₃-2-pyridinyl | 5-Me-2-furanyl |
| 3-EtO-Ph | 3-Ph-Ph | 4-CF₃-2-pyrimidinyl | 4-Ph-Ph |
|  | 3,4-diMe-Ph | 6-CF₃-2-pyrazinyl | 2-I-Ph |
| 2-nap | 3,5-diMe-Ph | 5-CF₃-3-pyridinyl | 2,5-diMe-3-thienyl |
| 3-SF₅-Ph | 3-MeS-Ph | 4-t-Bu-2-nap | 3-MeO-6-pyridazinyl |
|  |  | 3,5-diBr-Ph | 5-PhO-2-pyrimidinyl |
| 4-F-3-CF₃-Ph | 4-Me₃Si-Ph | 4-t-Bu-2-pyridinyl | 6-PhO-2-pyridinyl |
| 5-F-3-CF₃-Ph | 3-Me₃Ge-Ph | 4-Ph-2-pyridinyl | (4-Br-Ph)CH₂ |
| i-Bu | 4-Me₃Ge-Ph | 4-Me₃Si-2-pyridinyl | n-Bu |

TABLE 5

Compounds of Formula I where E = 1,2-phenylene, Z = t-Bu,
Y = CH=C(Cl)C(=O)O, G = N, the floating double bond is attached to A and

| X | A | X | A | X | A | X | A |
|---|---|---|---|---|---|---|---|
| R² = Me, W = O | | | | | | | |
|  |  | MeS | N | MeO | CH | MeS | CH |
| EtO | N | EtS | N | EtO | CH | EtS | CH |
| n-PrO | N | n-PrS | N | n-PrO | CH | n-PrS | CH |
| H₂C=CHCH₂O | N | H₂C=CHCH₂S | N | H₂C=CHCH₂O | CH | H₂C=CHCH₂S | CH |
| HC≡CCH₂O | N | HC≡CCH₂S | N | HC≡CCH₂O | CH | HC≡CCH₂S | CH |
| CF₃O | N | CF₃S | N | CF₃O | CH | CF₃S | CH |
| (c-Pr)O | N | (c-Pr)S | N | (c-Pr)O | CH | (c-Pr)S | CH |
| R² = Et, W = O | | | | | | | |
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H₂C=CHCH₂O | N | H₂C=CHCH₂S | N | H₂C=CHCH₂O | CH | H₂C=CHCH₂S | CH |
| HC≡CCH₂O | N | HC≡CCH₂S | N | HC≡CCH₂O | CH | HC≡CCH₂S | CH |
| CF₃O | N | CF₃S | N | CF₃O | CH | CF₃S | CH |
| (c-Pr)O | N | (c-Pr)S | N | (c-Pr)O | CH | (c-Pr)S | CH |

TABLE 5-continued

Compounds of Formula I where E = 1,2-phenylene, Z = t-Bu,
Y = CH=C(Cl)C(=O)O, G = N, the floating double bond is attached to A and

| X | A | X | A | X | A | X | A |
|---|---|---|---|---|---|---|---|
| $R^2$ = Me, W = S ||||||||
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| $H_2C$=CHCH$_2$O | N | $H_2C$=CHCH$_2$S | N | $H_2C$=CHCH$_2$O | CH | $H_2C$=CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |
| $R^2$ = Et, W = S ||||||||
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| $H_2C$=CHCH$_2$O | N | $H_2C$=CHCH$_2$S | N | $H_2C$=CHCH$_2$O | CH | $H_2C$=CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |

TABLE 6

Compounds of Formula I where E = 1,2-phenylene, Z = t-Bu,
Y = CH=C(Cl)C(=O)O, G = C, the floating double bond is attached to G and

| X | A | X | A | X | A | X | A |
|---|---|---|---|---|---|---|---|
| $R^2$ = Me, W = O ||||||||
|  |  | MeS | O | MeO | S | MeS | S |
| EtO | O | EtS | O | EtO | S | EtS | S |
| n-PrO | O | n-PrS | O | n-PrO | S | n-PrS | S |
| $H_2C$=CHCH$_2$O | O | $H_2C$=CHCH$_2$S | O | $H_2C$=CHCH$_2$O | S | $H_2C$=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| $R^2$ = Et, W = O ||||||||
| MeO | O | MeS | O | MeO | S | MeS | S |
| EtO | O | EtS | O | EtO | S | EtS | S |
| n-PrO | O | n-PrS | O | n-PrO | S | n-PrS | S |
| $H_2C$=CHCH$_2$O | O | $H_2C$=CHCH$_2$S | O | $H_2C$=CHCH$_2$O | S | $H_2C$=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| $R^2$ = Me, W = S ||||||||
| MeO | O | MeS | O | MeO | S | MeS | S |
| EtO | O | EtS | O | EtO | S | EtS | S |
| n-PrO | O | n-PrS | O | n-PrO | S | n-PrS | S |
| $H_2C$=CHCH$_2$O | O | $H_2C$=CHCH$_2$S | O | $H_2C$=CHCH$_2$O | S | $H_2C$=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| $R^2$ = Et, W = S ||||||||
| MeO | O | MeS | O | MeO | S | MeS | S |
| EtO | O | EtS | O | EtO | S | EtS | S |
| n-PrO | O | n-PrS | O | n-PrO | S | n-PrS | S |
| $H_2C$=CHCH$_2$O | O | $H_2C$=CHCH$_2$S | O | $H_2C$=CHCH$_2$O | S | $H_2C$=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |

TABLE 7

Compounds of Formula I where E = 1,2-phenylene, Z = 3-CF$_3$-Ph, Y = CH$_2$O—N═C(SMe), G = N, the floating double bond is attached to A and

| X | A | X | A | X | A | X | A |
|---|---|---|---|---|---|---|---|
| | | | | R$^2$ = Me, W = O | | | |
| | | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C═CHCH$_2$O | N | H$_2$C═CHCH$_2$S | N | H$_2$C═CHCH$_2$O | CH | H$_2$C═CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |
| | | | | R$^2$ = Et, W = O | | | |
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C═CHCH$_2$O | N | H$_2$C═CHCH$_2$S | N | H$_2$C═CHCH$_2$O | CH | H$_2$C═CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |
| | | | | R$^2$ = Me, W = S | | | |
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C═CHCH$_2$O | N | H$_2$C═CHCH$_2$S | N | H$_2$C═CHCH$_2$O | CH | H$_2$C═CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |
| | | | | R$^2$ = Et, W = S | | | |
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C═CHCH$_2$O | N | H$_2$C═CHCH$_2$S | N | H$_2$C═CHCH$_2$O | CH | H$_2$C═CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |

TABLE 8

Compounds of Formula I where E = 1,2-phenylene, Z = 3-CF$_3$-Ph, Y = CH$_2$O—N═C(SMe), G = C, the floating double bond is attached to G and

| X | A | X | A | X | A | X | A |
|---|---|---|---|---|---|---|---|
| | | | | R$^2$ = Me, W = O | | | |
| | | MeS | O | MeO | S | MeS | S |
| EtO | O | EtS | O | EtO | S | EtS | S |
| n-PrO | O | n-PrS | O | n-PrO | S | n-PrS | S |
| H$_2$C═CHCH$_2$O | O | H$_2$C═CHCH$_2$S | O | H$_2$C═CHCH$_2$O | S | H$_2$C═CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| | | | | R$^2$ = Et, W = O | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C═CHCH$_2$O | O | H$_2$C═CHCH$_2$S | O | H$_2$C═CHCH$_2$O | S | H$_2$C═CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| | | | | R$^2$ = Me, W = S | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C═CHCH$_2$O | O | H$_2$C═CHCH$_2$S | O | H$_2$C═CHCH$_2$O | S | H$_2$C═CHCH$_2$S | S |

TABLE 8-continued

Compounds of Formula I where E = 1,2-phenylene, Z = 3-CF$_3$-Ph,
Y = CH$_2$O—N═C(SMe), G = C, the floating double bond is attached to G and

| X | A | X | A | X | A | X | A |
|---|---|---|---|---|---|---|---|
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |

$R^2$ = Et, W = S

| X | A | X | A | X | A | X | A |
|---|---|---|---|---|---|---|---|
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C═CHCH$_2$O | O | H$_2$C═CHCH$_2$S | O | H$_2$C═CHCH$_2$O | S | H$_2$C═CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |

TABLE 9

Compounds of Formula I where E = 1,2-phenylene, Z = 3-CF$_3$-Ph,
Y = CH$_2$SC(Et)═N, G = N, the floating double bond is attached to A and $R^2$ = Me, W = O

| X | A | X | A | X | A | X | A |
|---|---|---|---|---|---|---|---|
|  |  | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C═CHCH$_2$O | N | H$_2$C═CHCH$_2$S | N | H$_2$C═CHCH$_2$O | CH | H$_2$C═CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |

$R^2$ = Et, W = O

| X | A | X | A | X | A | X | A |
|---|---|---|---|---|---|---|---|
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C═CHCH$_2$O | N | H$_2$C═CHCH$_2$S | N | H$_2$C═CHCH$_2$O | CH | H$_2$C═CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |

$R^2$ = Me, W = S

| X | A | X | A | X | A | X | A |
|---|---|---|---|---|---|---|---|
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C═CHCH$_2$O | N | H$_2$C═CHCH$_2$S | N | H$_2$C═CHCH$_2$O | CH | H$_2$C═CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |

$R^2$ = Et, W = S

| X | A | X | A | X | A | X | A |
|---|---|---|---|---|---|---|---|
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C═CHCH$_2$O | N | H$_2$C═CHCH$_2$S | N | H$_2$C═CHCH$_2$O | CH | H$_2$C═CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |

TABLE 10

Compounds of Formula I where E = 1,2-phenylene, Z = 3-CF$_3$-Ph,
Y = CH$_2$SC(Et) = N, G = C, the floating double bond is attached to G and

| X | A | X | A | X | A | X | A |
|---|---|---|---|---|---|---|---|
| \multicolumn{8}{c}{R$^2$ = Me, W = O} ||||||||
|  |  | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| \multicolumn{8}{c}{R$^2$ = Et, W = O} ||||||||
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| \multicolumn{8}{c}{R$^2$ = Me, W = S} ||||||||
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| \multicolumn{8}{c}{R$^2$ = Et, W = S} ||||||||
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |

TABLE 11

Compounds of Formula I where E = 1,2-phenylene, Z = 3,5-diCF$_3$-Ph,
Y = CH$_2$O—N=C(NH$_2$), G = N, the floating double bond is attached to A and

| X | A | X | A | X | A | X | A |
|---|---|---|---|---|---|---|---|
| \multicolumn{8}{c}{R$^2$ = Me, W = O} ||||||||
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C=CHCH$_2$O | N | H$_2$C=CHCH$_2$S | N | H$_2$C=CHCH$_2$O | CH | H$_2$C=CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |
| \multicolumn{8}{c}{R$^2$ = Et, W = O} ||||||||
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C=CHCH$_2$O | N | H$_2$C=CHCH$_2$S | N | H$_2$C=CHCH$_2$O | CH | H$_2$C=CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |
| \multicolumn{8}{c}{R$^2$ = Me, W = S} ||||||||
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C=CHCH$_2$O | N | H$_2$C=CHCH$_2$S | N | H$_2$C=CHCH$_2$O | CH | H$_2$C=CHCH$_2$S | CH |

TABLE 11-continued

Compounds of Formula I where E = 1,2-phenylene, Z = 3,5-diCF$_3$-Ph,
Y = CH$_2$O—N=C(NH$_2$), G = N, the floating double bond is attached to A and

| X | A | X | A | X | A | X | A |
|---|---|---|---|---|---|---|---|
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |

R$^2$ = Et, W = S

| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C=CHCH$_2$O | N | H$_2$C=CHCH$_2$S | N | H$_2$C=CHCH$_2$O | CH | H$_2$C=CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |

TABLE 12

Compounds of Formula I where E = 1,2-phenylene, Z = 3,5-diCF$_3$-Ph,
Y = CH$_2$O—N=C(NH$_2$), G = C, the floating double bond is attached to G and

| X | A | X | A | X | A | X | A |
|---|---|---|---|---|---|---|---|

R$^2$ = Me, W = O

| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |

R$^2$ = Et, W = O

| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |

R$^2$ = Me, W = S

| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |

R$^2$ = Et, W = S

| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |

TABLE 13

Compounds of Formula I where E = 1,2-phenylene, Z = 3,5-diCl-Ph,
Y = CH$_2$O—N=C(Me)CH$_2$S, G = N, the floating double bond is attached to A and

| X | A | X | A | X | A | X | A |
|---|---|---|---|---|---|---|---|
| $R^2$ = Me, W = O | | | | | | | |
|  |  | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C=CHCH$_2$O | N | H$_2$C=CHCH$_2$S | N | H$_2$C=CHCH$_2$O | CH | H$_2$C=CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |
| $R^2$ = Et, W = O | | | | | | | |
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C=CHCH$_2$O | N | H$_2$C=CHCH$_2$S | N | H$_2$C=CHCH$_2$O | CH | H$_2$C=CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |
| $R^2$ = Me, W = S | | | | | | | |
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C=CHCH$_2$O | N | H$_2$C=CHCH$_2$S | N | H$_2$C=CHCH$_2$O | CH | H$_2$C=CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |
| $R^2$ = Et, W = S | | | | | | | |
| MeO | N | MeS | N | MeO | CH | MeS | CH |
| EtO | N | EtS | N | EtO | CH | EtS | CH |
| n-PrO | N | n-PrS | N | n-PrO | CH | n-PrS | CH |
| H$_2$C=CHCH$_2$O | N | H$_2$C=CHCH$_2$S | N | H$_2$C=CHCH$_2$O | CH | H$_2$C=CHCH$_2$S | CH |
| HC≡CCH$_2$O | N | HC≡CCH$_2$S | N | HC≡CCH$_2$O | CH | HC≡CCH$_2$S | CH |
| CF$_3$O | N | CF$_3$S | N | CF$_3$O | CH | CF$_3$S | CH |
| (c-Pr)O | N | (c-Pr)S | N | (c-Pr)O | CH | (c-Pr)S | CH |

TABLE 14

Compounds of Formula I where E = 1,2-phenylene, Z = 3,5-diCl-Ph,
Y = CH$_2$O—N=C(Me)CH$_2$S, G = C, the floating double bond is attached to G and

| X | A | X | A | X | A | X | A |
|---|---|---|---|---|---|---|---|
| $R^2$ = Me, W = O | | | | | | | |
|  |  |  |  | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| $R^2$ = Et, W = O | | | | | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| $R^2$ = Me, W = S | | | | | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |

TABLE 14-continued

Compounds of Formula I where E = 1,2-phenylene, Z = 3,5-diCl-Ph,
Y = CH$_2$O—N=C(Me)CH$_2$S, G = C, the floating double bond is attached to G and

| X | A | X | A | X | A | X | A |
|---|---|---|---|---|---|---|---|
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |
| | | | | R$^2$ = Et, W = S | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-Pr)O | O | (c-Pr)S | O | (c-Pr)O | S | (c-Pr)S | S |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A—B.

Example A

Wettable Powder

| | |
|---|---|
| Compound 19 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

Granule

| | |
|---|---|
| Compound 19 | 10.0% |
| attapulgite granules (low volatile matter, 0.71/0.30 mm; U.S.S. No. 25–50 sieves) | 90.0%. |

Example C

Extruded Pellet

| | |
|---|---|
| Compound 19 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

Emulsifiable Concentrate

| | |
|---|---|
| Compound 19 | 20.0% |
| blend of oil soluble sulfonates and polyoxyethylene ethers | 10.0% |
| isophorone | 70.0%. |

The compounds of this invention are useful as plant disease control agents. The present invention therefore further comprises a method for controlling plant diseases caused by fungal plant pathogens comprising applying to the plant or portion thereof to be protected, or to the plant seed or seedling to be protected, an effective amount of a compound of the invention or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubensis, Pythium aphanidermatum, Alternaria brassicae, Septoria nodorum, Septoria tritici, Cercosporidium personatum, Cercospora arachidicola, Pseudocercosporella herpotrichoides, Cercospora beticola, Botrytis cinerea, Moniliniafructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striformis, Puccinia arachidis, Rhizoctonia solani, Sphaerotheca fuliginea, Fusarium oxysporum, Verticillium dahliae, Pythium aphanidennatum, Phytophthora megasperma, Sclerotinia sclerotiorum, Sclerotium rolfsii, Erysiphe polygoni, Pyrenophora teres, Gaeumannomyces graminis, Rynchosporium secalis, Fusarium roseum, Bremia lactucae* and other generea and species closely related to these pathogens.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorpyrifos, chlorpyrifos-methyl, cyfluthrin, beta-cyfluthrin, deltamethrin, diafenthiuron, diazinon, diflubenzuron, dimethoate, esfenvalerate, fenpropathrin, fenvalerate, fipronil, flucythrrinate, tau-fluvalinate, fonophos, imidacloprid, isofenphos, malathion, metaldehyde, methamidophos, methidathion, methomyl, methoprene, methoxychlor, monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as azoxystrobin (ICIA5504), benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxyconazole (BAS 480F), fenarimol, fenbuconazole, fenpiclonil, fenpropidin, fenpropimorph, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl (BAS 490F), mancozeb, maneb, mepronil, metalaxyl, metconazole, myclobutanil, neo-asozin (ferric methanearsonate), oxadixyl, penconazole, pencycuron, probenazole, prochloraz, propiconazole, pyrifenox, pyroquilon, sulfur, tebuconazole, tetraconazole, thiabendazole, thiophanate-methyl, thiram, triadimefon, triadimenol, tricyclazole, triticonazole, uniconazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

In certain instances, combinations with other fungicides having a similar spectrum of control but a different mode of action will be particularly advantageous for resistance management.

Preferred for better control of plant diseases caused by fungal plant pathogens (e.g., lower use rate or broader spectrum of plant pathogens controlled) or resistance management are mixtures of a compound of this invention with a fungicide selected from the group cyproconazole, cyprodinil (CGA 219417), epoxyconazole (BAS 480F), fenpropidin, fenpropimorph, flusilazole and tebuconazole. Specifically preferred mixtures (compound numbers refer to compounds in Index Tables A—B) are selected from the group: compound 2 and cyproconazole; compound 2 and cyprodinil (CGA 219417); compound 2 and epoxyconazole (BAS 480F); compound 2 and fenpropidin; compound 2 and fenpropimorph; compound 2 and flusilazole; compound 2 and tebuconazole; compound 3 and cyproconazole; compound 3 and cyprodinil (CGA 219417); compound 3 and epoxyconazole (BAS 480F); compound 3 and fenpropidin;

compound 3 and fenpropimorph; compound 3 and flusilazole; compound 3 and tebuconazole; compound 5 and cyproconazole; compound 5 and cyprodinil (CGA 219417); compound 5 and epoxyconazole (BAS 480F); compound 5 and fenpropidin; compound 5 and fenpropimorph; compound 5 and flusilazole; compound 5 and tebuconazole; compound 19 and cyproconazole; compound 19 and cyprodinil (CGA 219417); compound 19 and epoxyconazole (BAS 480F); compound 19 and fenpropidin; compound 19 and fenpropimorph; compound 19 and flusilazole; and compound 19 and tebuconazole.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Tables A—B for compound descriptions. The following abbreviation is used in the Index Tables which follow: Ph=phenyl. The abbreviation "Ex." stands for "Example" and is followed by a number indicating in which example the compound is prepared.

INDEX TABLE A

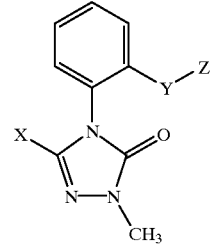

| Cmpd. No. | X | Y | Z | m.p. (° C.) |
|---|---|---|---|---|
| 1 | CH$_3$O | —C(=O)— | Ph | 126–134 |
| 2 (Ex. 2) | CH$_3$O | —CH=C(Cl)—C(=O)—O— | C(CH$_3$)3 | semisolid* |
| 3 (Ex. 1) | CH$_3$O | —CH$_2$S—C(CH$_2$CH$_3$)=N— | 4-Cl—Ph | gum* |
| 4 (Ex. 3) | CH$_3$O | —CH$_2$O—N=C(CN)—C(=O)— | 3-CF$_3$—Ph | gum* |
| 5 (Ex. 4) | CH$_3$O | —CH$_2$O—N=C(SCH$_3$)— | 3,4-diCl—Ph | solid* |
| 6 | CH$_3$O | —CH$_2$O—N=C(SO2CH$_3$)— | 3,4-diCl—Ph | semisolid* |
| 7 | CH$_3$O | —CH$_2$S—C(CH$_3$)=N— | 3-CF$_3$—Ph | oil* |
| 8 | CH$_3$O | —CH$_2$O—N=C(CH$_3$)—CH$_2$O— | 3-CF$_3$—Ph | oil* |
| 9 | CH$_3$O | —CH$_2$O—N=C(CH$_3$)—CH$_2$S— | 1-CH$_3$-1H-tetrazol-5-yl | oil* |
| 10 | CH$_3$O | —CH$_2$O—N=C(CH$_3$)—CH$_2$S— | 2-benzoxazolyl | oil* |
| 11 | CH$_3$O | —CH$_2$O—N=C(5CH$_3$)— | 3,5-diCl—Ph | oil* |
| 12 (Ex. 5) | CH$_3$O | —CH$_2$O—N=C(CH$_3$)—CH$_2$O— | 3,5-diCl—Ph | oil1* |
| 13 | CH$_3$O | —CH$_2$S—C(CH$_2$CH$_3$)=N— | 3-CF$_3$—Ph | oil* |
| 14 | CH$_3$O | —CH$_2$O—N=C(CH$_3$)—CH$_2$S— | 3,5-diCF$_3$—Ph | oil* |
| 15 | CH$_3$O | —CH$_2$O—N=C(CH$_3$)—CH$_2$O— | 3,5-diCF$_3$—Ph | oil* |
| 16 | CH$_3$O | —CH$_2$O—N=C(SCH$_3$)— | 3-CF$_3$—Ph | oil* |
| 17 | CH$_3$O | —CH$_2$O—N=C(CH$_3$)—CH$_2$S— | 2-benzothiazolyl | oil* |
| 18 | CH$_3$O | —CH$_2$O—N=C(CH$_3$)—CH$_2$S— | 3,5-diCl—Ph | oil* |
| 19 | CH$_3$O | —CH$_2$O—N=C(SCH$_3$)— | 3,5-diCF$_3$—Ph | solid* |
| 20 (Ex. 8) | CH$_3$O | —CH=N—N(CH$_3$)— | 3-CF$_3$-pyridin-2-yl | 185–187 |
| 21 | CH$_3$O | —CH=N—N(CH$_3$)— | 4-CF$_3$-pyridin-2-yl | 169–171 |
| 22 (Ex. 7) | CH$_3$O | —CH$_2$O—N=C(NH$_2$)— | 3,5-diCF$_3$—Ph | 177–178 |
| 23 | Cl | 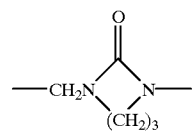 | 2-thiazolyl | 95–100 |
| 24 | Cl | | 3-CF$_3$—Ph | 125–130 |

INDEX TABLE A-continued

[Structure: phenyl group with Y-Z substituent at ortho position, attached to N of a triazolinone ring with X substituent, N-CH3, and C=O]

| Cmpd. No. | X | Y | Z | m.p. (° C.) |
|---|---|---|---|---|
| 25 | CH₃O | —CH₂N(C(=O))N—(CH₂)₃— (cyclic) | 2-thiazolyl | 166–170 |
| 26 | CH₃O | —CH₂N(C(=O))N—(CH₂)₂— (cyclic) | 3-CF₃—Ph | 130–135 |
| 27 | CH₃O | —CH₂S—C(SCH₃)=N— | 3-CF₃—Ph | oil* |
| 28 (Ex. 6) | CH₃O | —CH₂S—C(SCH₃)=N— | 4-Br—Ph | oil* |
| 29 | CH₃O | —CH₂S—C(SCH₃)=N— | 3,5-diCl—Ph | oil* |

*See Index Table B for ¹H NMR data.

INDEX TABLE B

| Cmpd. No. | ¹H NMR Data (CDCl₃ solution unless indicated otherwise)ᵃ |
|---|---|
| 2 | (for the E/Z mixture) δ 7.66 and 7.21(2s, 1H total), 7.25–7.54(m, 4H total), 3.93 and 3.91(2s, 3H total), 3.44(s, 3H), 1.54 and 1.25(2s, 9H total). |
| 3 | δ 7.58(m, 1H), 7.37(m, 2H), 7.23(m, 3H), 6.60(d, 2H), 4.23(s, 2H), 3.86(s, 3H), 3.41(s, 3H). |
| 4 | δ 8.18(s, 1H), 7.98(m, 1H), 7.82(m, 1H), 7.50(m, 4H), 7.30(d, 1H), 5.59(d, 1H), 5.46(d, 1H), 3.93(s, 3H), 3.41(s, 3H). |
| 5 | δ 7.56(m, 2H), 7.44(m, 3H), 7.25(m, 2H), 5.26(AB quartet, 2H), 3.9(s, 3H), 3.41(s, 3H), 2.1(s, 3H). |
| 6 | δ 7.68(d, 1H), 7.6(m, 1H), 7.48(m, 4H), 7.28(m, 1H), 5.41(AB quartet, 2H), 3.91(s, 3H), 3.38(s, 3H), 3.20(s, 3H). |
| 7 | δ 7.6(d, 1H), 7.3–7.5(m, 4H), 7.2(d, 1H), 6.95(s, 1H), 6.9(d, 1H), 4.27(s, 2H), 3.86(s, 3H), 3.41(s, 3H), 1.95(s, 3H). |
| 8 | δ 7.43(m, 3H), 7.28(m, 1H), 7.22(m, 2H), 7.15(m, 1H), 7.04(m, 1H), 5.12(q, 2H) 4.51(s, 2H), 3.89(s, 3H), 3.43(s, 3H), 1.91(s, 3H). |
| 9 | δ 7.45(m, 3H), 7.23(m, 1H), 5.06(q, 2H), 4.05(s, 2H), 3.93(s, 3H), 3.895(s, 3H), 3.44(s, 3H), 1.94(s, 3H). |
| 10 | δ 7.58(m, 1H), 7.41(m, 4H), 7.26(m, 3H), 5.12(q, 2H), 4.08(d, 2H), 3.92(s, 3H), 3.44(s, 3H), 1.96(s, 3H). |
| 11 | δ 7.57(m, 1H), 7.44(m, 3H), 7.32(d, 2H), 7.24(m, 1H), 5.27(q, 2H), 3.9(s, 3H), 3.415(s, 3H), 2.12(s, 3H). |
| 12 | δ 7.44(m, 3H), 7.23(m, 1H), 6.96(m, 1H), 6.81(m, 2H), 5.12(q, 2H), 4.44(s, 2H), 3.9(s, 3H), 3.43(s, 3H), 1.89(s, 3H). |
| 13 | δ 7.6(d, 1H), 7.15–7.5(m, 5H), 6.95(s, 1H), 6.85(d, 1H), 4.24(s, 2H), 3.85(s, 3H), 3.41(s, 3H), 2.3(m, 2H), 1.05(t, 3H). |
| 14 | δ 7.78(s, 2H), 7.625(s, 1H), 7.42(m, 3H), 7.23(m, 1H), 5.03(q, 2H), 3.92(d, 3H), 3.67(s, 2H), 3.42(s, 3H), 1.905(s, 3H). |
| 15 | δ 7.45(m, 4H), 7.33(s, 2H), 7.24(m, 1H), 5.12(q, 2H), 4.57(s, 2H), 3.91(s, 3H), 3.43(s, 3H), 1.925(s, 3H). |
| 16 | δ 8.0(m, 1H), 7.88(m, 1H), 7.625(m, 1H), 7.48(m, 4H), 7.25(m, 1H), 5.09(m, 2H), 4.046(s, 3H), 3.75(s, 3H), 3.49(s, 3H), 2.41(s, 3H), 2.32(s, 3H). Compound is a 1:2 mixture of geometric isomers. |
| 17 | δ 7.85(m, 1H), 7.75(m, 1H), 7.38(m, 6H), 5.10(q, 2H), 4.10(s, 2H), 3.91(s, 3H), 3.44(s, 3H), 1.95(s, 3H). |
| 18 | δ 7.41(m, 3H), 7.21(m, 3H), 7.14(m, 1H), 5.06(q, 2H), 3.9(s, 3H), 3.58(s, 2H), 3.43(s, 3H), 1.89(s, 3H). |
| 19 | δ 7.93(m, 3H), 7.56(m, 1H), 7.43(m, 2H), 7.25(m, 1H), 5.3(q, 2H), 3.89(s, 3H), 3.4(s, 3H), 2.15(s, 3H). |
| 27 | δ 7.55(d, 1H), 7.39(m, 4H), 7.2(m, 1H), 7.08(1H), 6.99(d, 1H), 4.34(m, 2H), 3.84(s, 3H), 3.42(s, 3H), 2.46(s, 3H). |
| 28 | δ 7.55(s, 1H), 7.4(m, 4H), 7.2(m, 1H), 6.7(m, 2H), 4.33(m, 2H), 3.86(s, 3H), 3.43(s, 3H), 2.44(s, 3H). |
| 29 | δ 7.53(d, 1H), 7.4(m, 2H), 7.2(m, 1H), 7.06(m, 1H), 6.71(d, 2H), 4.32(q, 2H), 3.875(s, 3H), 3.44(s, 3H), 2.46(s, 3H). |

ᵃ¹H NMR data are in ppm downfield from tetramethylsilane. Couplings are designated by(s)-singlet, (d)-doublet, (t)-triplet, (q)-quartet, (m)-multiplet.

BIOLOGICAL EXAMPLES OF THE INVENTION

Test compounds were first dissolved in acetone in an amount equal to 3% of the final volume and then suspended at a concentration of 200 ppm in purified water containing 250 ppm of the surfactant Trem® 014 (polyhydric alcohol esters). The resulting test suspensions were then used in the following tests. Spraying these 200 ppm test suspensions to the point of run-off on the test plants is the equivalent of a rate of 500 g/ha.

TEST A

The test suspension was sprayed to the point of run-off on wheat seedlings. The following day the seedlings were inoculated with a spore dust of *Erysiphe graminis* f. sp. tritici, (the causal agent of wheat powdery mildew) and incubated in a growth chamber at 20° C. for 7 days, after which disease ratings were made.

TEST B

The test suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 h, and then moved to a growth chamber at 20° C. for 6 days, after which disease ratings were made.

TEST C

The test suspension was sprayed to the point of run-off on rice seedlings. The following day the seedlings were inoculated with a spore suspension of *Pyricularia oryzae* (the causal agent of rice blast) and incubated in a saturated atmosphere at 27° C. for 24 h, and then moved to a growth chamber at 30° C. for 5 days, after which disease ratings were made.

TEST D

The test suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 h, and then moved to a growth chamber at 20° C. for 5 days, after which disease ratings were made.

TEST E

The test suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 h, moved to a growth chamber at 20° C. for 6 days, and then incubated in a saturated atmosphere at 20° C. for 24 h, after which disease ratings were made.

TEST F

The test suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 20° C. for 5 days, after which disease ratings were made.

Results for Tests A–F are given in Table A. In the table, a rating of 100 indicates 100% disease control and a rating of 0 indicates no disease control (relative to the controls). A dash (-) indicates no test results.

TABLE A

| Cmpd No. | Test A | Test B | Test C | Test D | Test E | Test F |
|---|---|---|---|---|---|---|
| 1 | 39 | 28 | 0 | 0 | 0 | 0 |
| 2 | 99 | 99 | 86 | 96 | 89[b] | 0 |
| 3 | 85 | 100 | 91 | 63 | 43[a] | 42 |
| 4 | 39 | 85 | 0 | 0 | 34[a] | 37 |
| 5 | 98 | 100 | 74 | 86 | 100[a] | 0 |
| 6 | 97 | 97 | 0 | 0 | 0[a] | 47 |
| 7 | 91 | 100 | 53 | 25 | 83[a] | 0 |
| 8 | 57 | 100 | 74 | 74 | 51[a] | 45 |
| 9 | 57 | 66 | 0 | 74 | 3[a] | 0 |
| 10 | 95 | 99 | 0 | 0 | 16[a] | 48 |

TABLE A-continued

| Cmpd No. | Test A | Test B | Test C | Test D | Test E | Test F |
|---|---|---|---|---|---|---|
| 11 | 98 | 100 | 53 | 26 | 95[a] | 48 |
| 12 | 99 | 100 | 53 | 0 | 44[a] | 10 |
| 13 | 76 | 97 | 53 | 0 | 100 | 10 |
| 14 | 61 | 93 | 0 | 26 | 29[a] | 0 |
| 15 | 91 | 97 | 53 | 26 | 6[a] | 0 |
| 16 | 99 | 99 | 53 | 99 | 50[a] | 0 |
| 17 | 99 | 99 | 32 | 91 | 53[a] | 79 |
| 18 | 25 | 93 | 32 | 25 | 68[a] | 0 |
| 19 | 100 | 100 | 74 | 70 | 57[a] | 64 |
| 20 | 86 | 68 | 0 | 0 | 2[a] | 0 |
| 21 | 0 | 0 | 0 | 41 | 19[a] | 0 |
| 22 | 100 | 93 | 73 | 16 | 0[a] | 0 |
| 23 | 34 | 67 | 0 | 73 | — | 0 |
| 24 | 34 | 67 | 0 | 16 | — | 0 |
| 25 | 0 | 0 | 0 | 0 | 11[a] | 7 |
| 26 | 28 | 67 | 0 | 32 | 11[a] | 0 |
| 27 | 94 | 100 | 86 | 13 | 35[a] | 0 |
| 28 | — | — | — | — | — | — |
| 29 | — | — | — | — | — | — |

[a]Compound was tested at 10 ppm (equivalent to 25 g/ha).
[b]Compound was tested at 40 ppm (equivalent to 100 g/ha).

What is claimed is:

1. A compound selected from Formula I, N-oxides and agriculturally suitable salts thereof,

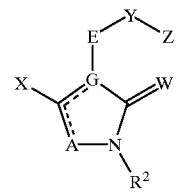

I wherein:
E is 1,2-phenylene optionally substituted with one of $R^3$, $R^4$, or both $R^3$ and $R^4$;
A is N or $CR^{14}$;
G is N and the floating double bond is attached to A;
W is O; S; NH; $N(C_1–C_6$ alkyl); or $NO(C_1–C_6$ alkyl);
X is $OR^1$; $S(O)_mR^1$; or halogen;
$R^1$ is $C_1–C_6$ alkyl; $C_1–C_6$ haloalkyl; $C_2–C_6$ alkenyl; $C_2–C_6$ haloalkenyl; $C_2–C_6$ alkynyl; $C_2–C_6$ haloalkynyl; $C_3–C_6$ cycloalkyl; $C_2–C_4$ alkylcarbonyl; or $C_2–C_4$ alkoxycarbonyl;
$R^2$ is H; $C_1–C_6$ alkyl; $C_1–C_6$ haloalkyl; $C_2–C_6$ alkenyl; $C_2–C_6$ haloalkenyl; $C_2–C_6$ alkynyl; $C_2–C_6$ haloalkynyl; $C_3–C_6$ cycloalkyl; $C_2–C_4$ alkylcarbonyl; or $C_2–C_4$ alkoxycarbonyl;
$R^3$ and $R^4$ are each independently halogen; cyano; nitro; hydroxy; $C_1–C_6$ alkyl; $C_1–C_6$ haloalkyl; $C_2–C_6$ alkenyl; $C_2–C_6$ haloalkenyl; $C_2–C_6$ alkynyl; $C_2–C_6$ haloalkynyl; $C_1–C_6$ alkoxy; $C_1–C_6$ haloalkoxy; $C_2–C_6$ alkenyloxy; $C_2–C_6$ alkynyloxy; $C_1–C_6$ alkylthio; $C_1–C_6$ alkylsulfinyl; $C_1–C_6$ alkylsulfonyl; formyl; $C_2–C_6$ alkylcarbonyl; $C_2–C_6$ alkoxycarbonyl; $NH_2C(O)$; $(C_1–C_4$ alkyl)NHC(O); $(C_1–C_4$ alkyl)$_2$NC(O); $Si(R^{25})_3$; $Ge(R^{25})_3$; $(R^{25})_3Si-C\equiv C-$; or phenyl, phenylethynyl, benzoyl, or phenylsulfonyl each substituted with $R^8$ and optionally substituted with one or more $R^{10}$; or
when $R^3$ and $R^4$ are attached to adjacent atoms, $R^3$ and $R^4$ can be taken together as $C_3–C_5$ alkylene, $C_3–C_5$ haloalkylene, $C_3$–$C_5$ alkenylene or $C_3$–$C_5$ haloalkenylene each optionally substituted with 1–2 $C_1$–$C_3$ alkyl;

Y is —$NR^{15}$—; —C(=O)—; —$CHR^{15}OC(=S)N(R^{15})$—; —$CHR^{15}S$—$C(R^7)$=N—; —$C(R^7)$=N—$NR^{15}$—; —CH=N—N=$C(R^7)$—; —$CHR^{15}N(COCH_3)$—N=$C(R^7)$—; —OC(=S)$NR^{15}C$(=O)—; —$CHR^6$—C(=$W^1$)—$A^1$—; —$CHR^6CHR^6$—C(=$W^1$)—$A^1$—; —$CR^6$=$CR^6$—C(=$W^1$)—$A^1$—; —C≡C—C(=$W^1$)—$A^1$—; —N=$CR^6$—C(=$W^1$)—$A^1$—; —CH(O$R^{26}$)—; —$CHR^{27}$—; —$CHR^6CHR^{28}$—; —$CHR^{28}CHR^6$—; —$CR^6$=$CR^{29}$—; —$CR^{29}$=$CR^6$—; —$CHR^{30}$O—; —OCH$R^{30}$—; —$CHR^{30}S(O)_n$—; —$S(O)_nCHR^{30}$—; —$CHR^{30}$O—N=$C(R^7)$—; —$CHR^{15}$O—N=C($R^{31}$)—; —($R^7$)C=N—OCH($R^{30}$)—; —($R^{31}$)C=N—OCH($R^{15}$)—; —C($R^{31}$)=N—O—; —O—N=C($R^{31}$)—; —$CHR^{30}$OC(=O)N($R^{15}$)—; or —$CHR^{15}$OC(=O)N($R^{32}$)—; and the directionality of the Y linkage is defined such that the moiety depicted on the left side of the linkage is bonded to E and the moiety on the right side of the linkage is bonded to Z;

$W^1$ is O or S;

$A^1$ is O; S; $NR^{15}$; or a direct bond;

each $R^6$ is independently H; 1–2 $CH_3$; $C_2$–$C_3$ alkyl; $C_1$–$C_3$ alkoxy; $C_3$–$C_6$ cycloalkyl; formylamino; $C_2$–$C_4$ alkylcarbonylamino; $C_2$–$C_4$ alkoxycarbonylamino; $NH_2C(O)NH$; ($C_1$–$C_3$ alkyl)NHC(O)NH; ($C_1$–$C_3$ alkyl)$_2$NC(O)NH; N($C_1$–$C_3$ alkyl)$_2$; piperidinyl; morpholinyl; 1–2 halogen; cyano; or nitro;

$R^7$ is H; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_1$–$C_6$ alkylsulfinyl; $C_1$–$C_6$ alkylsulfonyl; $C_1$–$C_6$ haloalkylthio; $C_1$–$C_6$ haloalkylsulfinyl; $C_1$–$C_6$ haloalkylsulfonyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; halogen; cyano; or morpholinyl;

Z is selected from:
a) $C_3$–$C_8$ cycloalkyl and phenyl each substituted with $R^9$ and optionally substituted with one or more $R^{10}$;
b) a ring system selected from 3 to 14-membered monocyclic, fused bicyclic and fused tricyclic non-aromatic heterocyclic ring systems and 5 to 14-membered monocyclic, fused bicyclic and fused tricyclic aromatic heterocyclic ring systems, each heterocyclic ring system containing 1 to 6 heteroatoms independently selected from the group nitrogen, oxygen, and sulfur, provided that each heterocyclic ring system contains no more than 4 nitrogens, no more than 2 oxygens, and no more than 2 sulfurs, each nonaromatic or aromatic heterocyclic ring system substituted with $R^9$ and optionally substituted with one or more $R^{10}$; and
c) a multicyclic ring system selected from 8 to 14-membered fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and $S(O)_2$, and any remaining rings as aromatic carbocyclic rings, each multicyclic ring system substituted with $R^9$ and optionally substituted with one or more $R^{10}$;

each Q is independently selected from the group —$CHR^{13}$—, —$NR^{13}$—, —O—, and —$S(O)_p$—;

$R^8$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$($C_1$–$C_6$ alkyl); NH($C_1$–$C_6$ alkyl); N($C_1$–$C_6$ alkyl)$_2$; cyano; nitro; $SiR^{19}R^{20}R^{21}$; or $GeR^{19}R^{20}R^{21}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$($C_1$–$C_6$ alkyl); NH($C_1$–$C_6$ alkyl); N($C_1$–$C_6$ alkyl)$_2$; —C($R^{18}$)=$NOR^{17}$; cyano; nitro; $SF_5$; $SiR^{22}R^{23}R^{24}$; or $GeR^{22}R^{23}R^{24}$; or $R^9$ is phenyl, benzyl, benzoyl, phenoxy, pyridinyl, pyridinyloxy, thienyl, thienyloxy, furanyl, pyrimidinyl, or pyrimidinyloxy each optionally substituted with one of $R^{11}$, $R^{12}$, or both $R^{11}$ and $R^{12}$;

each $R^{10}$ is independently halogen; $C_1$–$C_4$ alkyl; $C_1$–$C_4$ haloalkyl; $C_1$–$C_4$ alkoxy; nitro; or cyano; or when $R^9$ and an $R^{10}$ are attached to adjacent atoms on Z, $R^9$ and said adjacently attached $R^{10}$ can be taken together as —$OCH_2O$— or —$OCH_2CH_2O$—; each $CH_2$ group of said taken together $R^9$ and $R^{10}$ optionally substituted with 1–2 halogen; or when Y and an $R^{10}$ are attached to adjacent atoms on Z and Y is —$CHR^{30}$O—N=$C(R^7)$—, $R^7$ and said adjacently attached $R^{10}$ can be taken together as —$(CH_2)_r$—J— such that J is attached to Z;

J is —$CH_2$—; —$CH_2CH_2$—; —$OCH_2$—; —$CH_2O$—; —$SCH_2$—; —$CH_2S$—; —N($R^{16}$)$CH_2$—; or —$CH_2N(R^{16})$—; each $CH_2$ group of said J optionally substituted with 1 to 2 $CH_3$; $R^{11}$ and $R^{12}$ are each independently halogen; $C_1$–$C_4$ alkyl; $C_1$–$C_4$ haloalkyl; $C_1$–$C_4$ alkoxy; $C_1$–$C_4$ haloalkoxy; nitro; cyano; $Si(R^{25})_3$; or $Ge(R^{25})_3$;

each $R^{13}$ is independently H; $C_1$–$C_6$ alkyl; $C_1$–$C_6$ haloalkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{14}$ is H; halogen; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; or $C_3$–$C_6$ cycloalkyl;

each $R^{15}$ is independently H; $C_1$–$C_3$ alkyl; $C_3$–$C_6$ cycloalkyl; or phenyl or benzyl, each optionally substituted on the phenyl ring with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{16}$, $R^{17}$, and $R^{18}$ are each independently H; $C_1$–$C_3$ alkyl; $C_3$–$C_6$ cycloalkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{19}$, $R^{20}$, $R^{21}$, $R^{22}$, $R^{23}$, and $R^{24}$ are each independently $C_1$–$C_6$ alkyl; $C_1$–$C_4$ alkoxy; or phenyl;

each $R^{25}$ is independently $C_1$–$C_4$ alkyl or phenyl;

$R^{26}$ is H; $C_1$–$C_3$ alkyl; $C_3$–$C_6$ cycloalkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{27}$ and $R^{28}$ are each independently $C_1$–$C_3$ alkoxy; $C_3$–$C_6$ cycloalkyl; formylamino; $C_2$–$C_4$ alkylcarbonylamino; $C_2$–$C_4$ alkoxycarbonylamino; $NH_2C(O)NH$; ($C_1$–$C_3$ alkyl)NHC(O)NH; ($C_1$–$C_3$ alkyl)$_2$NC(O)NH; N($C_1$–$C_3$ alkyl)$_2$; piperidinyl; morpholinyl; cyano; or nitro;

$R^{29}$ is $C_1$–$C_3$ alkoxy; $C_3$–$C_6$ cycloalkyl; formylamino; $C_2$–$C_4$ alkylcarbonylamino; $C_2$–$C_4$ alkoxycarbonylamino; $NH_2C(O)NH$; $(C_1$–$C_3$ alkyl)$NHC(O)NH$; $(C_1$–$C_3$ alkyl)$_2NC(O)NH$; $N(C_1$–$C_3$ alkyl)$_2$; piperidinyl; morpholinyl; halogen; cyano; or nitro;

$R^{30}$ is $C_3$–$C_6$ cycloalkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{31}$ is $C_1$–$C_6$ alkylthio; $C_1$–$C_6$ alkylsulfinyl; $C_1$–$C_6$ alkylsulfonyl; $C_1$–$C_6$ haloalkylthio; $C_1$–$C_6$ haloalkylsulfinyl; $C_1$–$C_6$ haloalkylsulfonyl; or halogen;

$R^{32}$ is $C_3$–$C_6$ cycloalkyl;

m, n and each p are each independently 0, 1 or 2;

r is 0 or 1; and s is 2 or 3;

provided that 1) when Y is —$NR^{15}$—, $R^{15}$ is H or $C_1$–$C_3$ alkyl, and $R^9$ is $SiR^{22}R^{23}R^{24}$ or $GeR^{22}R^{23}R^{24}$, then Z is other than phenyl or a 5 to 14-membered aromatic heterocyclic ring system each substituted with $R^9$ and optionally substituted with one or more $R^{10}$;

2) when Y is —C(=O)— and $R^9$ is $SiR^{22}R^{23}R^{24}$ or $GeR^{22}R^{23}R^{24}$, then Z is other than phenyl or a 5 to 14-membered aromatic heterocyclic ring system each substituted with $R^9$ and optionally substituted with one or more $R^{10}$;

3) when Y is —$CH(OR^{26})$—, $R^{26}$ is H or $C_1$–$C_3$ alkyl, and $R^9$ is $SiR^{22}R^{23}R^{24}$ or $GeR^{22}R^{23}R^{24}$, then Z is other than phenyl or a 5 to 14-membered aromatic heterocyclic ring system each substituted with $R^9$ and optionally substituted with one or more $R^{10}$;

4) when Y is —$NR^{15}$— and $R^{15}$ is H or $C_1$–$C_3$ alkyl, then Z is other than
   i) an N-oxide of a 5 to 14-membered aromatic heterocyclic ring system substituted with $R^9$ and optionally substituted with one or more $R^{10}$; or
   ii) a 8 to 14-membered multicyclic ring system selected from fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$ substituted with $R^9$ and optionally substituted with one or more $R^{10}$;

5) when Y is —$CHR^{15}O$—N=C($R^{31}$)— or —($R^{31}$)C=N—$OCH(R^{15})$—, $R^{15}$ is H or $C_1$–$C_3$ alkyl and $R^{31}$ is $C_1$–$C_6$ alkylthio, $C_1$–$C_6$ alkylsulfinyl, $C_1$–$C_6$ alkylsulfonyl, $C_1$–$C_6$ haloalkylthio, $C_1$–$C_6$ haloalkylsulfinyl, $C_1$–$C_6$ haloalkylsulfonyl or halogen, then Z is other than
   i) an N-oxide of a 5 to 14-membered aromatic heterocyclic ring system substituted with $R^9$ and optionally substituted with one or more $R^{10}$; or
   ii) a 8 to 14-membered multicyclic ring system selected from fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$ substituted with $R^9$ and optionally substituted with one or more $R^{10}$;

6) when Y is —C(=O)—, then Z is other than
   i) an N-oxide of a 5 to 14-membered aromatic heterocyclic ring system substituted with $R^9$ and optionally substituted with one or more $R^{10}$; or
   ii) a 8 to 14-membered multicyclic ring system selected from fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$ substituted with $R^9$ and optionally substituted with one or more $R^{10}$;

7) when Y is —C($R^{31}$)=N—O— or —O—N=C($R^{31}$)— and $R^{31}$ is $C_1$–$C_6$ alkylthio, $C_1$–$C_6$ alkylsulfinyl, $C_1$–$C_6$ alkylsulfonyl, $C_1$–$C_6$ haloalkylthio, $C_1$–$C_6$ haloalkylsulfinyl, $C_1$–$C_6$ haloalkylsulfonyl or halogen, then Z is other than
   i) an N-oxide of a 5 to 14-membered aromatic heterocyclic ring system substituted with $R^9$ and optionally substituted with one or more $R^{10}$; or
   ii) a 8 to 14-membered multicyclic ring system selected from fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$ substituted with $R^9$ and optionally substituted with one or more $R^{10}$; and 8) when Y is —$CH(OR^{26})$— and $R^{26}$ is H or $C_1$–$C_3$ alkyl, then Z is other than
   i) an N-oxide of a 5 to 14-membered aromatic heterocyclic ring system substituted with $R^9$ and optionally substituted with one or more $R^{10}$; or
   ii) a 8 to 14-membered multicyclic ring system selected from fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$ substituted with $R^9$ and optionally substituted with one or more $R^{10}$.

2. A compound of claim 1 wherein:

W is O;

$R^1$ is $C_1$–$C_3$ alkyl or $C_1$–$C_3$ haloalkyl;

$R^2$ is H; $C_1$–$C_6$ alkyl; $C_1$–$C_6$ haloalkyl; or $C_3$–$C_6$ cycloalkyl;

$R^3$ and $R^4$ are each independently halogen; cyano; nitro; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylsulfonyl; $C_2$–$C_6$ alkylcarbonyl; $C_2$–$C_6$ alkoxycarbonyl; $(C_1$–$C_4$ alkyl)NHC(O); $(C_1$–$C_4$ alkyl)$_2$NC(O); benzoyl; or phenylsulfonyl;

Y is —$CH_2S$—C($R^7$)=N—; —CH=$CR^6$—C(=$W^1$)—$A^1$—; —$CH_2O$—N=C($R^{31}$)—; —($R^7$)C=N—OCH($R^{30}$)—; or —C($R^{31}$)=N—O—;

$R^7$ is H; $C_1$–$C_6$ alkyl; $C_1$–$C_6$ haloalkyl; $C_1$–$C_6$ alkoxy; $C_1$–$C_6$ alkylthio; $C_2$–$C_6$ alkenyl; $C_2$–$C_6$ alkynyl; $C_3$–$C_6$ cycloalkyl; halogen; or cyano;

Z is selected from the group $C_3$–$C_8$ cycloalkyl; phenyl; naphthalenyl; anthracenyl; phenanthrenyl; 1H-pyrrolyl; furanyl; thienyl; 1H-pyrazolyl; 1H-imidazolyl; isoxazolyl; oxazolyl; isothiazolyl; thiazolyl; 1H-1,2,3-triazolyl; 2H-1 2,3-triazolyl; 1H-1,2,4-triazolyl; 4H-1,2,4-triazolyl; 1,2,3-oxadiazolyl; 1,2,4-oxadiazolyl; 1,2,5-oxadiazolyl; 1,3,4-oxadiazolyl; 1,2,3-thiadiazolyl; 1,2,4-thiadiazolyl; 1,2,5-thiadiazolyl; 1,3,4-thiadiazolyl; 1H-tetrazolyl; 2H-tetrazolyl; pyridinyl; pyridazinyl; pyrimidinyl; pyrazinyl; 1,3,5- triazinyl; 1,2,4-triazinyl; 1,2,4,5-tetrazinyl; 1H-indolyl; benzofuranyl; benzo[b]thiophenyl; 1H-indazolyl; 1H-benzimidazolyl; benzoxazolyl; benzothiazolyl; quinolinyl; isoquinolinyl; cinnolinyl; phthalazinyl; quinazolinyl; quinoxalinyl; 1,8-naphthyridinyl; pteridinyl; 2,3-dihydro-1H-indenyl; 1,2,3,4-tetrahydronaphthalenyl; 6,7,8,9-tetrahydro-5H-benzocycloheptenyl; 5,6,7,8,9,10-hexahydrobenzocyclooctenyl; 2,3-dihydro-3-oxobenzofuranyl; 1,3-dihydro-1-oxoisobenzofuranyl; 2,3-dihydro-2-oxobenzofuranyl; 3,4-dihydro-4-oxo-2H-1-benzopyranyl; 3,4-dihydro-1-oxo-1H-2-benzopyranyl; 3,4-dihydro-3-oxo-1H-2-benzopyranyl; 3,4-dihydro-2-oxo-2H-1-benzopyranyl; 4-oxo-4H-1-benzopyranyl; 2-oxo-2H-1-benzopyranyl; 2,3,4,5-tetrahydro-5-oxo-1-benzoxepinyl; 2,3,4,5-tetrahydro-2-oxo-1-benzoxepinyl; 2,3-dihydro-1,3-dioxo-1H-isoindolyl; 1,2,3,4-tetrahydro-1,3-dioxoisoquinolinyl; 3,4-dihydro-2,4-dioxo-2H-1,3-benzoxazinyl; 2-oxo-1,3-benzodioxyl; 2,3-dihydro-1,1,3-trioxo-1,2-benzisothiazolyl; 9H-fluorenyl; azulenyl; and thiazolo[2,3-c]-1,2,4-triazolyl; each group substituted with $R^9$ and optionally substituted with one or more $R^{10}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; cyano; $CO_2(C_1$–$C_6$ alkyl); $NH(C_1$–$C_6$ alkyl); $N(C_1$–$C_6$ alkyl)$_2$; $SiR^{22}R^{23}R^{24}$; or $GeR^{22}R^{23}R^{24}$; or $R^9$ is $C_3$–$C_6$ cycloalkyl, phenyl, phenoxy, pyridinyl, pyridinyloxy, pyrimidinyl, or pyrimidinyloxy, each optionally substituted with one of $R^{11}$, $R^{12}$, or both $R^{11}$ and $R^{12}$; and $R^{30}$ is $C_3$–$C_6$ cycloalkyl.

3. A compound of claim 2 wherein:

Z is selected from the group phenyl; pyridinyl; pyrimidinyl; and naphthalenyl; each group substituted with $R^9$ and optionally substituted with one or more $R^{10}$; and $R^7$ is H; $C_1$–$C_6$ alkyl; $C_1$–$C_6$ haloalkyl; $C_1$–$C_6$ alkoxy; $C_1$–$C_6$ alkylthio; $C_2$–$C_6$ alkenyl; $C_2$–$C_6$ alkynyl; cyclopropyl; halogen; or cyano.

4. A compound of claim 3 wherein:

X is $OR^1$;

$R^1$ is $C_1$–$C_3$ alkyl;

$R^2$ is H or $C_1$–$C_2$ alkyl;

Y is —$CH_2S$—$C(R^7)$=N—; —CH=$CR^6$—$C(=W^1)$—$A^1$—; —$CH_2O$—N=$C(R^{31})$—; or —$(R^7)C$=N—$OCH(R^{30})$—;

$R^7$ is H; $C_1$–$C_3$ alkyl; $C_1$–$C_3$ haloalkyl; $C_1$–$C_3$ alkoxy; $C_1$–$C_3$ alkylthio; or cyclopropyl; and $R^{30}$ is cyclopropyl.

5. A compound of claim 4 wherein:

Y is —CH=$CR^6$—$C(=W^1)$—$A^1$—; or —$CH_2O$—N=$C(R^{31})$—.

6. A compound of claim 5 wherein:

$R^1$ is methyl; and $R^2$ is methyl.

7. The compound of claim 4 which is selected from the group:

[[2-(1,5-dihydro-3-methoxy-1-methyl-5-oxo-4H-1,2,4-triazol-4-yl)phenyl]methyl]N-(4-chlorophenyl)propanimidothioate;

1,1-dimethylethyl 2-chloro-3-[2-(1,5-dihydro-3-methoxy-1-methyl-5-oxo-4H-1,2,4-triazol-4-yl)phenyl]-2-propenoate; and S-methyl 3,4-dichloro-N-[[2-(1,5-dihydro-3-methoxy-1-methyl-5-oxo-4H-1,2,4-triazol-4-yl)phenyl]methoxy]benzenecarbonimidothioate.

8. The compound of claim 6 which is 2,4-dihydro-5-methoxy-2-methyl-4-[2-[[[[(methylthio)[3-(trifluoromethyl)phenyl]methylene]amino]oxy]methyl]phenyl]-3H-1,2,4-triazol-3-one.

9. A fungicidal composition comprising a fungicidally effective amount of a compound of claim 1 and at least one of a surfactant, a solid diluent or a liquid diluent.

10. A method for controlling plant diseases caused by fungal plant pathogens comprising applying to the plant or portion thereof, or to the plant seed or seedling, a fungicidally effective amount of a compound of claim 1.

* * * * *